US012117602B2

United States Patent
Fujikura et al.

(10) Patent No.: US 12,117,602 B2
(45) Date of Patent: Oct. 15, 2024

(54) WIDE-ANGLE OPTICAL SYSTEM AND IMAGE PICKUP APPARATUS USING THE SAME

(71) Applicant: OLYMPUS CORPORATION, Hachioji (JP)

(72) Inventors: Takashi Fujikura, Hamura (JP); Keisuke Ichikawa, Tama (JP); Shinichi Mihara, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 872 days.

(21) Appl. No.: 17/189,679

(22) Filed: Mar. 2, 2021

(65) Prior Publication Data

US 2021/0255439 A1     Aug. 19, 2021

Related U.S. Application Data

(63) Continuation of application No. PCT/JP2019/008034, filed on Mar. 1, 2019.

(51) Int. Cl.
*G02B 23/24*     (2006.01)
*A61B 1/00*     (2006.01)
(Continued)

(52) U.S. Cl.
CPC ........ *G02B 23/243* (2013.01); *A61B 1/00163* (2013.01); *G02B 13/04* (2013.01); *G02B 15/143507* (2019.08); *A61B 1/00183* (2013.01)

(58) Field of Classification Search
CPC .................. G02B 23/243; G02B 13/04; G02B 15/143507; A61B 1/00163;
(Continued)

(56) References Cited

U.S. PATENT DOCUMENTS 5,949,589 A    9/1999   Nakazawa
6,246,529 B1   6/2001   Sensui
(Continued)

FOREIGN PATENT DOCUMENTS

JP     H10260346 A     9/1998
JP     2000131606 A    5/2000
(Continued)

OTHER PUBLICATIONS

International Search Report (ISR) (and English language translation thereof) dated Jun. 4, 2019, issued in International Application No. PCT/JP2019/008028.
(Continued)

*Primary Examiner* — Marin Pichler
*Assistant Examiner* — Justin W. Hustoft
(74) *Attorney, Agent, or Firm* — Holtz, Holtz & Volek PC

(57) ABSTRACT

A wide-angle optical system includes a first lens unit having a negative refractive power, a second lens unit having a positive refractive power, and a third lens unit having a positive refractive power. At the time of carrying out a focal-position adjustment, the second lens unit is moved. The third lens unit includes a positive single lens on an image side of a cemented surface Sc having a negative refractive power nearest to an image in the third lens unit, and has a plurality of refractive surfaces having a negative refractive power on the object side of the cemented surface Sc. The third lens unit has at least one refractive surface Sp having a positive refractive power which satisfies following conditional expression (1):

$$0.02 < fL/Rsp < 1.20 \qquad (1).$$

A wide-angle optical system includes a first lens unit having a negative refractive power, a second lens unit having a positive refractive power, and a third lens unit having a positive refractive power. At the time of carrying out a
(Continued)

focal-position adjustment, the second lens unit is moved. The third lens unit includes a positive single lens on an image side of a cemented surface Sc having a negative refractive power nearest to an image in the third lens unit, and has a plurality of refractive surfaces having a negative refractive power on the object side of the cemented surface Sc. The third lens unit has at least one refractive surface Sp having a positive refractive power which satisfies following conditional expression (1):

$$0.02 < fL/Rsp < 1.20 \qquad (1).$$

30 Claims, 26 Drawing Sheets

(51) Int. Cl.
  *G02B 13/04* (2006.01)
  *G02B 15/14* (2006.01)
(58) Field of Classification Search
  CPC .......... A61B 1/143507; A61B 1/00183; A61B 1/00096; A61B 1/00174
  See application file for complete search history.

(56) References Cited

U.S. PATENT DOCUMENTS

| | | | |
|---|---|---|---|
| 6,317,270 B2* | 11/2001 | Nagaoka | G02B 15/177 359/740 |
| 7,016,120 B2 | 3/2006 | Achtner et al. | |
| 8,203,793 B2 | 6/2012 | Wada et al. | |
| 8,345,357 B2 | 1/2013 | Imoka | |
| 8,665,537 B2 | 3/2014 | Roth et al. | |
| 8,717,684 B2 | 5/2014 | Sano et al. | |
| 8,824,059 B2 | 9/2014 | Kato et al. | |
| 8,867,147 B2 | 10/2014 | Kimura | |
| 8,908,273 B2 | 12/2014 | Fujimoto | |
| 8,934,176 B2 | 1/2015 | Yamagami et al. | |
| 9,097,881 B2 | 8/2015 | Yamagami | |
| 9,110,278 B2 | 8/2015 | Sugita | |
| 9,459,443 B2 | 10/2016 | Uzawa et al. | |
| 9,766,437 B2 | 9/2017 | Sato | |
| 9,952,416 B2 | 4/2018 | Ichikawa | |
| 9,958,653 B2 | 5/2018 | Ichikawa | |
| 9,958,656 B2 | 5/2018 | Kawamura et al. | |
| 10,095,012 B2 | 10/2018 | Yamagami | |
| 10,114,200 B2 | 10/2018 | Ichikawa | |
| 10,191,253 B2 | 1/2019 | Ichikawa et al. | |
| 10,191,258 B2 | 1/2019 | Ichikawa et al. | |
| 10,197,768 B2 | 2/2019 | Ichikawa et al. | |
| 10,197,769 B2 | 2/2019 | Ichikawa et al. | |
| 10,274,705 B2 | 4/2019 | Ichikawa et al. | |
| 10,288,856 B2 | 5/2019 | Fujikura et al. | |
| 10,656,399 B2 | 5/2020 | Fujikura et al. | |
| 10,663,705 B2 | 5/2020 | Ichikawa et al. | |
| 10,768,396 B2 | 9/2020 | Kawamura et al. | |
| 10,830,991 B2 | 11/2020 | Ichikawa et al. | |
| 2003/0189767 A1 | 10/2003 | Achtner et al. | |
| 2010/0290133 A1 | 11/2010 | Sano et al. | |
| 2011/0002046 A1 | 1/2011 | Wada et al. | |
| 2011/0032606 A1 | 2/2011 | Imaoka | |
| 2011/0116172 A1 | 5/2011 | Yamagami et al. | |
| 2011/0317282 A1 | 12/2011 | Kimura | |
| 2012/0019926 A1 | 1/2012 | Yamagami | |
| 2012/0069441 A1 | 3/2012 | Fujimoto et al. | |
| 2012/0307374 A1 | 12/2012 | Kato et al. | |
| 2013/0265653 A1 | 10/2013 | Kimura | |
| 2014/0002910 A1 | 1/2014 | Roth et al. | |
| 2014/0125858 A1 | 5/2014 | Sugita | |
| 2015/0042773 A1 | 2/2015 | Uzawa et al. | |
| 2015/0268460 A1* | 9/2015 | Takada | G02B 13/04 359/738 |
| 2015/0293353 A1 | 10/2015 | Chin et al. | |
| 2017/0038563 A1 | 2/2017 | Sato | |
| 2017/0068079 A1 | 3/2017 | Kawamura et al. | |
| 2017/0168281 A1 | 6/2017 | Furuya et al. | |
| 2018/0052311 A1 | 2/2018 | Machida | |
| 2018/0210179 A1 | 7/2018 | Kawamura et al. | |
| 2019/0079269 A1 | 3/2019 | Kimura | |
| 2019/0086658 A1 | 3/2019 | Takato | |
| 2019/0302432 A1 | 10/2019 | Iwasawa et al. | |
| 2020/0018947 A1 | 1/2020 | Tsuyuki | |

FOREIGN PATENT DOCUMENTS

| | | |
|---|---|---|
| JP | 2003307672 A | 10/2003 |
| JP | 2004233797 A | 8/2004 |
| JP | 2010266577 A | 11/2010 |
| JP | 2011013469 A | 1/2011 |
| JP | 2011053663 A | 3/2011 |
| JP | 2011107267 A | 6/2011 |
| JP | 2012027309 A | 2/2012 |
| JP | 2012027451 A | 2/2012 |
| JP | 2012068303 A | 4/2012 |
| JP | 2012247689 A | 12/2012 |
| JP | 2013015621 A | 1/2013 |
| JP | 2014056133 A | 3/2014 |
| JP | 2014092728 A | 5/2014 |
| JP | 2015114509 A | 6/2015 |
| JP | 2016139087 A | 8/2016 |
| JP | 2016184136 A | 10/2016 |
| JP | 2017068114 A | 4/2017 |
| JP | 2017122743 A | 7/2017 |
| JP | 2018004726 A | 1/2018 |
| JP | 2018040948 A | 3/2018 |
| JP | 2018045097 A | 3/2018 |
| JP | 2018189733 A | 11/2018 |
| JP | 2019015958 A | 1/2019 |
| JP | 2019184733 A | 10/2019 |
| WO | 2014129089 A1 | 8/2014 |
| WO | 2016067838 A1 | 5/2016 |
| WO | 2017199614 A1 | 11/2017 |
| WO | 2018173412 A1 | 9/2018 |
| WO | 2020178883 A1 | 9/2020 |
| WO | 2020178884 A1 | 9/2020 |
| WO | 2020178885 A1 | 9/2020 |
| WO | 2020178886 A1 | 9/2020 |

OTHER PUBLICATIONS

International Search Report (ISR) (and English translation thereof) dated Apr. 23, 2019 issued in International Application No. PCT/JP2019/008032.
International Search Report (ISR) (and English translation thereof) dated May 14, 2019 issued in International Application No. PCT/JP2019/008033.
U.S. Appl. No. 17/184,784, First Named Inventor: Keisuke Ichikawa; Title: "Wide-Angle Optical System and Image Pickup Apparatus Using the Same"; filed Feb. 25, 2021.
U.S. Appl. No. 17/189,353, First Named Inventor: Keisuke Ichikawa; Title: "Wide-Angle Optical System and Image Pickup Apparatus Using the Same"; filed Mar. 2, 2021.
U.S. Appl. No. 17/190,453, First Named Inventor: Takashi Fujikura; Title: "Wide-Angle Optical System and Imaging Device Comprising Same"; filed Mar. 3, 2021.
Written Opinion dated Apr. 23, 2019 issued in International Application No. PCT/JP2019/008032.
Written Opinion dated Jun. 4, 2019, issued in International Application No. PCT/JP2019/008028.
Written Opinion dated May 14, 2019 issued in International Application No. PCT/JP2019/008033.
International Preliminary Report on Patentability (IPRP) (and English language translation thereof) dated Sep. 16, 2021 issued in International Application No. PCT/JP2019/008028 (which is an International counterpart of related U.S. Appl. No. 17/190,453).
International Preliminary Report on Patentability (IPRP) (and English language translation thereof) dated Sep. 16, 2021, issued in counterpart International Application No. PCT/JP2019/008034.

(56) References Cited

OTHER PUBLICATIONS

Japanese Office Action (and English language translation thereof) dated Apr. 20, 2022, issued in Japanese Application No. 2021-503242 (which is a counterpart of related U.S. Appl. No. 17/189,353).
Office Action (Non-Final Rejection) dated May 25, 2023, issued in related U.S. Appl. No. 17/190,453.
International Preliminary Report on Patentability (IPRP) (and English language translation thereof) dated Sep. 16, 2021, issued in counterpart International Application No. PCT/JP2019/008032 which is an International counterpart of related U.S. Appl. No. 17/184,784.
International Preliminary Report on Patentability (IPRP) (and English language translation thereof) dated Sep. 16, 2021 issued in counterpart International Application No. PCT/JP2019/008033 (which is an International counterpart of related U.S. Appl. No. 17/189,353).
U.S. Appl. No. 17/184,784, filed Mar. 2, 2021.
U.S. Appl. No. 17/189,353, filed Mar. 2, 2021; and.
U.S. Appl. No. 17/190,453, filed Mar. 3, 2021.
Chinese Office Action (and English language translation thereof) dated Feb. 14, 2022, issued in Chinese Application No. 201980056977.6 (which is a Chinese counterpart of related U.S. Appl. No. 17/189,353).
Japanese Office Action (and English language translation thereof) dated Mar. 30, 2022, issued in Japanese Application No. 2021-503240 (which is a Japanese counterpart of related U.S. Appl. No. 17/190,453).
Chinese Office Action (and English language translation thereof) dated Feb. 14, 2022, issued in Chinese Application No. 201980056267.3 (which is a counterpart of related U.S. Appl. No. 17/190,453).
International Search Report (ISR) (and English translation thereof) dated Jun. 4, 2019, issued in International Application No. PCT/JP2019/008034.
Written Opinion dated Jun. 4, 2019, issued in International Application No. PCT/JP2019/008034.
Notice of Allowance dated Apr. 10, 2024, issued in related U.S. Appl. No. 17/184,784.
Office Action (Non-Final Rejection) dated Apr. 11, 2024, issued in related U.S. Appl. No. 17/189,353.

\* cited by examiner

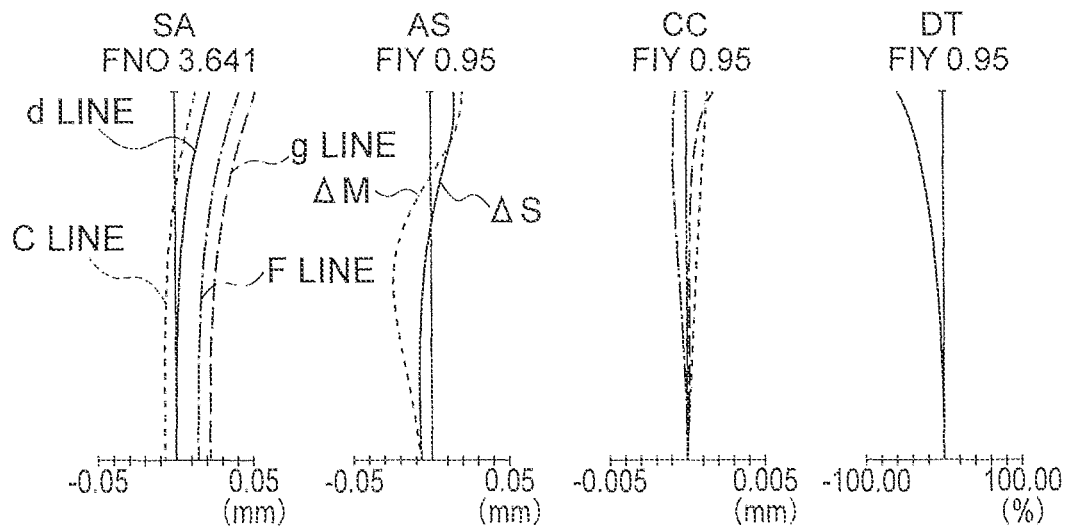
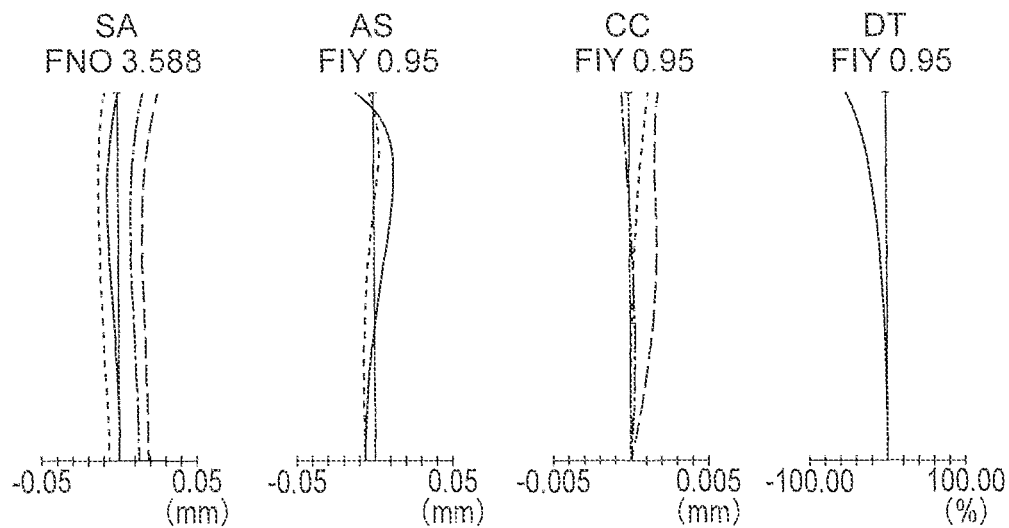

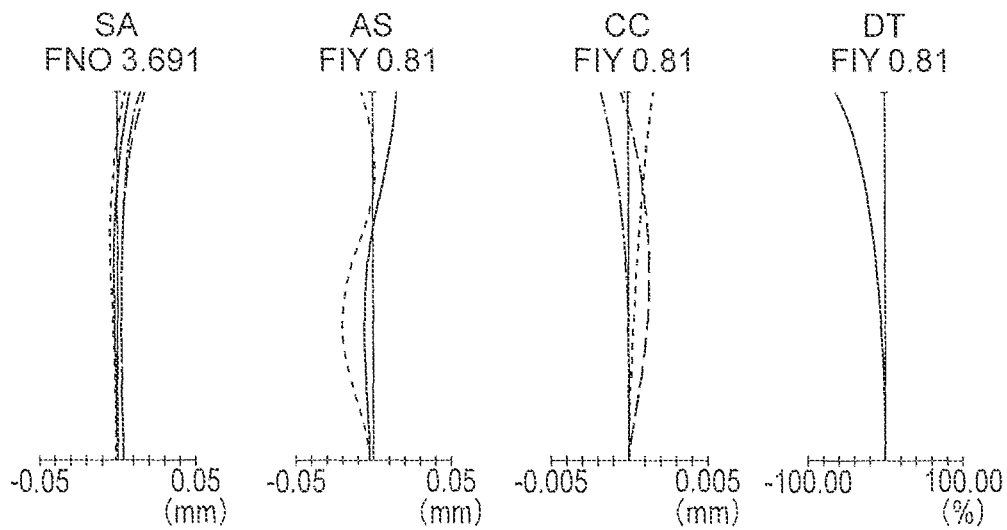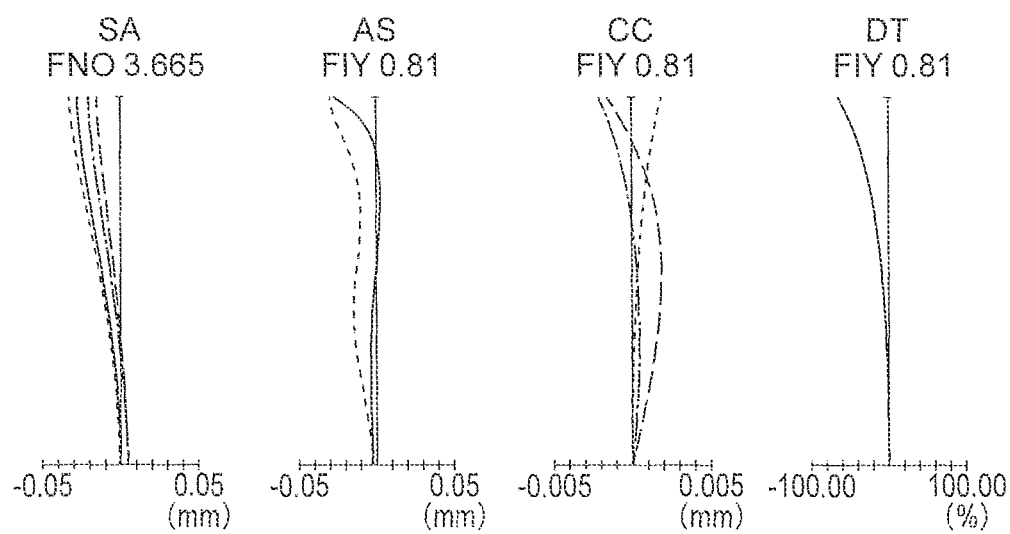

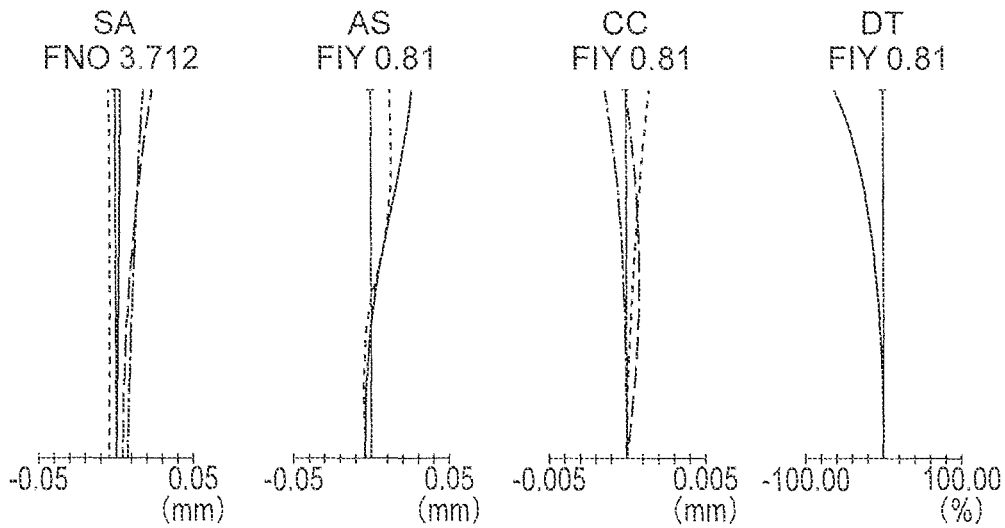
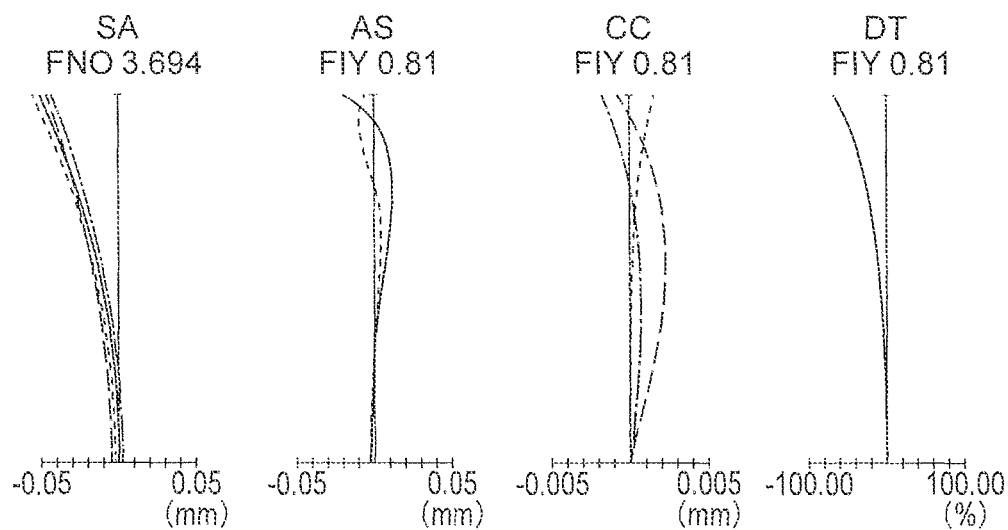

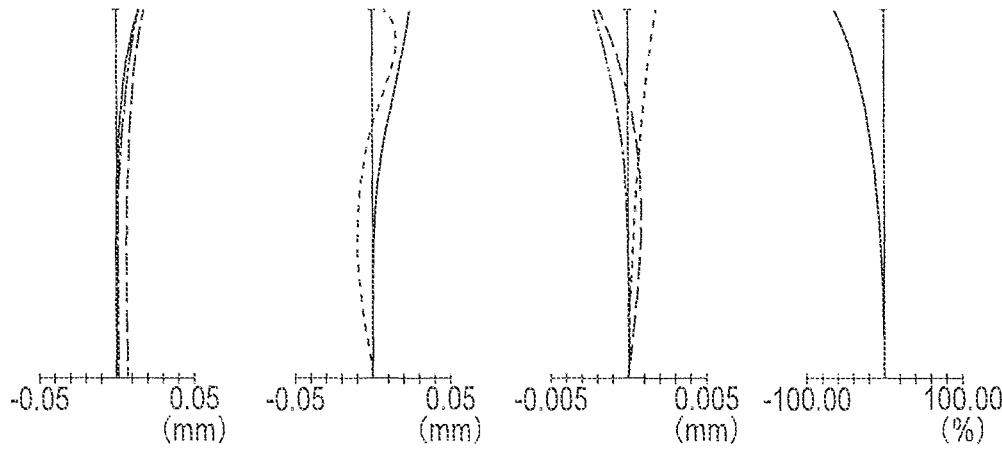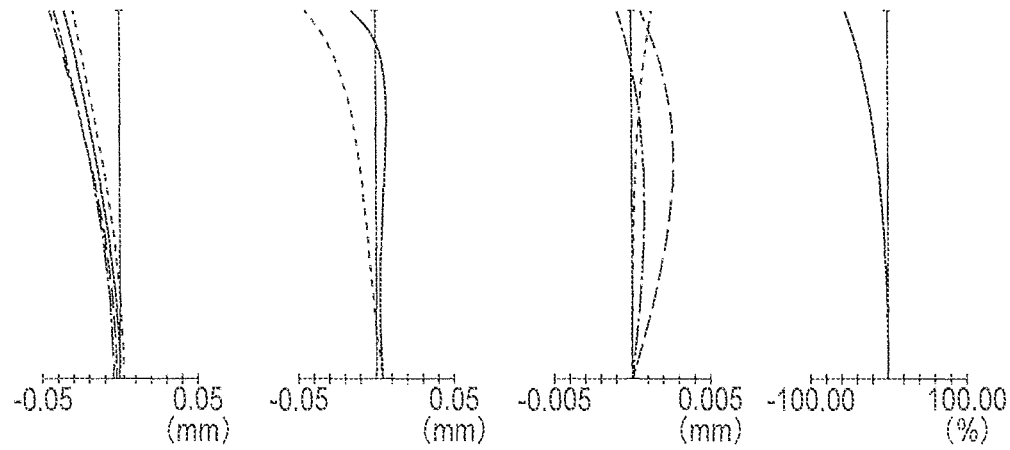

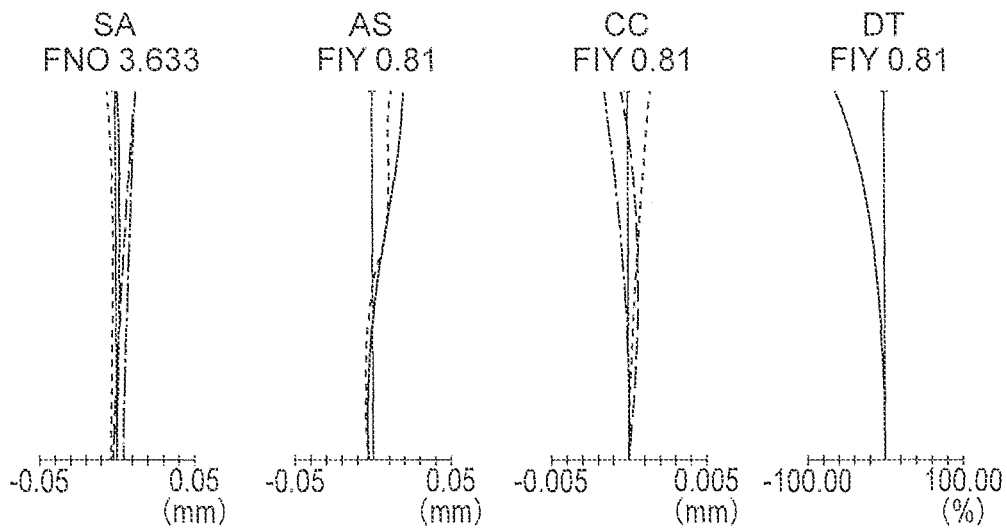
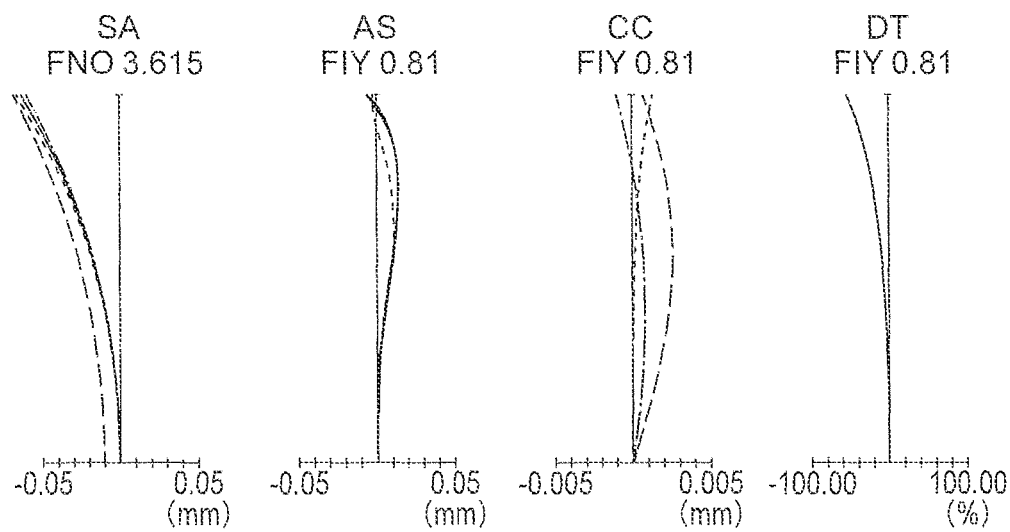

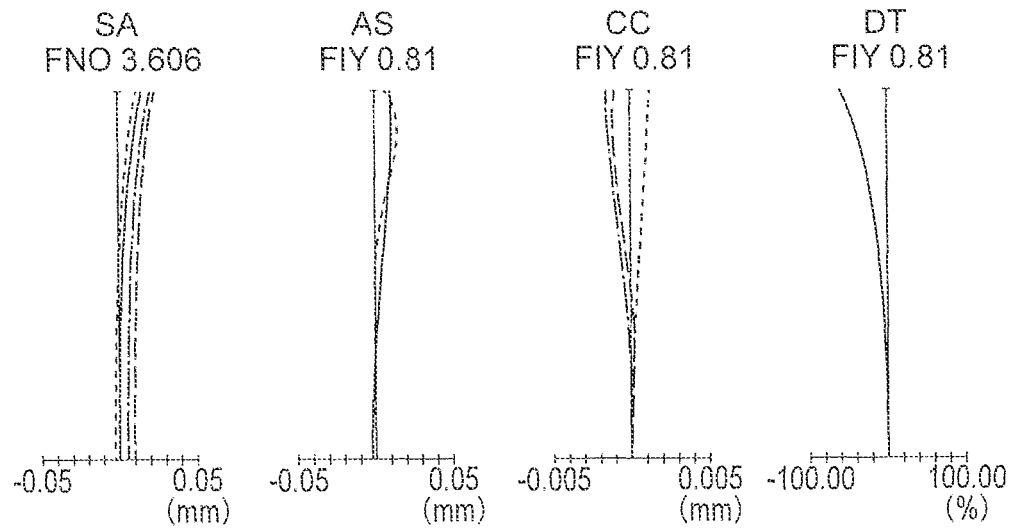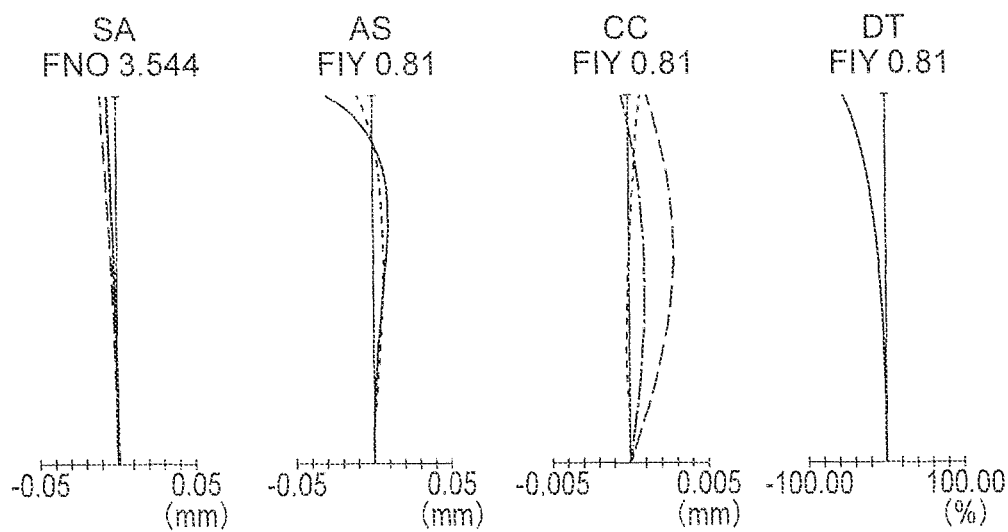

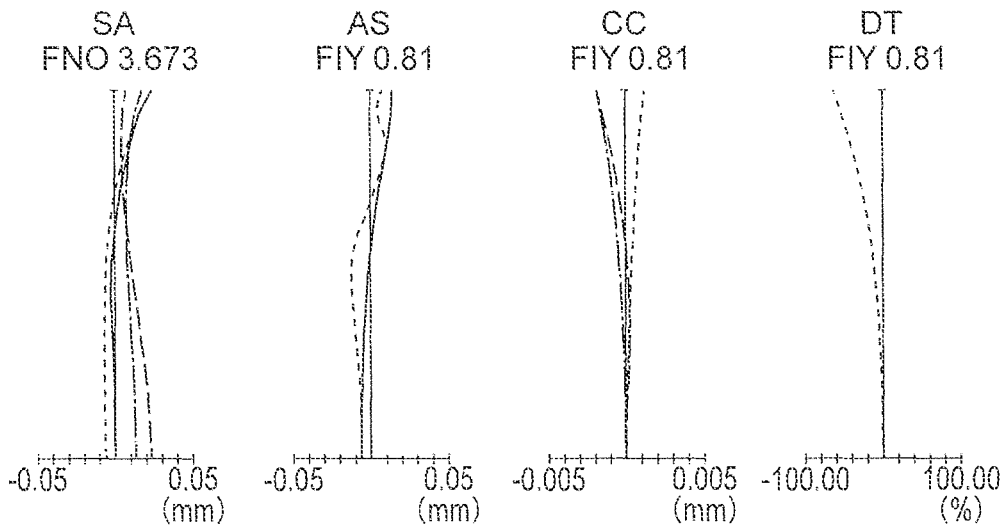
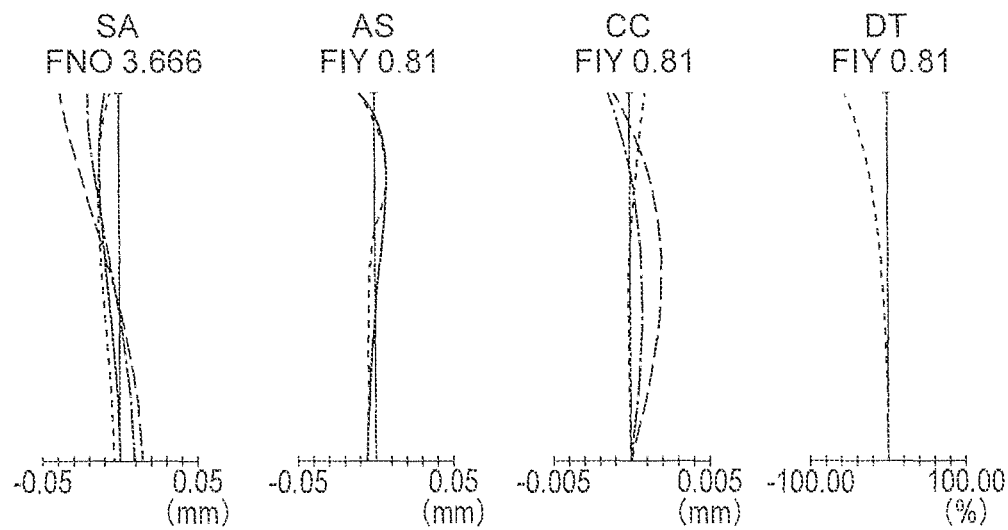

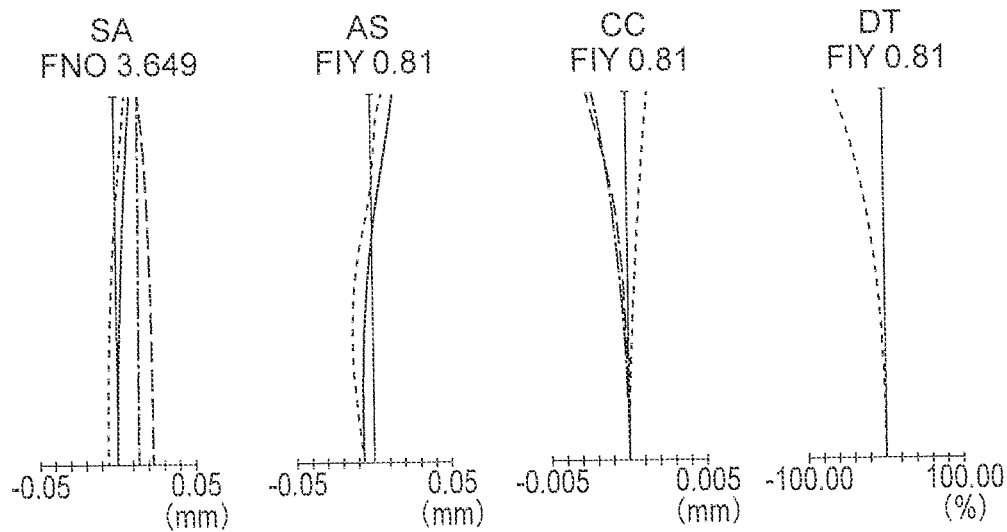
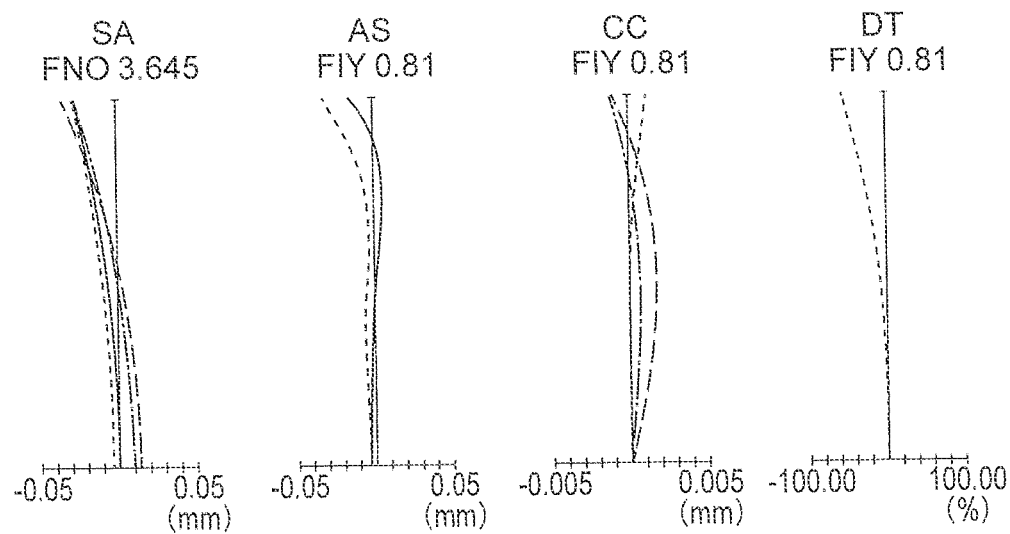

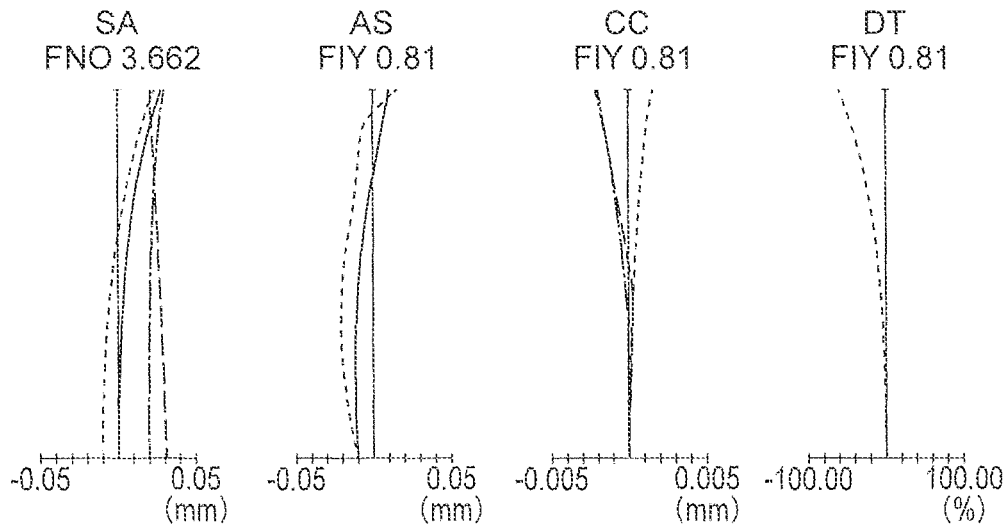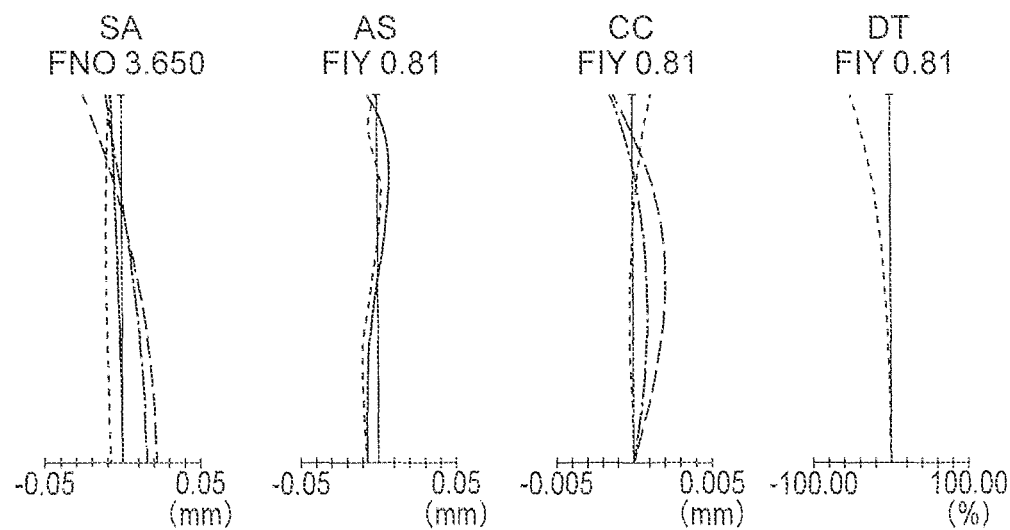

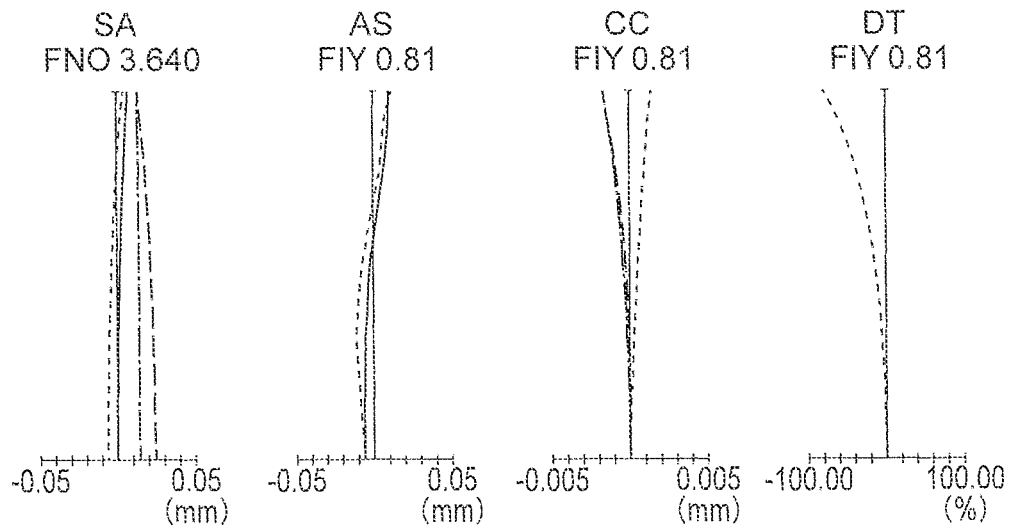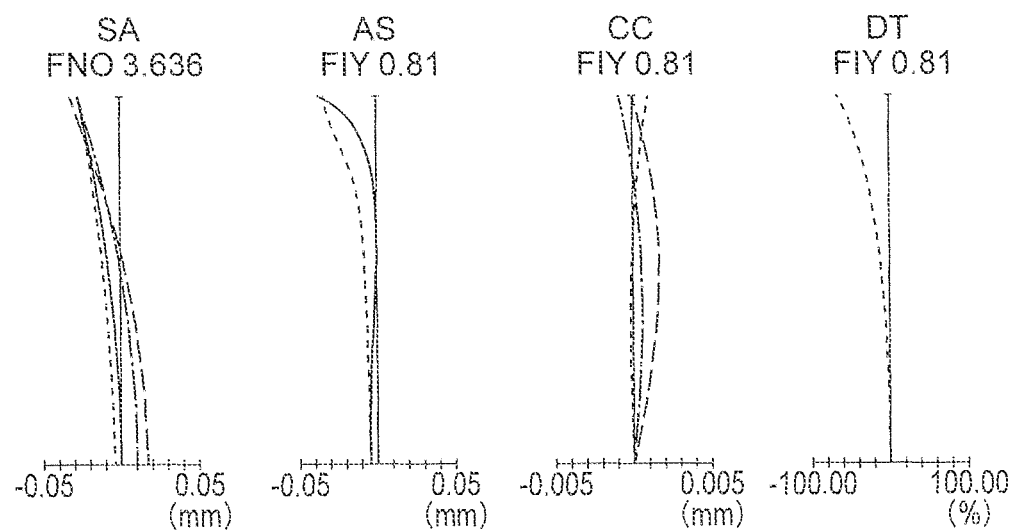

WIDE-ANGLE OPTICAL SYSTEM AND IMAGE PICKUP APPARATUS USING THE SAME

CROSS-REFERENCE TO RELATED APPLICATION

The present application is a continuation application of International Application No. PCT/JP2019/008034 filed on Mar. 1, 2019, the entire contents of which are incorporated herein by reference.

BACKGROUND

Technical Field

The present disclosure relates to a wide-angle optical system and an image pickup apparatus using the same.

Description of the Related Art

As an optical system having a wide angle of view, an objective optical system for endoscope has been known. In the objective optical system for endoscope, a wide-angle optical system with the angle of view of more than 100 degrees has been used.

In conventional endoscopes, an image sensor with a small number of pixels was used. Therefore, in an objective optical system for endoscope, an optical system with a fixed focus was used. Even when the optical system with a fixed focus was used, it was possible to cover a range of an object distance required to be observed (observation depth), by a depth of field.

However, in recent years, for improving a quality of an observed image, an image sensor with a large number of pixels has been used. In an endoscope in which the image sensor with a large number of pixels is used, a high resolution is sought even for the optical system.

When an optical system is made to have a high resolution, the depth of field becomes narrower than the required observation depth. Consequently, it becomes difficult to observe the required observation depth in a focused state. For such reasons, a need arose to impart a function of adjusting a focal position to an optical system.

An objective optical system for endoscope which enables to adjust the focal position has been known. In this objective optical system for endoscope, an inner focusing has been used for adjusting the focal position. For carrying out the inner focusing, an actuator is provided around an optical system.

An optical unit, for instance, includes an optical system and an actuator. In an endoscope, it is necessary to seal the optical unit. Moreover, the angle of view is 140° or more, and there are restrictions on a size and an output of the actuator. Therefore, in the focal-position adjustment, it is difficult to move the optical system. A light-weight and space-saving inner focusing is necessary.

Objective optical systems for endoscope in which the inner focusing is used, have been disclosed in International Unexamined Patent Application Publication No. 2014/129089 and International Unexamined Patent Application Publication No. 2016/067838.

In an objective optical system for an endoscope, cases in which a filter, a prism, or a prism and a filter is/are disposed between a surface located nearest to an object in the optical system and an imaging position, have been increasing. The filter and the prism are optical elements not having an imaging function.

For securing a space for disposing an optical element not having the imaging function, a back focus of an optical system is made long. However, as the back focus is made long, a light-ray height becomes high. Consequently, it becomes difficult to reduce a size of an optical unit.

SUMMARY

A wide-angle optical system according to at least some embodiments of the present disclosure is a wide-angle optical system having a lens component, the lens component has a plurality of optical surfaces, and in the lens component, two optical surfaces are in contact with air and at least one optical surface is a curved surface, includes in order from an object side:

a first lens unit having a negative refractive power,
a second lens unit having a positive refractive power, and
a third lens unit having a positive refractive power, wherein at the time of carrying out a focal-position adjustment from a far point to a near point, the second lens unit is moved from a first position toward a second position, the first position is a position at which a distance between the first lens unit and the second lens unit becomes the minimum, and the second position is a position at which a distance between the second lens unit and the third lens unit becomes the minimum, the third lens unit has not less than nine refractive surfaces, and includes a positive single lens on an image side of a cemented surface Sc having a negative refractive power nearest to an image in the third lens unit, and has a plurality of refractive surfaces having a negative refractive power on the object side of the cemented surface Sc, and the third lens unit has at least one refractive surface Sp having a positive refractive power which satisfies following conditional expression (1), on the object side of two surfaces located on the image side, out of the plurality of refractive surfaces having a negative refractive power:

$$0.02 < fL/Rsp < 1.20 \qquad (1)$$

where,

Rsp denotes a radius of curvature of the refractive surface Sp having a positive refractive power, and fL denotes a focal length of the wide-angle optical system at the first position.

Moreover, an image pickup apparatus of the present disclosure includes:

an optical system, and
an image sensor which is disposed on an image plane, wherein the image sensor has an image pickup surface, and converts an image formed on the image pickup surface by the optical system to an electric signal, and the optical system is the abovementioned wide-angle optical system.

BRIEF DESCRIPTION OF THE DRAWINGS

FIG. 11A, FIG. 11B, FIG. 11C, FIG. 11D, FIG. 11E, FIG. 11F, FIG. 11G, and FIG. 11H are aberration diagrams of the wide-angle optical system of the example 1;

FIG. 12A, FIG. 12B, FIG. 12C, FIG. 12D, FIG. 12E, FIG. 12F, FIG. 12G, and FIG. 12H are aberration diagrams of the wide-angle optical system of the example 2;

FIG. 13A, FIG. 13B, FIG. 13C, FIG. 13D, FIG. 13E, FIG. 13F, FIG. 13G, and FIG. 13H are aberration diagrams of the wide-angle optical system of the example 3;

FIG. 14A, FIG. 14B, FIG. 14C, FIG. 14D, FIG. 14E, FIG. 14F, FIG. 14G, and FIG. 14H are aberration diagrams of the wide-angle optical system of the example 4;

FIG. 15A, FIG. 15B, FIG. 15C, FIG. 15D, FIG. 15E, FIG. 15F, FIG. 15G, and FIG. 15H are aberration diagrams of the wide-angle optical system of the example 5;

FIG. 16A, FIG. 16B, FIG. 16C, FIG. 16D, FIG. 16E, FIG. 16F, FIG. 16G, and FIG. 16H are aberration diagrams of the wide-angle optical system of the example 6;

FIG. 17A, FIG. 17B, FIG. 17C, FIG. 17D, FIG. 17E, FIG. 17F, FIG. 17G, and FIG. 17H are aberration diagrams of the wide-angle optical system of the example 7;

FIG. 18A, FIG. 18B, FIG. 18C, FIG. 18D, FIG. 18E, FIG. 18F, FIG. 18G, and FIG. 18H are aberration diagrams of the wide-angle optical system of the example 8;

FIG. 19A, FIG. 19B, FIG. 19C, FIG. 19D, FIG. 19E, FIG. 19F, FIG. 19G, and FIG. 19H are aberration diagrams of the wide-angle optical system of the example 9;

FIG. 20A, FIG. 20B, FIG. 20C, FIG. 20D, FIG. 20E, FIG. 20F, FIG. 20G, and FIG. 20H are aberration diagrams of the wide-angle optical system of the example 10;

DETAILED DESCRIPTION

Figure 1A:
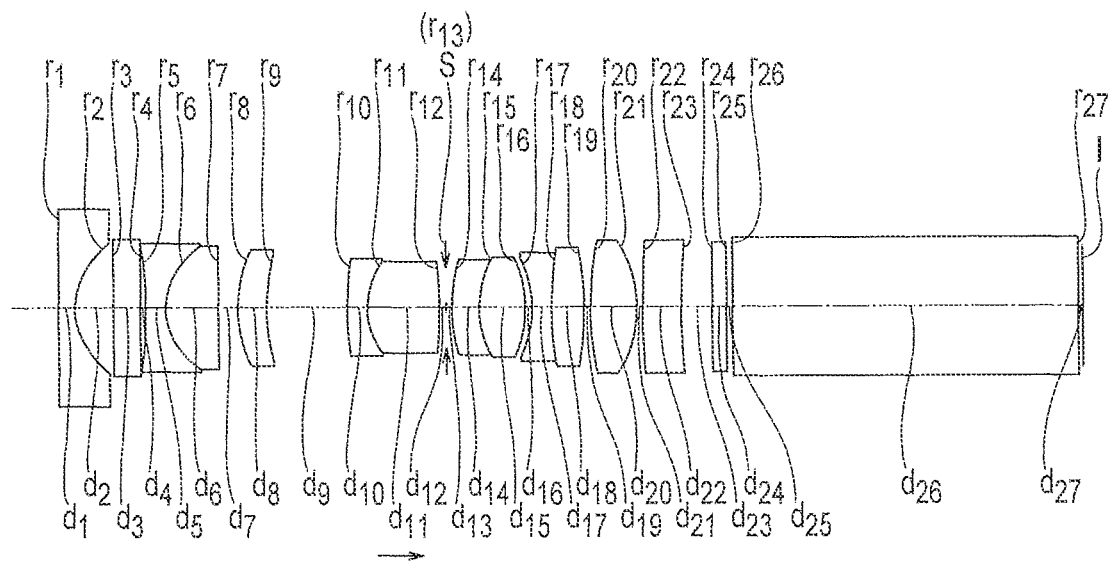
FIG. 1A and FIG. 1B are lens cross-sectional views of a wide-angle optical system of an example 1.
Figure 1B:
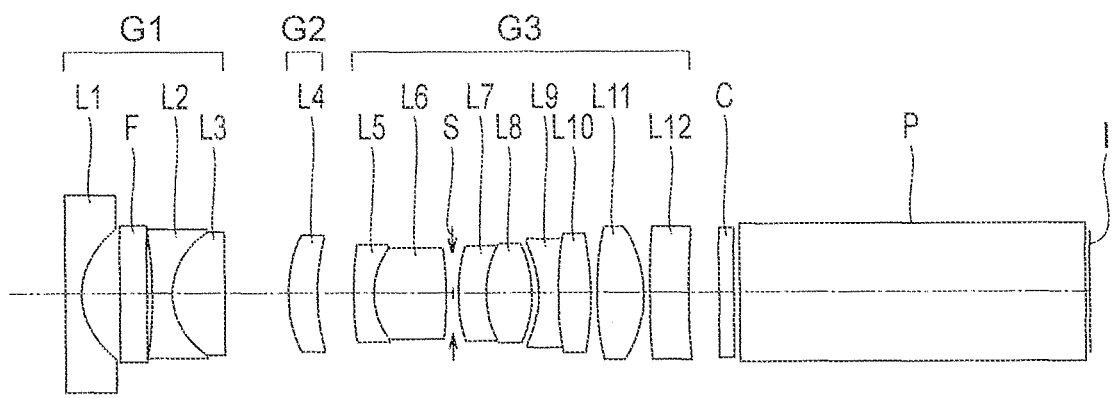
Figure 2A:
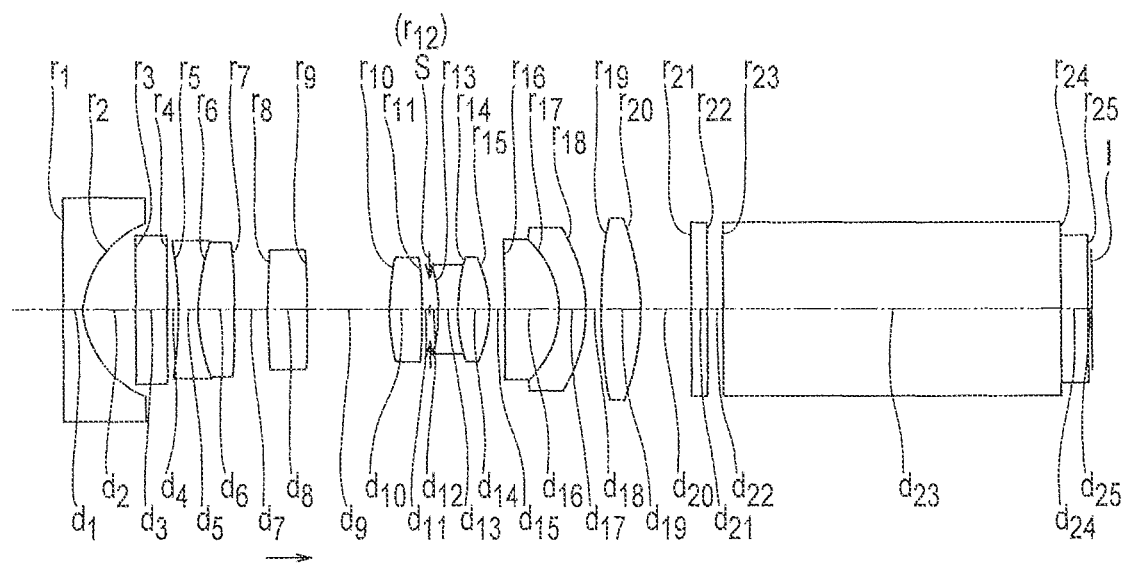
FIG. 2A and FIG. 2B are lens cross-sectional views of a wide-angle optical system of an example 2.
Figure 2B:
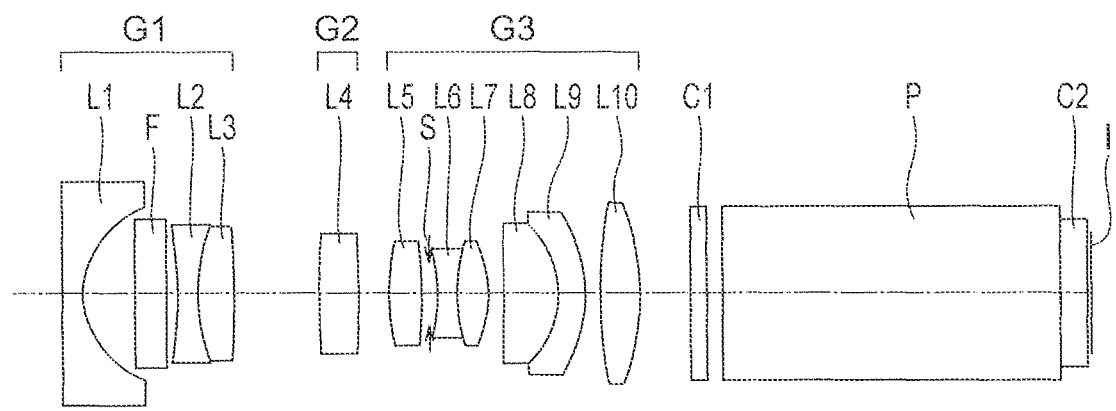
Figure 3A:
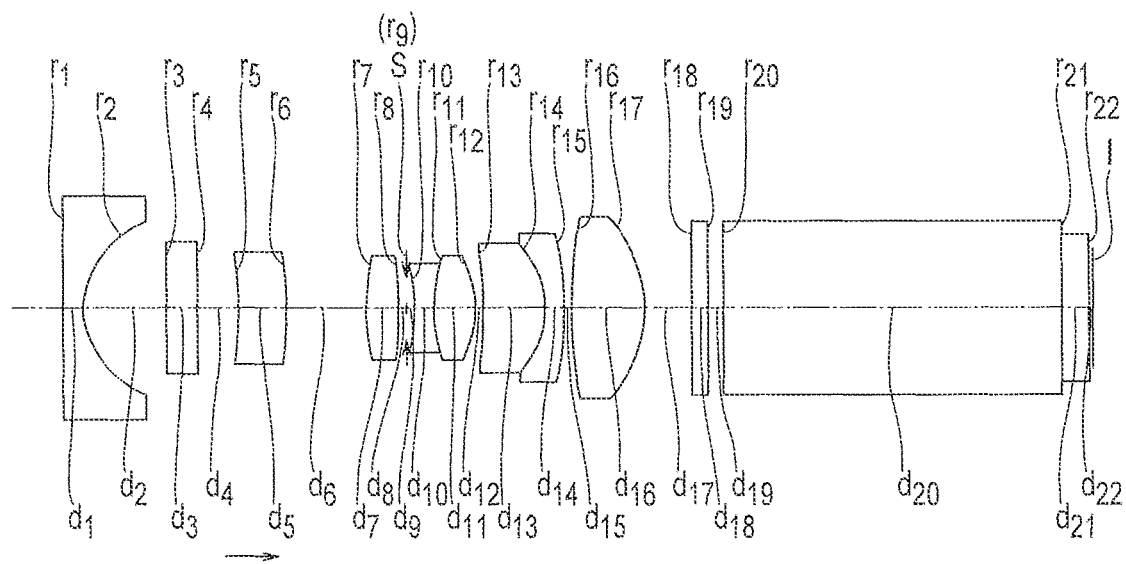
FIG. 3A and FIG. 3B are lens cross-sectional views of a wide-angle optical system of an example 3.
Figure 3B:
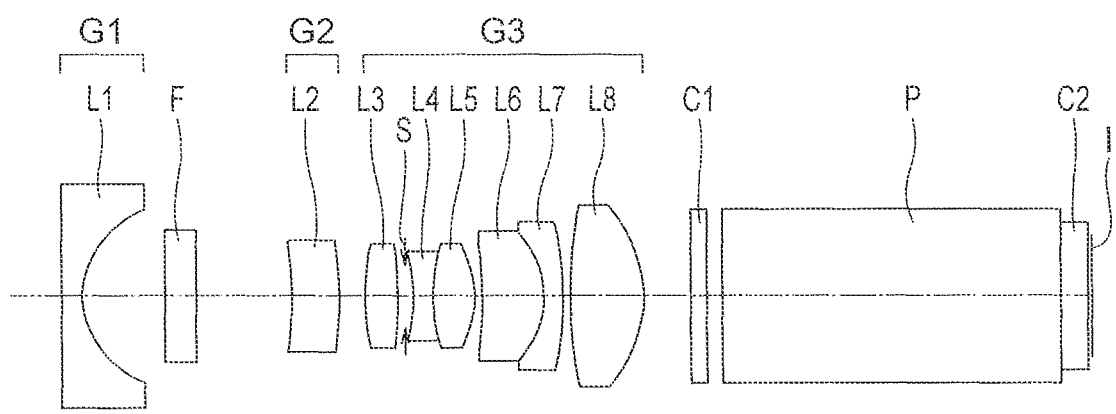
Figure 4A:
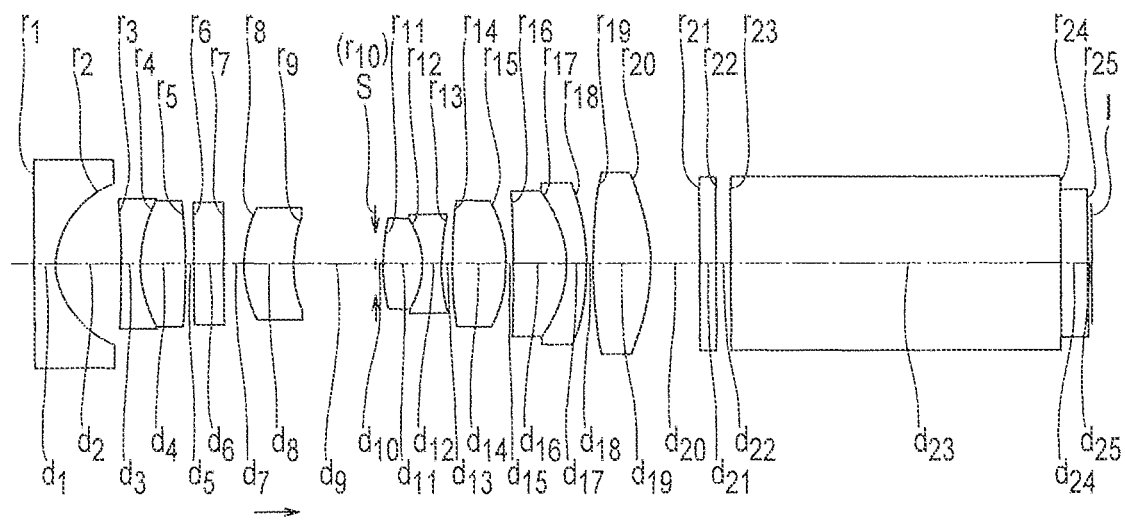
FIG. 4A and FIG. 4B are lens cross-sectional views of a wide-angle optical system of an example 4.
Figure 4B:
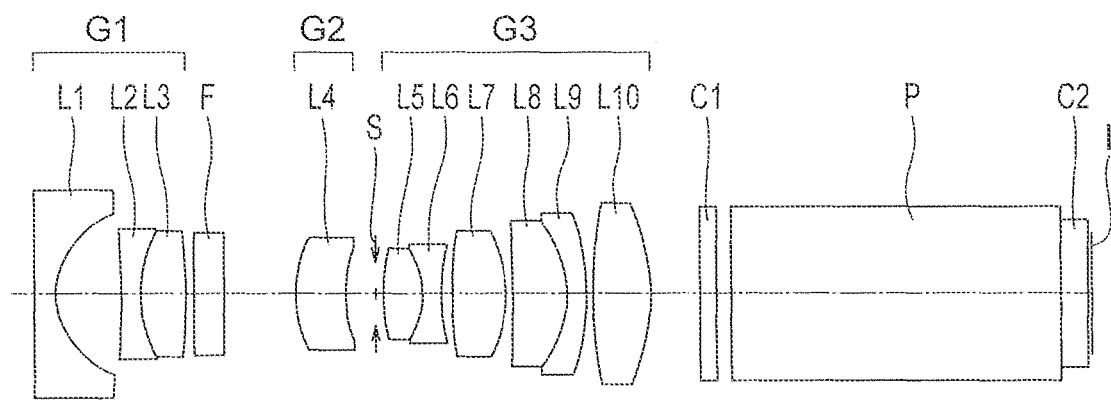
Figure 5A:
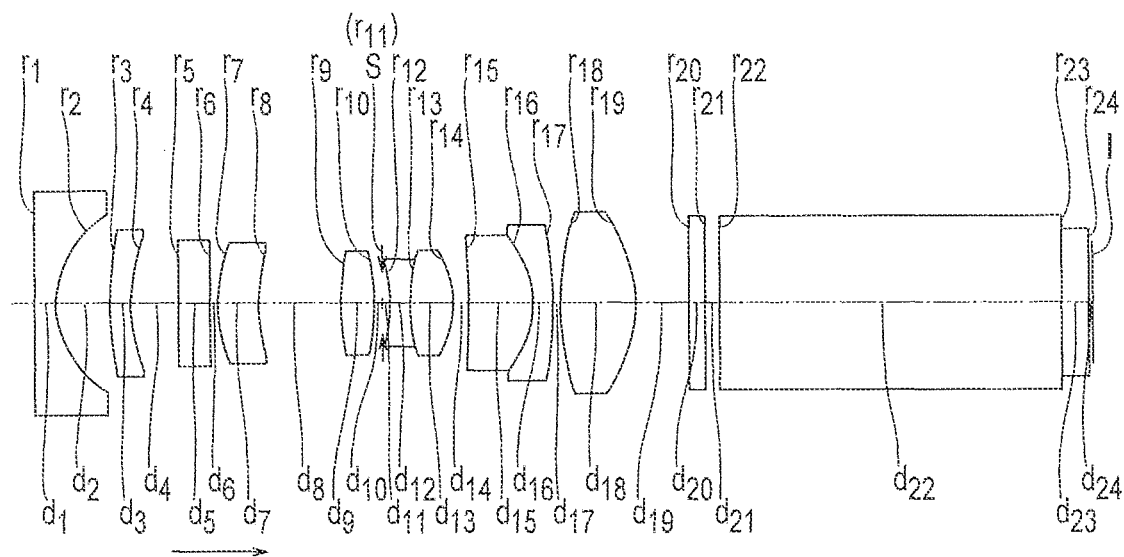
FIG. 5A and FIG. 5B are lens cross-sectional views of a wide-angle optical system of an example 5.
Figure 5B:
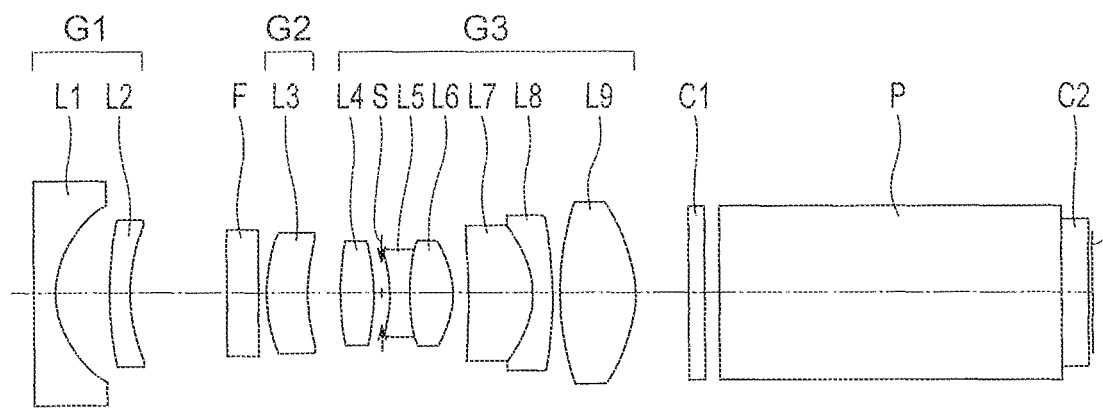
Figure 6A:
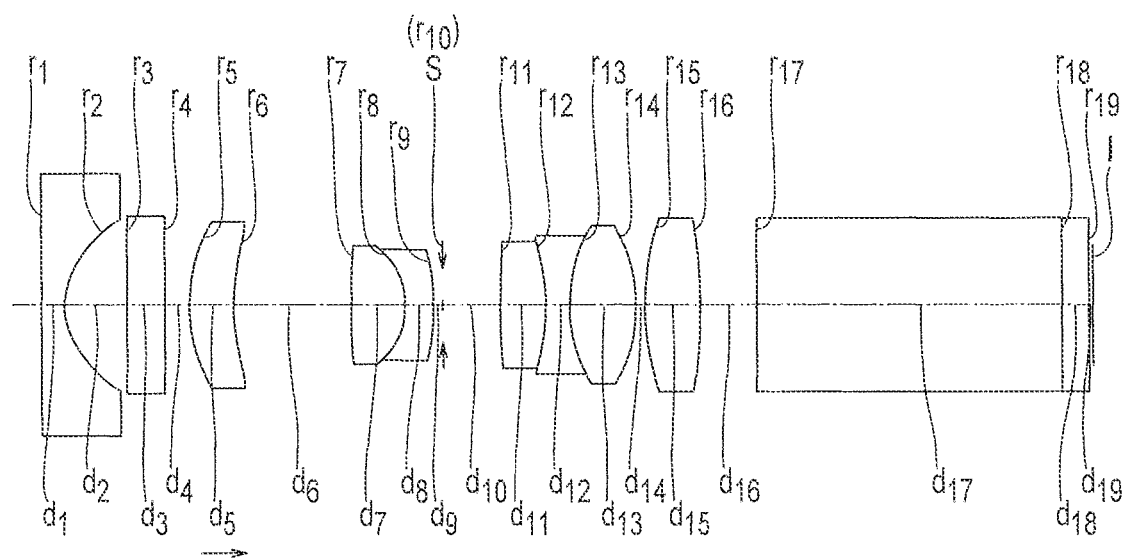
FIG. 6A and FIG. 6B are lens cross-sectional views of a wide-angle optical system of an example 6.
Figure 6B:
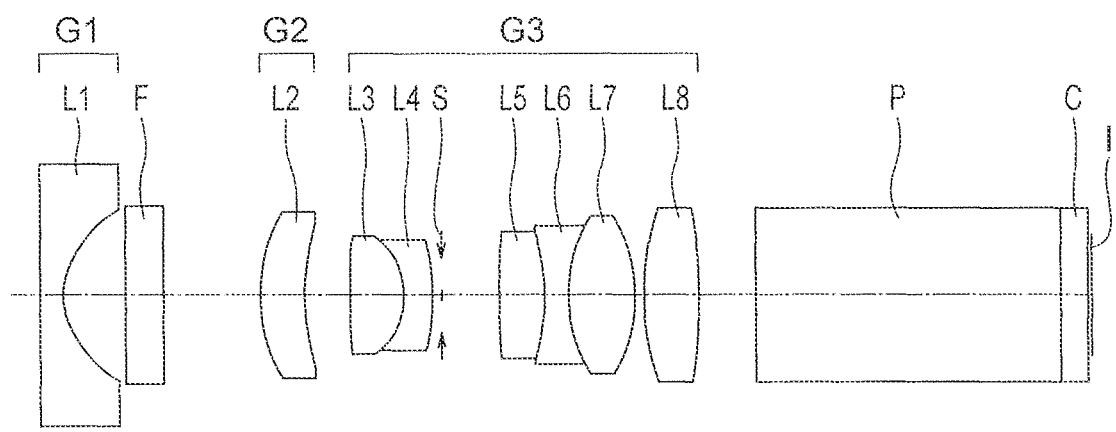
Figure 7A:
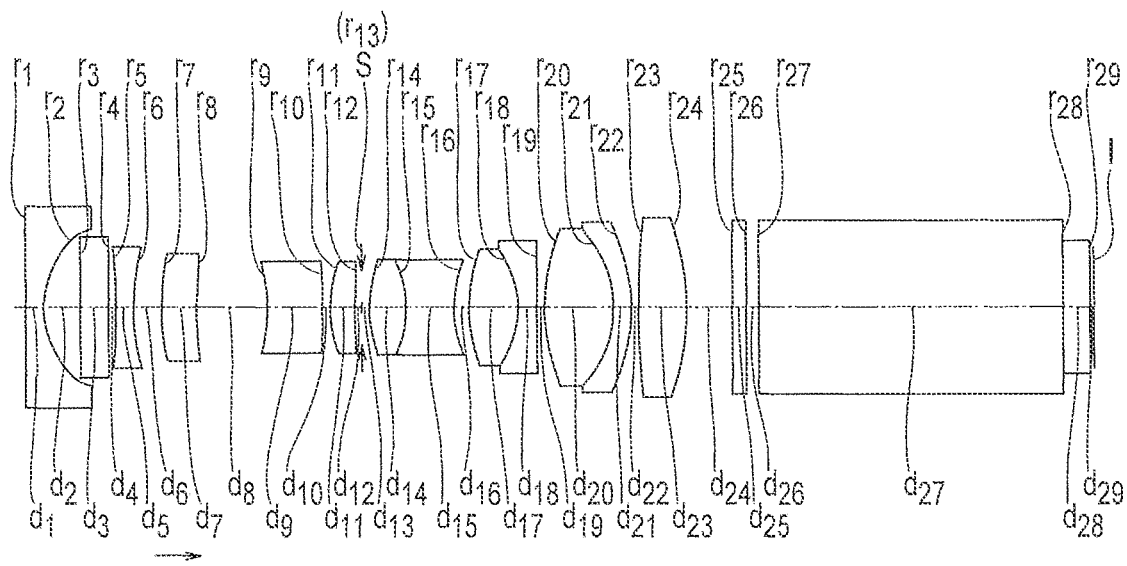
FIG. 7A and FIG. 7B are lens cross-sectional views of a wide-angle optical system of an example 7.
Figure 7B:
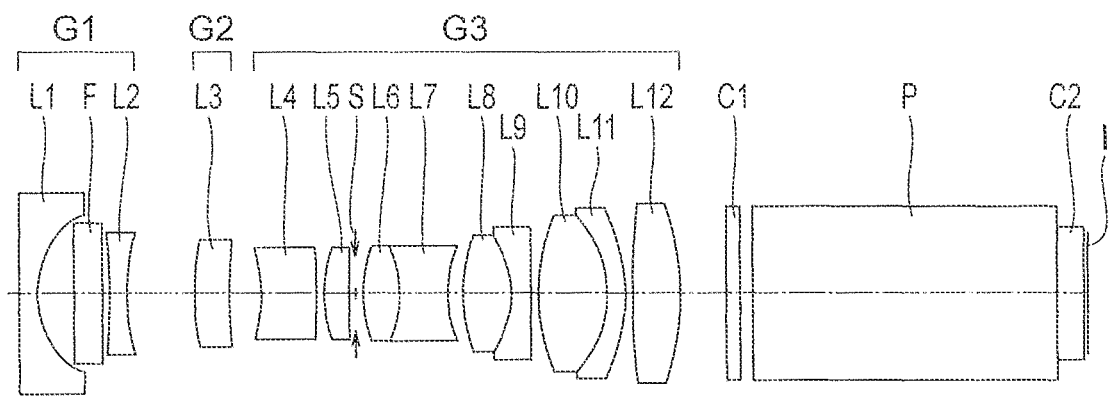
Figure 8A:
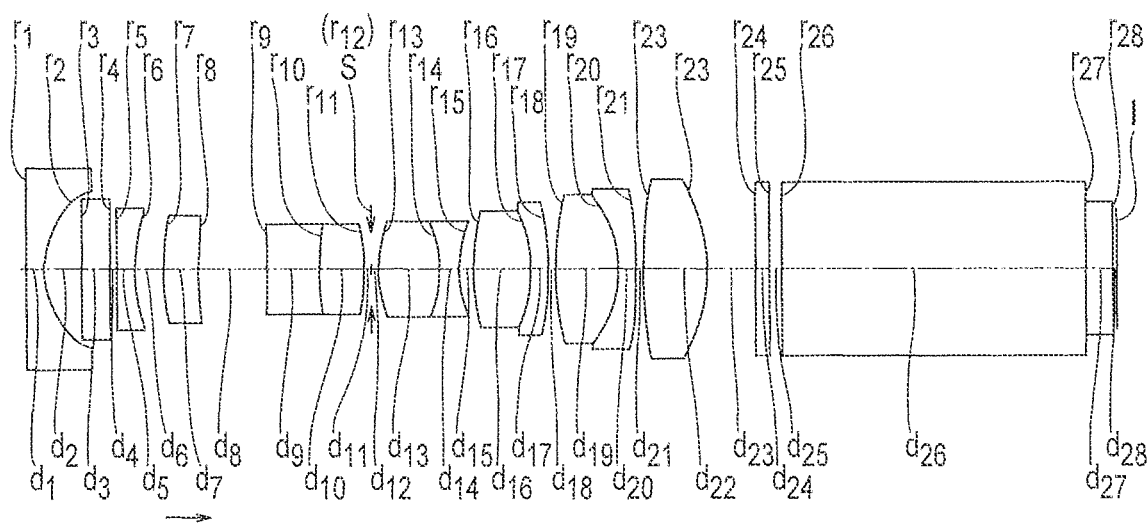
FIG. 8A and FIG. 8B are lens cross-sectional views of a wide-angle optical system of an example 8.
Figure 8B:
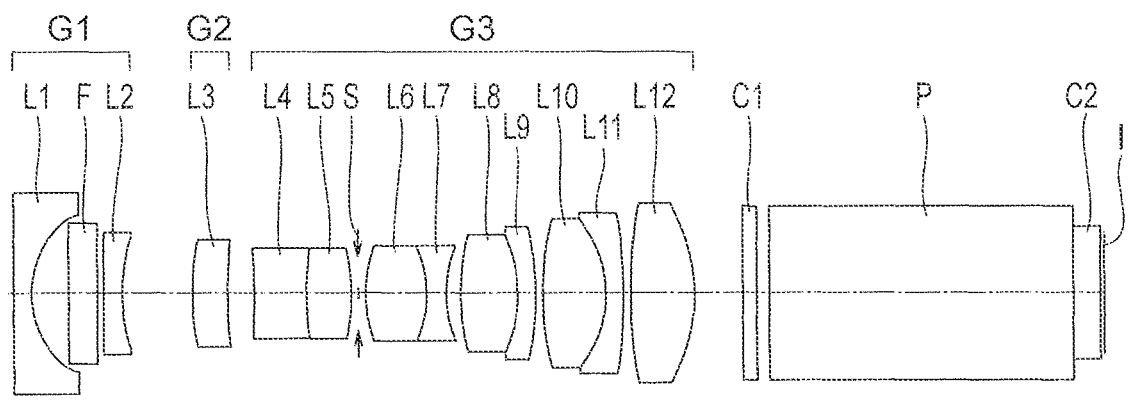
Figure 9A:
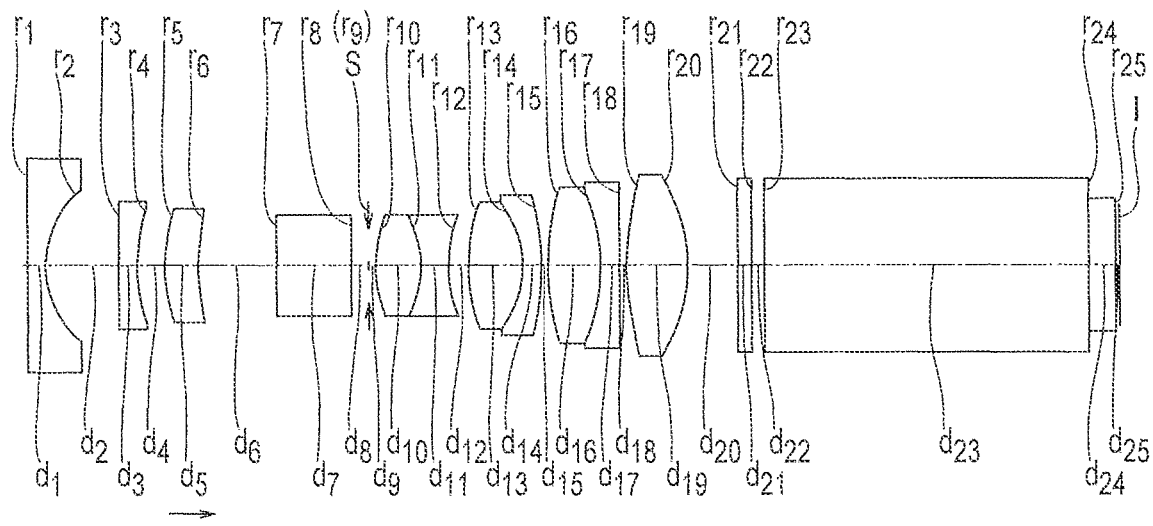
FIG. 9A and FIG. 9B are lens cross-sectional views of a wide-angle optical system of an example 9.
Figure 9B:
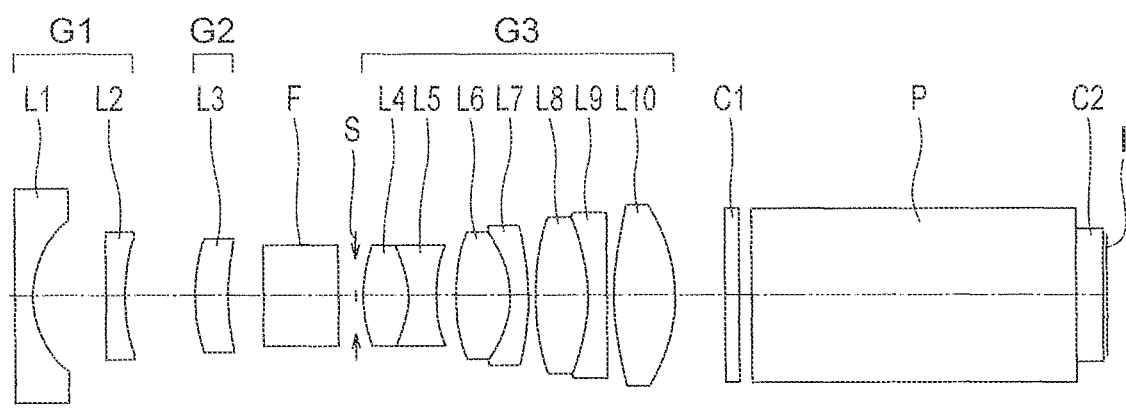
Figure 10A:
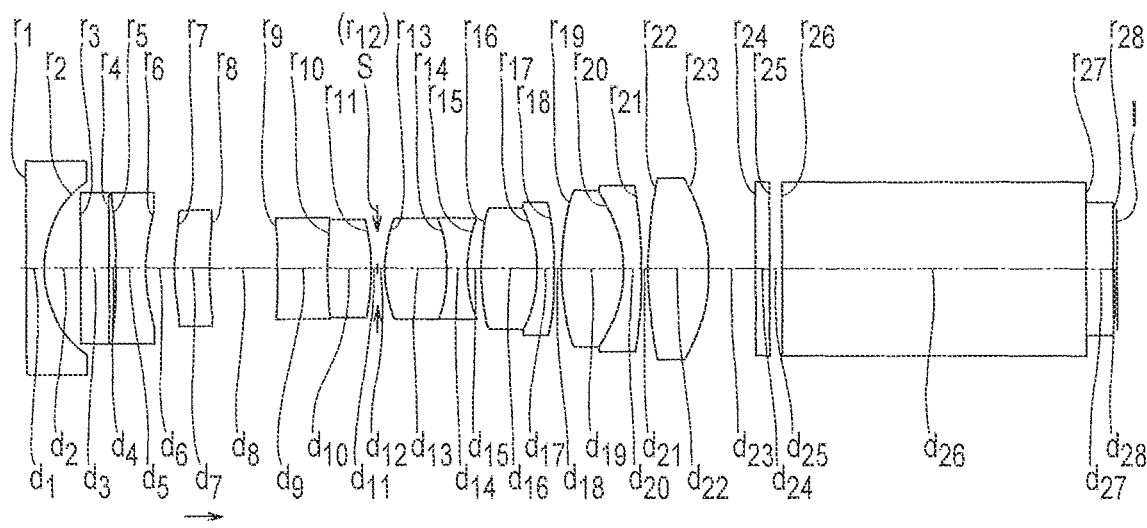
FIG. 10A and FIG. 10B are lens cross-sectional views of a wide-angle optical system of an example 10.
Figure 10B:
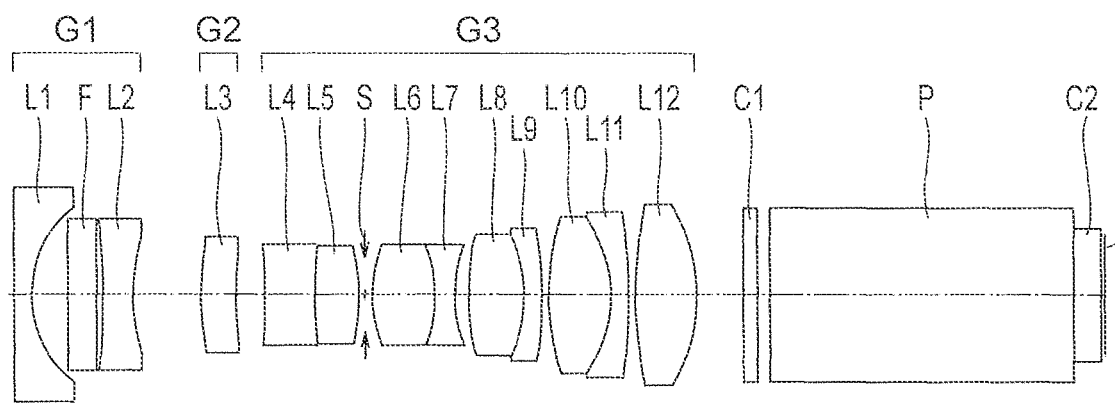

Prior to the explanation of examples, action and effect of embodiments according to certain aspects of the present disclosure will be described below. In the explanation of the action and effect of the embodiments concretely, the explanation will be made by citing concrete examples. However, similar to a case of the examples to be described later, aspects exemplified thereof are only some of the aspects included in the present disclosure, and there exists a large number of variations in these aspects. Consequently, the present disclosure is not restricted to the aspects that will be exemplified.

A wide-angle optical system of the present embodiment is a wide-angle optical system having a lens component. The lens component has a plurality of optical surfaces, in the lens component, two optical surfaces are in contact with air, and at least one optical surface is a curved surface. The wide-angle optical system includes in order from an object side, a first lens unit having a negative refractive power, a second lens unit having a positive refractive power, and a third lens unit having a positive refractive power. At the time of carrying out a focal-position adjustment from a far point to a near point, the second lens unit is moved from a first position toward a second position. The first position is a position at which a distance between the first lens unit and the second lens unit becomes the minimum, and the second position is a position at which a distance between the second lens unit and the third lens unit becomes the minimum. The third lens unit has not less than nine refractive surfaces, and includes a positive single lens on an image side of a cemented surface Sc having a negative refractive power nearest to an image in the third lens unit, and has a plurality of refractive surfaces having a negative refractive power on the object side of the cemented surface Sc. The third lens unit has at least one refractive surface Sp having a positive refractive power which satisfies following conditional expression (1), on the object side of two surfaces located on the image side, out of the plurality of refractive surfaces having a negative refractive power:

$$0.02 < fL/Rsp < 1.20 \tag{1}$$

where,

Rsp denotes a radius of curvature of the refractive surface Sp having a positive refractive power, and fL denotes a focal length of the wide-angle optical system at the first position.

The wide-angle optical system of the present embodiment, for instance, is about a wide-angle optical system with an angle of view of more than 100 degrees. In recent years, with the debut of a high-resolution monitor and the like, regarding an image quality at the time of observation, a high image quality is being sought. The wide-angle optical system of the present embodiment is a wide-angle optical system which is capable of dealing with such requirement.

Moreover, the wide-angle optical system of the present embodiment is an optical system in which an inner focusing is used. Therefore, an actuator is disposed around an inner-focusing lens. In the wide-angle optical system of the present embodiment, even with the actuator disposed around the optical system, an outer diameter of the overall optical system is small. The wide-angle optical system of the present embodiment, while being an optical system having a wide angle of view, is an optical system in which a light-ray height is suppressed to be low over a long range of a central portion of the optical system.

The wide-angle optical system of the present embodiment is a wide-angle optical system having the lens component. The lens component has the plurality of optical surfaces. In the lens component, the two optical surfaces are in contact with air, and at least one optical surface is a curved surface. The lens component includes a single lens and a cemented lens for example.

Moreover, in the lens component, a lens and a plane parallel plate may have been cemented. In this case, one optical surface in contact with air is a lens surface, and the other optical surface in contact with air is a flat surface. A lens component in which a single lens and a plane parallel plate are cemented, is to be deemed as a single lens. A lens component in which a cemented lens and a plane parallel plate are cemented, is to be deemed as a cemented lens.

Moreover, a planoconvex lens and a planoconcave lens may have been cemented. In this case, a cemented surface is a curved surface and an optical surface in contact with air is a flat surface.

The surface on the object side of the lens component, out of the two optical surfaces in contact with air, is an optical surface located on the object side. A surface on an image side of the lens component, out of the two optical surfaces in contact with air, is an optical surface located on the image side. In a case in which the lens component is a cemented lens, a cemented surface is located between the surface on the object side and the surface on the image side.

The wide-angle optical system of the present embodiment includes in order from the object side, the first lens unit having a negative refractive power, the second lens unit having a positive refractive power, and the third lens unit having a positive refractive power. At the time of carrying out the focal-position adjustment from the far point to the near point, the second lens unit is moved from the first position toward the second position. The movement from the first position toward the second position is a movement in a direction in which the distance between the first lens unit and the second lens unit widens, and is a movement in a direction in which the distance between the second lens unit and the third lens unit shortens.

The first position is a position at which the distance between the first lens unit and the second lens unit becomes the minimum. At the first position, the second lens unit is located nearest to the object in a range of movement. At the first position, it is possible to focus to an object located at a far point.

The second position is a position at which the distance between the second lens unit and the third lens unit becomes the minimum. At the second position, the second lens unit is located nearest to an image in a range of movement. At the second position, it is possible to focus to an object located at a near point.

The second lens unit is moved for the focal-position adjustment. An actuator is used for moving the second lens unit. The actuator is disposed near the second lens unit or near the third lens unit. Therefore, it is necessary to provide a space for disposing the actuator near the second lens unit or near the third lens unit.

The third lens unit has not less than nine refractive surfaces, and includes the positive single lens on the image side of the cemented surface Sc having a negative refractive power nearest to the image in the third lens unit, and has the plurality of refractive surfaces having a negative refractive power on the object side of the cemented surface Sc.

In the wide-angle optical system of the present embodiment, adjustment of the focal position is carried out by moving the second lens unit. Therefore, it is preferable to suppress a light-ray height on the object side of the third lens unit to be low. However, it is necessary to secure adequately the back focus as well.

When an attempt is made to secure a long back focus in a wide-angle optical system, the light-ray height in the optical system tends to become high. As mentioned above, the second lens unit is located on the object side of the third lens unit. Accordingly, it is preferable to be able to make the light-ray height low on the object side of the third lens unit. However, when an attempt is made to secure a long back focus, the light-ray height is to be made high once on the object side of the third lens unit, and light rays are to be converged on the image side.

Therefore, in the wide-angle optical system of the present embodiment, the refractive surfaces are provided in large number in the third lens unit. Specifically, not less than nine refractive surfaces are disposed in the third lens unit. By making such arrangement, a rise in the light-ray height in the third lens unit is suppressed.

In the third lens unit, the positive single lens is disposed on the image side of the cemented surface Sc having a negative refractive power nearest to the image. By making such arrangement, the rise in the light-ray height on the object side of the third lens unit is suppressed.

Moreover, in the third lens unit, the plurality of refractive surfaces having a negative refractive power is disposed on the object side of the cemented surface Sc. By making such arrangement, the rise in the light-ray height is suppressed by distributing the negative refractive power of the third lens unit to the plurality of refractive surfaces.

The third lens unit has at least one refractive surface Sp having a positive refractive power which satisfies conditional expression (1), on the object side of two surfaces located on the image side out of the plurality of refractive surfaces having a negative refractive power. The cemented surface Sc has an effect of suppressing the rise in the light-ray height.

By using the refractive surface Sp with the positive single lens and the plurality of refractive surfaces having a negative refractive power, it is possible to prevent from rising a light ray on the object side of the third lens unit. As a result, it is possible to lower the light-ray height over a wide range from the object side of the second lens unit up to a vicinity of a center of the third lens unit (hereinafter, referred to as 'predetermined range'), and furthermore, it is possible to secure an adequate back focus.

In a case in which a value exceeds an upper limit value of conditional expression (1), correction of a spherical aberration, correction of a coma, and correction of an astigmatism become difficult. In a case in which the value falls below a lower limit value of conditional expression (1), the light-ray height is susceptible to become high in the predetermined range or securing the back focus adequately becomes difficult.

It is preferable that following conditional expression (1') be satisfied instead of conditional expression (1).

$$0.05 < fL/Rsp < 0.80 \quad (1')$$

Moreover, it is more preferable that following conditional expression (1") be satisfied instead of conditional expression (1).

$$0.08 < fL/Rsp < 0.50 \quad (1'')$$

In the wide-angle optical system of the present embodiment, it is preferable that the refractive surface Sp having a positive refractive power satisfy following conditional expression (2):

$$1.5 < \Sigma Dpc/fL < 10.0 \quad (2)$$

where,
ΣDpc denotes a distance on an optical axis from the refractive surface Sp having a positive refractive power up to the cemented surface Sc having a negative refractive power, and fL denotes the focal length of the wide-angle optical system at the first position.

It is preferable that the distance on the optical axis from the refractive surface Sp having a positive refractive power up to the cemented surface Sc having a negative refractive power be as long as possible. By making such arrangement, it becomes easy to realize suppressing the rise in the light-ray height, securing the long back focus, and favorable aberration correction in a balanced manner.

In a case in which a value exceeds an upper limit value of conditional expression (2), an overall length of the optical system is susceptible to become long. In a case in which the value falls below a lower limit value of conditional expression (2), suppressing the rise in the light-ray height, securing the long back focus, and favorable aberration correction are not realized in a balanced manner.

It is preferable that following conditional expression (2') be satisfied instead of conditional expression (2).

$$2.0<\Sigma Dpc/fL<8.0 \qquad (2')$$

Moreover, it is more preferable that following conditional expression (2") be satisfied instead of conditional expression (2).

$$2.5<\Sigma Dpc/fL<6.0 \qquad (2'')$$

In the wide-angle optical system of the present embodiment, it is preferable that following conditional expression (3) be satisfied:

$$2.0<\Sigma D3/fL<15.0 \qquad (3)$$

where,
ΣD3 denotes a distance on the optical axis from a lens surface nearest to an object up to a lens surface nearest to the image in the third lens unit, and fL denotes the focal length of the wide-angle optical system at the first position.

In a case in which a value exceeds an upper limit value of conditional expression (3), either the overall length of the optical system is susceptible to become long or securing an adequate back focus becomes difficult. In a case in which the value falls below a lower limit value of conditional expression (3), correction of the spherical aberration, correction of the coma, and correction of the astigmatism become difficult.

It is preferable that following conditional expression (3') be satisfied instead of conditional expression (3).

$$3.0<\Sigma D3/fL<12.0 \qquad (3')$$

Moreover, it is more preferable that following conditional expression (3") be satisfied instead of conditional expression (3).

$$4.0<\Sigma D3/fL<9.0 \qquad (3'')$$

In the wide-angle optical system of the present embodiment, it is preferable that the third lens unit include a lens component which satisfies following conditional expressions (4) and (5) simultaneously:

$$1/r_2<1/r_1 \qquad (4)$$

$$1/f_{3x}<1/10\times fL \qquad (5)$$

where,
$r_1$ denotes a radius of curvature of a surface nearest to the object of each lens component in the third lens unit, $r_2$ denotes a radius of curvature of a surface nearest to the image of each lens component in the third lens unit, $f_{3x}$ denotes a focal length of each lens component in the third lens unit, and fL denotes the focal length of the wide-angle optical system at the first position.

Conditional expression (4) indicates that the lens component is a convex lens (a biconvex lens, a convex meniscus lens, a planoconvex lens). Whereas, conditional expression (5) indicates that the lens component has a small positive refractive power, or has a negative refractive power.

In other words, the lens component which satisfies conditional expressions (4) and (5) simultaneously, even when assumed to be biconvex-shaped, has a surface having a large negative refractive power. Such lens component largely contributes to achieving both of aberration correction and suppressing the rise in the light-ray height. Accordingly, by using such lens component, it is possible to achieve both of aberration correction and suppressing the rise in the light-ray height.

Moreover, in a case of having such lens components in plurality, it is possible to dispose surfaces having a positive refractive power and surfaces having a negative refractive power by and large alternately. In this case, the surfaces having a positive refractive power and the surfaces having a negative refractive power are to be disposed at an interval nearly equal to the focal length of the wide-angle optical system, and an appropriate refractive power is to be allocated to each refractive surface. By making such arrangement, it is possible to suppress the rise in the light-ray height, to secure a long back focus, and to carry out favorable aberration correction simultaneously.

In a case of not satisfying conditional expression (4) and conditional expression (5) simultaneously, it becomes difficult to have a balance of allocation of the positive refractive power and the negative refractive power. As a result, it becomes difficult to suppress the rise in the light-ray height, to secure a long back focus, and to carry out favorable aberration correction simultaneously.

It is preferable that following conditional expression (5') be satisfied instead of conditional expression (5).

$$1/f_{3x}<1/20\times fL \qquad (5')$$

Moreover, it is more preferable that following conditional expression (5") be satisfied instead of conditional expression (5).

$$1/f_{3x}<1/25\times fL \qquad (5'')$$

In the wide-angle optical system of the present embodiment, it is preferable that following conditional expression (6) be satisfied:

$$-1.5<\beta 3F<-0.3 \qquad (6)$$

where,
β3F denotes a magnification of the third lens unit at the first position.

In a case in which a value exceeds an upper limit value of conditional expression (6), securing an adequate back focus becomes difficult. In a case in which the value falls below a lower limit value of conditional expression (6), securing an effective F-number becomes difficult. The effective F-number, for instance, is an F-number at the second position. In a case in which securing the effective F-number is difficult, or in other words, in a case in which it is not possible to suppress an increase in the F-number, at the second position, aberration correction becomes difficult or avoiding degradation of an imaging performance due to diffraction becomes difficult.

It is preferable that following conditional expression (6') be satisfied instead of conditional expression (6).

$$-1.2<\beta 3F<-0.4 \tag{6'}$$

Moreover, it is more preferable that following conditional expression (6") be satisfied instead of conditional expression (6).

$$-1.0<\beta 3F<-0.5 \tag{6"}$$

In the wide-angle optical system of the present embodiment, it is preferable that following conditional expression (7) be satisfied:

$$2.0<f_3/fL<6.0 \tag{7}$$

where, $f_3$ denotes a focal length of the third lens unit, and fL denotes the focal length of the wide-angle optical system at the first position.

In a case in which a value exceeds an upper limit value of conditional expression (7), it becomes difficult to suppress the rise in the light-ray height in the predetermined range. In a case in which the value falls below a lower limit value of conditional expression (7), securing an adequate back focus becomes difficult or securing the effective F-number becomes difficult. In this case, aberration correction becomes difficult or avoiding degradation of an imaging performance due to diffraction becomes difficult.

It is preferable that following conditional expression (7') be satisfied instead of conditional expression (7).

$$2.5<f_3/fL<5.0 \tag{7'}$$

Moreover, it is more preferable that following conditional expression (7") be satisfied instead of conditional expression (7).

$$3.0<f_3/fL<4.5 \tag{7"}$$

In the wide-angle optical system of the present embodiment, it is preferable that following conditional expression (8) be satisfied:

$$-0.8<fL/f_{31}<1.0 \tag{8}$$

where, $f_{31}$ denotes a focal length of a lens component located nearest to the object in the third lens unit, and fL denotes the focal length of the wide-angle optical system at the first position.

In a case in which a value exceeds an upper limit value of conditional expression (8), the spherical aberration and the coma are susceptible to occur, or a manufacturing error sensitivity is susceptible to become high. Even when an image sensor with a large number of pixels is used, acquiring a sharp image corresponding to the large number of pixels becomes difficult. Moreover, securing the desired back focus also becomes difficult. In a case in which the value falls below a lower limit value of conditional expression (8), the light-ray height becomes high. Consequently, in a case in which the wide-angle optical system of the present embodiment is used for an optical system of an endoscope, a diameter of an insertion portion becomes large.

It is preferable that following conditional expression (8') be satisfied instead of conditional expression (8).

$$-0.5<fL/f_{31}<0.7 \tag{8'}$$

Moreover, it is more preferable that following conditional expression (8") be satisfied instead of conditional expression (8).

$$-0.3<fL/f_{31}<0.5 \tag{8"}$$

It is preferable that the wide-angle optical system of the present embodiment include a first refractive surface, wherein the first refractive surface be a refractive surface which satisfies following conditional expression (9), and the first refractive surface be located at a distance not more than 2.5×fL toward the image side from a vertex nearest to the object of the third lens unit.

$$0.10<(_an_{SNi}'-_an_{SNi})/_ar_{SNi}<0.70 \tag{9}$$

where, $_an_{SNi}$ denotes a refractive index for a d-line of a medium located on the object side of the first refractive surface, $_an_{SNi}'$ denotes a refractive index for the d-line of a medium located on the image side of the first refractive surface, $_ar_{SNi}$ denotes a radius of curvature near the optical axis of the first refractive surface, and fL denotes the focal length of the wide-angle optical system at the first position.

In a case in which a value exceeds an upper limit value of conditional expression (9), correction of the spherical aberration and correction of the coma become difficult. In a case in which the value falls below a lower limit value of conditional expression (9), the low light-ray height cannot be maintained in the predetermined range.

It is preferable that following conditional expression (9') be satisfied instead of conditional expression (9).

$$0.15<(_an_{SNi}'-_an_{SNi})/_ar_{SNi}<0.55 \tag{9'}$$

Moreover, it is more preferable that following conditional expression (9") be satisfied instead of conditional expression (9).

$$0.20<(_an_{SNi}'-_an_{SNi})/_ar_{SNi}<0.45 \tag{9"}$$

As mentioned above, $_an_{SNi}$ and $_an_{SNi}'$ denote refractive index. More elaborately, $_an_{SNi}$ is a refractive index for the d-line of the medium which is located on the object side of the first refractive surface, and which is adjacent to the first refractive surface, and $_an_{SNi}'$ is a refractive index for the d-line of the medium which is located on the image side of the first refractive surface, and which is adjacent to the first refractive surface.

It is preferable that the wide-angle optical system of the present embodiment include a second refractive surface, wherein the second refractive surface be a refractive surface which satisfy following conditional expression (10), and the second refractive surface be located at a distance not less than 2.5×fL toward the image side from a vertex nearest to the object of the third lens unit:

$$-0.60<(_bn_{SNi}'-_bn_{SNi})/_br_{SNi}<-0.05 \tag{10}$$

where, $_bn_{SNi}$ denotes a refractive index for the d-line of a medium located on the object side of the second refractive surface, $_bn_{SNi}'$ denotes a refractive index for the d-line of a medium located on the image side of the second refractive surface, $_br_{SNi}$ denotes a radius of curvature near the optical axis of the second refractive surface, and fL denotes the focal length of the wide-angle optical system at the first position.

In a case in which a value exceeds an upper limit value of conditional expression (10), the low light-ray height cannot be maintained in the predetermined range. In a case in which the value falls below a lower limit value of conditional expression (10), correction of the spherical aberration and correction of the coma become difficult.

It is preferable that following conditional expression (10') be satisfied instead of conditional expression (10).

$$-0.55 < (_bn_{SNi}' - _bn_{SNi})/_br_{SNi} < -0.09 \quad (10')$$

Moreover, it is more preferable that following conditional expression (10") be satisfied instead of conditional expression (10).

$$-0.50 < (_bn_{SNi}' - _bn_{SNi})/_br_{SNi} < -0.12 \quad (10")$$

As mentioned above, $_bn_{SNi}$ and $_bn_{SNi}'$ denote refractive index. More elaborately, $_bn_{SNi}$ is a refractive index for the d-line of the medium which is located on the object side of the second refractive surface, and which is adjacent to the second refractive surface, and $_bn_{SNi}'$ is a refractive index for the d-line of the medium which is disposed on the image side of the second refractive surface, and which is adjacent to the second refractive surface.

In the wide-angle optical system of the present embodiment, it is preferable that the third lens unit include a plurality of positive single lenses, and from among the plurality of positive single lenses, a positive single lens which is located nearest to the image satisfy following conditional expression (11):

$$2.0 < f_{3R}/fL < 10.0 \quad (11)$$

where,
$f_{3R}$ denotes a focal length of the positive single lens located nearest to the image, and
fL denotes the focal length of the wide-angle optical system at the first position.

In a case in which a value exceeds an upper limit value of conditional expression (11), it becomes difficult to secure adequately a numerical aperture on an image side while securing an adequate back focus. In a case in which the value falls below a lower limit value of conditional expression (11), correction of an off-axis aberration, such as, correction of the astigmatism becomes difficult.

It is preferable that following conditional expression (11') be satisfied instead of conditional expression (11).

$$2.5 < f_{3R}/fL < 8.0 \quad (11')$$

Moreover, it is more preferable that following conditional expression (11") be satisfied instead of conditional expression (11).

$$3.0 < f_{3R}/fL < 7.0 \quad (11")$$

In the wide-angle optical system of the present embodiment, it is preferable that the third lens unit include an object-side cemented lens which is located nearest to the object and an image-side cemented lens which is located nearest to the image, and following conditional expression (12) be satisfied:

$$-30 < (\nu_{3RCP} - \nu_{3RCN}) - (\nu_{3FCP} - \nu_{3FCN}) < 110 \quad (12)$$

where,
$\nu_{3FCP}$ denotes an Abbe number for the d-line for a positive lens in the object-side cemented lens,
$\nu_{3FCN}$ denotes an Abbe number for the d-line for a negative lens in the object-side cemented lens,
$\nu_{3RCP}$ denotes an Abbe number for the d-line for a positive lens in the image-side cemented lens, and
$\nu_{3RCN}$ denotes an Abbe number for the d-line for a negative lens in the image-side cemented lens.

In a case in which a value exceeds an upper limit value of conditional expression (12), correction of a longitudinal chromatic aberration is susceptible to becomes excessive and correction of a chromatic aberration of magnification is susceptible to become inadequate. In a case in which the value falls below a lower limit value of conditional expression (12), correction of the longitudinal chromatic aberration is susceptible to become inadequate and correction of the chromatic aberration of magnification is susceptible to become excessive.

It is preferable that following conditional expression (12') be satisfied instead of conditional expression (12).

$$-20 < (\nu_{3RCP} - \nu_{3RCN}) - (\nu_{3FCP} - \nu_{3FCN}) < 100 \quad (12')$$

Moreover, it is more preferable that following conditional expression (12") be satisfied instead of conditional expression (12).

$$-15 < (\nu_{3RCP} - \nu_{3RCN}) - (\nu_{3FCP} - \nu_{3FCN}) < 95 \quad (12")$$

In the wide-angle optical system of the present embodiment, it is preferable that a cemented surface located nearest to the image in the third lens unit satisfy following conditional expression (13):

$$-0.80 < fL/r_{SNr} < 0.60 \quad (13)$$

where,
$r_{SNr}$ denotes a radius of curvature near the optical axis of the cemented surface located nearest to the image, and
fL denotes the focal length of the wide-angle optical system at the first position.

In a case in which a value exceeds an upper limit value of conditional expression (13), correction of an off-axis aberration, such as correction of the astigmatism, becomes difficult. In a case in which the value falls below a lower limit value of conditional expression (13), correction of the spherical aberration is susceptible to become excessive.

It is preferable that following conditional expression (13') be satisfied instead of conditional expression (13).

$$-0.70 < L/r_{SNr} < 0.50 \quad (13')$$

Moreover, it is more preferable that following conditional expression (13") be satisfied instead of conditional expression (13).

$$-0.65 < fL/r_{SNr} < 0.45 \quad (13")$$

In the wide-angle optical system of the present embodiment, it is preferable that a cemented lens which satisfies following conditional expression (14), (15), and (16) be included in lens components up to a third lens component from the object side in the third lens unit:

$$-1.0 < (r_{3XF} - r_{3XR})/(r_{3XF} + r_{3XR}) < 0.5 \quad (14)$$

$$1/r_{3XC} \times r_{3XF} < 0 \quad (15)$$

$$1/r_{3XC} \times r_{3XR} < 0 \quad (16)$$

where,
$r_{3XF}$ denotes a radius of curvature of a surface nearest to the object of a predetermined cemented lens,
$r_{3XR}$ denotes a radius of curvature of a surface nearest to the image of the predetermined cemented lens,
$r_{3XC}$ denotes a radius of curvature on the optical axis of a cemented surface of the predetermined cemented lens, and the predetermined cemented lens is the cemented lens which satisfies conditional expressions (14), (15), and (16).

A plurality of cemented lenses may be included in the lens components up to the third lens component from the object side. In this case, one cemented lens may be a cemented lens which satisfies conditional expressions (14), (15), and (16).

Conditional expression (14) regulates with respect to an amount equivalent to a reciprocal of a so-called shape factor. Conditional expressions (15) and (16) stipulate that a direction of the cemented surface and a direction of any of air contact surfaces are opposite. The air contact surface is a surface nearest to the object of the lens component and a surface nearest to the image of the lens component.

A case in which any of conditional expressions (14), (15), and (16) is not satisfied, it becomes difficult to achieve both of maintaining the light-ray height low in the predetermined range and securing an adequate back focus.

It is preferable that following conditional expression (14') be satisfied instead of conditional expression (14).

$$-0.8<(r_{3XF}-r_{3XR})/(r_{3XF}+r_{3XR})<0.3 \qquad (14')$$

Moreover, it is more preferable that following conditional expression (14″) be satisfied instead of conditional expression (14).

$$-0.6<(r_{3XF}-r_{3XR})/(r_{3XF}+r_{3XR})<0.2 \qquad (14'')$$

In the wide-angle optical system of the present embodiment, it is preferable that the third lens unit include a plurality of positive lenses, the plurality of positive lenses include a first positive lens and a second positive lens, the first positive lens, among the plurality of positive lenses, be a positive lens located nearest to the object, the second positive lens, among the plurality of positive lenses, be a positive lens located second from the object, and following conditional expression (17) be satisfied:

$$-75<\nu_{31P}-\nu_{32P}<35 \qquad (17)$$

where, $\nu_{31P}$ denotes an Abbe number for the first positive lens, and $\nu_{32P}$ denotes an Abbe number for the second positive lens.

In a case in which a value exceeds an upper limit value of conditional expression (17), although the chromatic aberration of magnification could be corrected favorably, correction of the longitudinal chromatic aberration is susceptible to become excessive. In a case in which the value falls below a lower limit value of conditional expression (17), although the chromatic aberration of magnification could be corrected favorably, correction of the longitudinal chromatic aberration is susceptible to become inadequate.

It is preferable that following conditional expression (17') be satisfied instead of conditional expression (17).

$$-65<\nu_{31P}-\nu_{32P}<25 \qquad (17')$$

Moreover, it is more preferable that following conditional expression (17″) be satisfied instead of conditional expression (17).

$$-60<\nu_{31P}-\nu_{32P}<20 \qquad (17'')$$

In the wide-angle optical system of the present embodiment, it is preferable that the third lens unit include a plurality of positive lenses, the plurality of positive lenses include a first positive lens, a second positive lens, and a third positive lens, the first positive lens, among the plurality of positive lenses, be a positive lens located nearest to the object, the second positive lens, among the plurality of positive lenses, be a positive lens located second from the object, the third positive lens, among the plurality of positive lenses, be a positive lens located third from the object, and following conditional expression (18) be satisfied:

$$-10<\nu_{33P}-(\nu_{31P}+\nu_{32P})/2<70 \qquad (18)$$

where, $\nu_{31P}$ denotes the Abbe number for the first positive lens, $\nu_{32P}$ denotes the Abbe number for the second positive lens, and $\nu_{33P}$ denotes an Abbe number for the third positive lens.

In a case in which a value exceeds an upper limit value of conditional expression (18), although the chromatic aberration of magnification could be corrected favorably, correction of the longitudinal chromatic aberration is susceptible to become inadequate. In a case in which the value falls below a lower limit value of conditional expression (18), although the chromatic aberration of magnification could be corrected favorably, correction of the longitudinal chromatic aberration is susceptible to become excessive.

It is preferable that following conditional expression (18') be satisfied instead of conditional expression (18).

$$0<\nu_{33P}-(\nu_{31P}+\nu_{32P})/2<60 \qquad (18')$$

Moreover, it is more preferable that following conditional expression (18″) be satisfied instead of conditional expression (18).

$$5<\nu_{33P}-(\nu_{31P}+\nu_{32P})/2<50 \qquad (18'')$$

In the wide-angle optical system of the present embodiment, it is preferable that the third lens unit include a plurality of negative lenses, the plurality of negative lenses include a first negative lens and a second negative lens, the first negative lens, among the plurality of negative lenses, be a negative lens located nearest to the object, the second negative lens, among the plurality of negative lenses, be a negative lens located second from the object, and following conditional expression (19) be satisfied:

$$-20<\nu_{31N}-\nu_{32N}<40 \qquad (19)$$

where, $\nu_{31N}$ denotes an Abbe number for the first negative lens, and $\nu_{32N}$ denotes an Abbe number for the second negative lens.

In a case in which a value exceeds an upper limit value of conditional expression (19), although the chromatic aberration of magnification could be corrected favorably, correction of the longitudinal chromatic aberration is susceptible to become inadequate. In a case in which the value falls below a lower limit value of conditional expression (19), although the chromatic aberration of magnification could be corrected favorably, correction of the longitudinal chromatic aberration is susceptible to become excessive.

It is preferable that following conditional expression (19') be satisfied instead of conditional expression (19).

$$-16<\nu_{31N}-\nu_{32N}<33 \qquad (19')$$

Moreover, it is more preferable that following conditional expression (19″) be satisfied instead of conditional expression (19).

$$-12<\nu_{31N}-\nu_{32N}<28 \qquad (19'')$$

In the wide-angle optical system of the present embodiment, it is preferable that the third lens unit be fixed at the time of focal-position adjustment.

The number of lens components is large in the third lens unit. Moreover, in the third lens unit, there is a strong tendency of a manufacturing-error sensitivity becoming high. Therefore, it is preferable to make the third lens unit fixed at the time of focal-position adjustment.

Preferable arrangements and conditional expressions for the first lens unit and preferable arrangements and conditional expressions for the second lens unit will be described below.

In the wide-angle optical system of the present embodiment, it is preferable that following conditional expression (20) be satisfied:

$$-50<(R21F+R21R)/(R21F-R21R)<15 \qquad (20)$$

where,

R21F denotes a radius of curvature of a surface on the object side of a predetermined lens component, R21R denotes a radius of curvature of a surface on the image side of the predetermined lens component, and the predetermined lens component is a lens component located nearest to the object in the second lens unit.

In a case in which a value exceeds an upper limit value of conditional expression (20), a variation in the astigmatism at the time of focal-position adjustment is susceptible to become large. In a case in which the value falls below a lower limit value of conditional expression (20), a variation in the spherical aberration at the time of focal-position adjustment is susceptible to become large.

It is preferable that following conditional expression (20') be satisfied instead of conditional expression (20).

$$-30<(R21F+R21R)/(R21F-R21R)<10 \qquad (20')$$

Moreover, it is more preferable that following conditional expression (20") be satisfied instead of conditional expression (20).

$$-15<(R21F+R21R)/(R21F-R21R)<7 \qquad (20'')$$

In the wide-angle optical system of the present embodiment, it is preferable that following conditional expression (21) be satisfied:

$$0.3<D21/fL<2.0 \qquad (21)$$

where,

D21 denotes a distance on an optical axis between a surface nearest to the object and a surface nearest to the image of the second lens unit, and fL denotes the focal length of the wide-angle optical system at the first position.

In a case in which a value exceeds an upper limit value of conditional expression (21), it becomes difficult to maintain the light-ray height low in the predetermined range. In a case in which the value falls below a lower limit value of conditional expression (21), it becomes difficult to achieve a balance of the variation in the spherical aberration and the variation in the astigmatism at the time of focal-position adjustment. As a result, it becomes difficult to maintain a flatness of an image plane at the time of focal-position adjustment It is preferable that following conditional expression (21') be satisfied instead of conditional expression (21).

$$0.4<D21/fL<1.5 \qquad (21')$$

Moreover, it is more preferable that following conditional expression (21") be satisfied instead of conditional expression (21).

$$0.5<D21/fL<1.0 \qquad (21'')$$

In the wide-angle optical system of the present embodiment, it is preferable that following conditional expression (22) be satisfied:

$$1.04<\beta 2F<1.40 \qquad (22)$$

where,

β2F denotes a magnification of the second lens unit at the first position.

In a case in which a value exceeds an upper limit value of conditional expression (22), an amount of focus movement with respect to the amount of movement of the second lens unit (hereinafter, referred to as 'focusing sensitivity') becomes excessively high. In this case, an accuracy at the time of stopping the second lens unit (hereinafter, referred to as 'stopping accuracy') becomes excessively high. Consequently, a moving mechanism becomes complicated.

In a case in which a value falls below a lower limit value of conditional expression (22), the focusing sensitivity is susceptible to become low. In this case, since the amount of movement of the second lens unit increases, a space for the movement has to be made wide. Consequently, an optical unit becomes large.

It is preferable that following conditional expression (22') be satisfied instead of conditional expression (22).

$$1.06<\beta 2F<1.35 \qquad (22')$$

Moreover, it is more preferable that following conditional expression (22") be satisfied instead of conditional expression (22").

$$1.08<\beta 2F<1.30 \qquad (22'')$$

In the wide-angle optical system of the present embodiment, it is preferable that following conditional expression (23) be satisfied:

$$1.01<\beta 2N/\beta 2F<1.15 \qquad (23)$$

where,

β2F denotes the magnification of the second lens unit at the first position, and β2N denotes a magnification of the second lens unit at the second position.

In a case in which conditional expression (23) is satisfied, since a focal length at a far point becomes short, it is possible to secure a wide angle of view at a far point. Moreover, since a focal length at a near point becomes long, it is possible to achieve a high magnification at a near point.

An optical system having a wide angle of view at a far point and a high magnification at a near point is appropriate for an optical system of an endoscope. Therefore, it is possible to use the wide-angle optical system of the present embodiment as an optical system for an endoscope.

In an endoscope, for instance, by observing a wide range, it is checked if there is a lesion part. Moreover, when it is confirmed that there is a lesion part, the lesion part is magnified and observed in detail. Therefore, it is preferable that an optical system of an endoscope have a wide angle of view for a far-point observation, and have a high magnification for a near-point observation.

Moreover, in the near-point observation, it is necessary to observe a lesion part in detail. Therefore, in an optical system for an endoscope, it is preferable to have an ability to focus with a high accuracy.

In a case in which a value exceeds an upper limit value of conditional expression (23), the focusing sensitivity at a near-point side becomes high. In this case, the stopping accuracy at the near-point side becomes high. Consequently, it becomes difficult to focus with high accuracy. In a case in which the value falls below a lower limit value of conditional expression (23), securing a wide-angle of view in the far-point observation and securing a high magnification in the near-point observation become difficult. Consequently, it becomes inappropriate for an optical system of an endoscope.

It is preferable that following conditional expression (23') be satisfied instead of conditional expression (23).

$$1.01 < \beta 2N/\beta 2F < 1.10 \quad (23')$$

Moreover, it is more preferable that following conditional expression (23") be satisfied instead of conditional expression (23).

$$1.02 < \beta 2N/\beta 2F < 1.07 \quad (23'')$$

In the wide-angle optical system of the present embodiment, it is preferable that following conditional expression (24) be satisfied:

$$0.10 < (1-\beta 2F^2) \times \beta 3F^2 < 0.45 \quad (24)$$

where,
β2F denotes the magnification of the second lens unit at the first position, and
β3F denotes a magnification of the third lens unit at the first position.

In a case in which a value exceeds an upper limit value of conditional expression (24), the focusing sensitivity at the far-point side becomes excessively high. In this case, the stopping accuracy at the far-point side becomes high. In a case in which the value falls below a lower limit value of conditional expression (24), the focusing sensitivity at the far-point side is susceptible to become low. In this case, since the amount of movement of the second lens unit increases, the space for the movement has to be made wide. Consequently, the optical unit becomes large.

It is preferable that following conditional expression (24') be satisfied instead of conditional expression (24).

$$0.13 < (1-\beta 2F^2) \times \beta 3F^2 < 0.40 \quad (24')$$

Moreover, it is more preferable that following conditional expression (24") be satisfied instead of conditional expression (24).

$$0.16 < (1-\beta 2F^2) \times \beta 3F^2 < 0.35 \quad (24'')$$

In the wide-angle optical system of the present embodiment, it is preferable that following conditional expression (25) be satisfied:

$$0.15 < (1-\beta 2N^2) \times \beta 3N^2 < 0.60 \quad (25)$$

where,
β2N denotes the magnification of the second lens unit at the second position, and
β3N denotes a magnification of the third lens unit at the second position.

In a case in which a value exceeds an upper limit value of conditional expression (25), the focusing sensitivity at the near-point side becomes excessively high. In this case, the stopping accuracy at the near-point side becomes high. In a case in which the value falls below a lower limit value of conditional expression (25), the focusing sensitivity at the near-point side is susceptible to become low. In this case, since the amount of movement of the second lens unit increases, the space for the movement has to be made wide.

It is preferable that following conditional expression (25') be satisfied instead of conditional expression (25).

$$0.20 < (1-\beta 2N^2) \times \beta 3N^2 < 0.50 \quad (25')$$

Moreover, it is more preferable that following conditional expression (25") be satisfied instead of conditional expression (25).

$$0.25 < (1-\beta 2N^2) \times \beta 3N^2 < 0.42 \quad (25'')$$

In the wide-angle optical system of the present embodiment, it is preferable that the second lens unit include only a positive lens.

By making such arrangement, it is possible to reduce the variation in the astigmatism at the time of focal-position adjustment.

In the wide-angle optical system of the present embodiment, it is preferable that the first lens unit include only a lens component which satisfies following conditional expression (26):

$$1/r_{LXF} < 1/r_{LXR} \quad (26)$$

where,
$r_{LXF}$ denotes a radius of curvature on the optical axis of a surface nearest to the object of each lens component in the first lens unit, and
$r_{LXR}$ denotes a radius of curvature on the optical axis of a surface nearest to the image of each lens component in the first lens unit.

In a case in which conditional expression (26) is not satisfied, it is difficult to carry out correction of the astigmatism.

In the wide-angle optical system of the present embodiment, it is preferable that the first lens unit include only a plurality of negative single lenses, and each of the plurality of negative single lenses have Abbe number larger than Abbe number for a positive lens nearest to the object in the third lens unit.

For making the light-ray height low in an optical system having an extremely wide angle of view, shortening a distance from a surface of incidence up to an entrance-pupil position as much as possible is effective. For this, not disposing a lens which corrects a chromatic aberration in the first lens unit may be one of the options. In a case in which a lens which corrects the chromatic aberration is not disposed in the first lens unit, the first lens unit includes only the single lens.

In this case, the chromatic aberration of magnification is susceptible to occur in the first lens unit. However, it is possible to correct the chromatic aberration of magnification which occurred in the first lens unit, in the third lens unit. At this time, Abbe number for the negative single lens in the first lens unit is to be made larger than Abbe number for the positive lens nearest to the object in the third lens unit.

The positive lens nearest to the object in the third lens unit is located at a distance closest from the negative single lens in the first lens unit. Consequently, correction of the chromatic aberration of magnification becomes possible without the longitudinal chromatic aberration being deteriorated. In a case in which Abbe number for the negative single lens in the first lens unit is smaller than Abbe number for the positive lens nearest to the object in the third lens unit, it becomes difficult to carry out correction of the longitudinal chromatic aberration and correction of the chromatic aberration of magnification simultaneously.

In the wide-angle optical system of the present embodiment, it is preferable that following conditional expression (27) be satisfied:

$$0.20 < SD1/fL < 5.0 \quad (27)$$

where,
- SD1 denotes a distance from a vertex nearest to the object in the first lens unit up to a vertex nearest to the image in the first lens unit, and
- fL denotes the focal length of the wide-angle optical system at the first position.

By satisfying conditional expression (27), it is possible to secure the back focus without making large an outer diameter of the first lens unit, and particularly, an outer diameter of the lens nearest to the object, and it is possible to correct favorably an off-axis aberration such as the astigmatism, even when the angle of view is wide.

In a case in which a value exceeds an upper limit value of conditional expression (27), the outer diameter of the lens nearest to the object is susceptible to become large. In a case in which the value falls below a lower limit value of conditional expression (27), it becomes difficult to secure an appropriate back focus or it becomes difficult correct an off-axis aberration.

It is preferable that following conditional expression (27') be satisfied instead of conditional expression (27).

$$0.25 < SD1/fL < 4.0 \tag{27'}$$

Moreover, it is more preferable that following conditional expression (27") be satisfied instead of conditional expression (27).

$$0.30 < SD1/fL < 3.5 \tag{27"}$$

In the wide-angle optical system of the present embodiment, it is preferable that following conditional expression (28) be satisfied:

$$3.5 < fB/fL < 10 \tag{28}$$

where,
- fB denotes an air conversion length of a distance from a vertex of the image side of a lens component nearest to the image up to an imaging surface, and
- fL denotes the focal length of the wide-angle optical system at the first position.

In a case in which a value exceeds an upper limit value of conditional expression (28), it becomes difficult to make the light-ray height low in the predetermined range. Or, the imaging performance is degraded. In a case in which the value falls below a lower limit value of conditional expression (28), it becomes difficult to make the light-ray height low in the predetermined range and to correct various aberrations favorably, while securing an appropriate back focus.

In the wide-angle optical system of the present embodiment, it is preferable that following conditional expression (29) be satisfied:

$$2 \times y_{max} < fL \times \tan \omega_{max} \tag{29}$$

where,
- $y_{max}$ denotes a maximum image height,
- $\omega_{max}$ denotes an angle of view corresponding to the maximum image height, and
- fL denotes the focal length of the wide-angle optical system at the first position.

The wide-angle optical system of the present embodiment is an optical system which has a high resolution and a small outer diameter, and an actuator necessary for the focal-position adjustment disposed therein. Accordingly, it is possible to use the wide-angle optical system of the present embodiment for an optical system of an endoscope.

For using the wide-angle optical system of the present embodiment for an optical system of an endoscope, it is preferable that an angle of view of not less than 100 degrees be secured, for instance. In an optical system having an angle of view of not less than 100 degrees, an occurrence of a distortion is acceptable. Accordingly, such optical system does not satisfy following expression (A). Expression (A) is a condition with no distortion.

$$Y_{max} = fL \times \tan \omega_{max} \tag{A}$$

Instead, the wide-angle optical system of the present embodiment satisfies conditional expression (29). By satisfying conditional expression (29), it is possible to make an outer diameter of an optical unit small while securing a wide angle of view. Accordingly, it is possible to use the wide-angle optical system of the present embodiment for an optical system of an endoscope.

In the wide-angle optical system of the present embodiment, it is preferable that following conditional expression (30) be satisfied:

$$ER3 < fL/(2 \times F_{EX}) \tag{30}$$

where,
- ER3 denotes an effective radius of the cemented surface Sc,
- $F_{EX}$ denotes an effective F-number at the first position, and
- fL denotes the focal length of the wide-angle optical system at the first position.

Conditional expression (30) is a conditional expression related to the light-ray height. By satisfying conditional expression (30), it is possible to use the wide-angle optical system of the present embodiment for an optical system of an endoscope. The effective radius is determined by the height of an outermost light ray in a plane.

An image pickup apparatus of the present embodiment includes an optical system, and an image sensor which is disposed on an image plane, wherein the image sensor has an image pickup surface, and converts an image formed on the image pickup surface by the optical system to an electric signal, and the optical system is the abovementioned wide-angle optical system.

According to the image pickup apparatus of the present embodiment, even when an image sensor with a large number of pixels is used, it is possible to acquire a sharp image corresponding to the large number of pixels.

Embodiments and examples of a wide-angle optical system will be described below in detail by referring to the accompanying diagrams. However, the present disclosure is not restricted to the embodiments and the examples described below.

Lens cross-sectional views of each example will be described below.

FIG. 1A, FIG. 2A, FIG. 3A, FIG. 4A, FIG. 5A, FIG. 6A, FIG. 7A, FIG. 8A, FIG. 9A, and FIG. 10A are cross-sectional views at a far point.

FIG. 1B, FIG. 2B, FIG. 3B, FIG. 4B, FIG. 5B, FIG. 6B, FIG. 7B, FIG. 8B, FIG. 9B, and FIG. 10B are cross-sectional views at a near point.

A first lens unit is denoted by G1, a second lens unit is denoted by G2, a third lens unit is denoted by G3, an aperture stop is denoted by S, a filter is denoted by F, a cover glass is denoted by C, a prism is denoted by P, and an image plane (image pickup surface) is denoted by I.

Aberration diagrams of each example will be described below. Aberration diagrams are shown in order of aberration diagrams at a far point and aberration diagrams at a near point.

Aberration diagrams at a far point are as follow.

FIG. 11A, FIG. 12A, FIG. 13A, FIG. 14A, FIG. 15A, FIG. 16A, FIG. 17A, FIG. 18A, FIG. 19A, and FIG. 20A show a spherical aberration (SA).

FIG. 11B, FIG. 12B, FIG. 13B, FIG. 14B, FIG. 15B, FIG. 16B, FIG. 17B, FIG. 18B, FIG. 19B, and FIG. 20B show an astigmatism (AS).

FIG. 11C, FIG. 12C, FIG. 13C, FIG. 14C, FIG. 15C, FIG. 16C, FIG. 17C, FIG. 18C, FIG. 19C, and FIG. 20C show a chromatic aberration of magnification (CC).

FIG. 11D, FIG. 12D, FIG. 13D, FIG. 14D, FIG. 15D, FIG. 16D, FIG. 17D, FIG. 18D, FIG. 19D, and FIG. 20D show a distortion (DT).

Aberration diagrams at a near point are as follow.

FIG. 11E, FIG. 12E, FIG. 13E, FIG. 14E, FIG. 15E, FIG. 16E, FIG. 17E, FIG. 18E, FIG. 19E, and FIG. 20E show a spherical aberration (SA).

FIG. 11F, FIG. 12F, FIG. 13F, FIG. 14F, FIG. 15F, FIG. 16F, FIG. 17F, FIG. 18F, FIG. 19F, and FIG. 20F show an astigmatism (AS).

FIG. 11G, FIG. 12G, FIG. 13G, FIG. 14G, FIG. 15G, FIG. 16G, FIG. 17G, FIG. 18G, FIG. 19G, and FIG. 20G show a chromatic aberration of magnification (CC).

FIG. 11H, FIG. 12H, FIG. 13H, FIG. 14H, FIG. 15H, FIG. 16H, FIG. 17H, FIG. 18H, FIG. 19H, and FIG. 20H show a distortion (DT).

A wide-angle optical system of an example 1 includes in order from an object side, a first lens unit G1 having a negative refractive power, a second lens unit G2 having a positive refractive power, and a third lens unit G3 having a positive refractive power.

The first lens unit G1 includes a planoconcave negative lens L1, a biconcave negative lens L2, and a positive meniscus lens L3 having a convex surface directed toward the object side. The biconcave negative lens L2 and the positive meniscus lens L3 are cemented.

The second lens unit G2 includes a positive meniscus lens L4 having a convex surface directed toward the object side.

The third lens unit G3 includes a negative meniscus lens L5 having a convex surface directed toward the object side, a biconvex positive lens L6, a negative meniscus lens L7 having a convex surface directed toward the object side, a biconvex positive lens L8, a biconcave negative lens L9, a biconvex positive lens L10, a biconvex positive lens L11, and a negative meniscus lens L12 having a convex surface directed toward the object side.

The negative meniscus lens L5 and the biconvex positive lens L6 are cemented. The negative meniscus lens L7 and the biconvex positive lens L8 are cemented. The biconcave negative lens L9 and the biconvex positive lens L10 are cemented.

A filter F is disposed in the first lens unit G1. An aperture stop S is disposed in the third lens unit G3. A cover glass C and a prism P are disposed on an image side of the third lens unit G3.

In an adjustment of a focal position, the second lens unit G2 is moved. At the time of adjustment from a far point to a near point, the second lens unit G2 is moved toward the image side.

A wide-angle optical system of an example 2 includes in order from an object side, a first lens unit G1 having a negative refractive power, a second lens unit G2 having a positive refractive power, and a third lens unit G3 having a positive refractive power.

The first lens unit G1 includes a planoconcave negative lens L1, a biconcave negative lens L2, and a biconvex positive lens L3. The biconcave negative lens L2 and the biconvex positive lens L3 are cemented.

The second lens unit G2 includes a positive meniscus lens L4 having a convex surface directed toward the object side.

The third lens unit G3 includes a biconvex positive lens L5, a biconcave negative lens L6, a biconvex positive lens L7, a positive meniscus lens L8 having a convex surface directed toward an image side, a negative meniscus lens L9 having a convex surface directed toward the image side, and a biconvex positive lens L10.

The biconcave negative lens L6 and the biconvex positive lens L7 are cemented. The positive meniscus lens L8 and the negative meniscus lens L9 are cemented.

A filter F is disposed in the first lens unit G1. An aperture stop S is disposed in the third lens unit G3. A cover glass C1, a prism P, and a cover glass C2 are disposed on an image side of the third lens unit G3.

In an adjustment of a focal position, the second lens unit G2 is moved. At the time of adjustment from a far point to a near point, the second lens unit G2 is moved toward the image side.

A wide-angle optical system of an example 3 includes in order from an object side, a first lens unit G1 having a negative refractive power, a second lens unit G2 having a positive refractive power, and a third lens unit G3 having a positive refractive power.

The first lens unit G1 includes a planoconcave negative lens L1.

The second lens unit G2 includes a positive meniscus lens L2 having a convex surface directed toward an image side.

The third lens unit G3 includes a biconvex positive lens L3, a biconcave negative lens L4, a biconvex positive lens L5, a positive meniscus lens L6 having a convex surface directed toward the image side, a negative meniscus lens L7 having a convex surface directed toward the image side, and a biconvex positive lens L8.

The biconcave negative lens L4 and the biconvex positive lens L5 are cemented. The positive meniscus lens L6 and the negative meniscus lens L7 are cemented.

A filter F is disposed between the first lens unit G1 and the second lens unit G2. An aperture stop S is disposed in the third lens unit G3. A cover glass C1, a prism P, and a cover glass C2 are disposed on an image side of the third lens unit G3.

In an adjustment of a focal position, the second lens unit G2 is moved. At the time of adjustment from a far point to a near point, the second lens unit G2 is moved toward the image side.

A wide-angle optical system of an example 4 includes in order from an object side, a first lens unit G1 having a negative refractive power, a second lens unit G2 having a positive refractive power, and a third lens unit G3 having a positive refractive power.

The first lens unit G1 includes a planoconcave negative lens L1, a biconcave negative lens L2, and a biconvex positive lens L3. The biconcave negative lens L2 and the biconvex positive lens L3 are cemented.

The second lens unit G2 includes a positive meniscus lens L4 having a convex surface directed toward the object side.

The third lens unit G3 includes a biconvex positive lens L5, a biconcave negative lens L6, a biconvex positive lens L7, a positive meniscus lens L8 having a convex surface directed toward an image side, a negative meniscus lens L9 having a convex surface directed toward the image side, and a biconvex positive lens L10.

The biconvex positive lens L5 and the biconcave negative lens L6 are cemented. The positive meniscus lens L8 and the negative meniscus lens L9 are cemented.

A filter F is disposed between the first lens unit G1 and the second lens unit G2. An aperture stop S is disposed in the third lens unit G3. A cover glass C1, a prism P, and a cover glass C2 are disposed on an image side of the third lens unit G3.

In an adjustment of a focal position, the second lens unit G2 is moved. At the time of adjustment from a far point to a near point, the second lens unit G2 is moved toward the image side.

A wide-angle optical system of an example 5 includes in order from an object side, a first lens unit G1 having a negative refractive power, a second lens unit G2 having a positive refractive power, and a third lens unit G3 having a positive refractive power.

The first lens unit G1 includes a planoconcave negative lens L1 and a negative meniscus lens L2 having a convex surface directed toward the object side.

The second lens unit G2 includes a positive meniscus lens L3 having a convex surface directed toward the object side.

The third lens unit G3 includes a biconvex positive lens L4, a biconcave negative lens L5, a biconvex positive lens L6, a positive meniscus lens L7 having a convex surface directed toward an image side, a negative meniscus lens L8 having a convex surface directed toward the image side, and a biconvex positive lens L9.

The biconcave negative lens L5 and the biconvex positive lens L6 are cemented. The positive meniscus lens L7 and the negative meniscus lens L8 are cemented.

A filter F is disposed between the first lens unit G1 and the second lens unit G2. An aperture stop S is disposed in the third lens unit G3. A cover glass C1, a prism P, and a cover glass C2 are disposed on an image side of the third lens unit G3.

In an adjustment of a focal position, the second lens unit G2 is moved. At the time of adjustment from a far point to a near point, the second lens unit G2 is moved toward the image side. The filter F is moved together with the second lens unit G2.

A wide-angle optical system of an example 6 includes in order from an object side, a first lens unit G1 having a negative refractive power, a second lens unit G2 having a positive refractive power, and a third lens unit G3 having a positive refractive power.

The first lens unit G1 includes a planoconcave negative lens L1.

The second lens unit G2 includes a positive meniscus lens L2 having a convex surface directed toward the object side.

The third lens unit G3 includes a biconvex positive lens L3, a negative meniscus lens L4 having a convex surface directed toward an image side, a biconvex positive lens L5, a biconcave negative lens L6, a biconvex positive lens L7, and a biconvex positive lens L8.

The biconvex positive lens L3 and the negative meniscus lens L4 are cemented. The biconvex positive lens L5, the biconcave negative lens L6, and the biconvex positive lens L7 are cemented.

A filter F is disposed between the first lens unit G1 and the second lens unit G2. An aperture stop S is disposed in the third lens unit G3. A prism P and a cover glass C are disposed on an image side of the third lens unit G3.

In an adjustment of a focal position, the second lens unit G2 is moved. At the time of adjustment from a far point to a near point, the second lens unit G2 is moved toward the image side.

A wide-angle optical system of an example 7 includes in order from an object side, a first lens unit G1 having a negative refractive power, a second lens unit G2 having a positive refractive power, and a third lens unit G3 having a positive refractive power.

The first lens unit G1 includes a planoconcave negative lens L1 and a biconcave negative lens L2.

The second lens unit G2 includes a positive meniscus lens L3 having a convex surface directed toward the object side.

The third lens unit G3 includes a negative meniscus lens L4 having a convex surface directed toward an image side, a positive meniscus lens L5 having a convex surface directed toward the object side, a biconvex positive lens L6, a biconcave negative lens L7, a biconvex positive lens L8, a negative meniscus lens L9 having a convex surface directed toward the image side, a biconvex positive lens L10, a negative meniscus lens L11 having a convex surface directed toward the image side, and a biconvex positive lens L12.

The biconvex positive lens L6 and the biconcave negative lens L7 are cemented. The biconvex positive lens L8 and the negative meniscus lens L9 are cemented. The biconvex positive lens L10 and the negative meniscus lens L11 are cemented.

A filter F is disposed in the first lens unit G1. An aperture stop S is disposed in the third lens unit G3. A cover glass C1, a prism P, and a cover glass C2 are disposed on an image side of the third lens unit G3.

In an adjustment of a focal position, the second lens unit G2 is moved. At the time of adjustment from a far point to a near point, the second lens unit G2 is moved toward the image side.

A wide-angle optical system of an example 8 includes in order from an object side, a first lens unit G1 having a negative refractive power, a second lens unit G2 having a positive refractive power, and a third lens unit G3 having a positive refractive power.

The first lens unit G1 includes a planoconcave negative lens L1 and a planoconcave negative lens L2.

The second lens unit G2 includes a positive meniscus lens L3 having a convex surface directed toward the object side.

The third lens unit G3 includes a biconcave negative lens L4, a biconvex positive lens L5, a biconvex positive lens L6, a biconcave negative lens L7, a biconvex positive lens L8, a negative meniscus lens L9 having a convex surface directed toward an image side, a biconvex positive lens L10, a negative meniscus lens L11 having a convex surface directed toward the image side, and a biconvex positive lens L12.

The biconcave negative lens L4 and the biconvex positive lens L5 are cemented. The biconvex positive lens L6 and the biconcave negative lens L7 are cemented. The biconvex positive lens L8 and the negative meniscus lens L9 are cemented. The biconvex positive lens L10 and the negative meniscus lens L11 are cemented.

A filter F is disposed in the first lens unit G1. An aperture stop S is disposed in the third lens unit G3. A cover glass C1, a prism P, and a cover glass C2 are disposed on an image side of the third lens unit G3.

In an adjustment of a focal position, the second lens unit G2 is moved. At the time of adjustment from a far point to a near point, the second lens unit G2 is moved toward the image side.

A wide-angle optical system of an example 9 includes in order from an object side, a first lens unit G1 having a negative refractive power, a second lens unit G2 having a positive refractive power, and a third lens unit G3 having a positive refractive power.

The first lens unit G1 includes a planoconcave negative lens L1 and a planoconcave negative lens L2.

The second lens unit G2 includes a positive meniscus lens L3 having a convex surface directed toward the object side.

The third lens unit G3 includes a biconvex positive lens L4, a biconcave negative lens L5, a biconvex positive lens L6, a negative meniscus lens L7 having a convex surface directed toward an image side, a biconvex positive lens L8, a planoconcave negative lens L9, and a biconvex positive lens L10.

The biconvex positive lens L4 and the biconcave negative lens L5 are cemented. The biconvex positive lens L6 and the negative meniscus lens L7 are cemented. The biconvex positive lens L8 and the planoconcave negative lens L9 are cemented.

A filter F and an aperture stop S are disposed between the second lens unit G2 and the third lens unit G3. A cover glass C1, a prism P, and a cover glass C2 are disposed on an image side of the third lens unit G3.

In an adjustment of a focal position, the second lens unit G2 is moved. At the time of adjustment from a far point to a near point, the second lens unit G2 is moved toward the image side.

A wide-angle optical system of an example 10 includes in order from an object side, a first lens unit G1 having a negative refractive power, a second lens unit G2 having a positive refractive power, and a third lens unit G3 having a positive refractive power.

The first lens unit G1 includes a planoconcave negative lens L1 and a biconcave negative lens L2.

The second lens unit G2 includes a positive meniscus lens L3 having a convex surface directed toward the object side.

The third lens unit G3 includes a biconcave negative lens L4, a biconvex positive lens L5, a biconvex positive lens L6, a biconcave negative lens L7, a biconvex positive lens L8, a negative meniscus lens L9 having a convex surface directed toward an image side, a biconvex positive lens L10, a negative meniscus lens L11 having a convex surface directed toward the image side, and a biconvex positive lens L12.

The biconcave negative lens L4 and the biconvex positive lens L5 are cemented. The biconvex positive lens L6 and the biconcave negative lens L7 are cemented. The biconvex positive lens L8 and the negative meniscus lens L9 are cemented. The biconvex positive lens L10 and the negative meniscus lens L11 are cemented.

A filter F is disposed in the first lens unit G1. An aperture stop S is disposed in the third lens unit G3. A cover glass C1, a prism P, and a cover glass C2 are disposed on an image side of the third lens unit G3.

In an adjustment of a focal position, the second lens unit G2 is moved. At the time of adjustment from a far point to a near point, the second lens unit G2 is moved toward the image side.

Numerical data of each example described above is shown below. In Surface data, r denotes radius of curvature of each lens surface, d denotes a distance between respective lens surfaces, nd denotes a refractive index of each lens for a d-line, vd denotes an Abbe number for each lens and * denotes an aspherical surface. A stop is an aperture stop.

Moreover, in Various data, OBJ denotes an object distance, FL denotes a focal length of the entire system, MG denotes a magnification of the entire system, FNO. denotes an F number, FIM denotes an image height, LTL denotes a lens total length of the optical system, and FB denotes a back focus. The back focus is a unit which is expressed upon air conversion of a distance from a rearmost lens surface to a paraxial image surface. The lens total length is a distance from a frontmost lens surface to the rearmost lens surface plus back focus. Moreover, β1 denotes a magnification of the first lens unit, β2 denotes a magnification of the second lens unit, β3 denotes a magnification of the third lens unit.

Further, in Unit focal length, each of f1, f2 . . . is a focal length of each lens unit.

A shape of an aspherical surface is defined by the following expression where the direction of the optical axis is represented by z, the direction orthogonal to the optical axis is represented by y, a conical coefficient is represented by K, aspherical surface coefficients are represented by A4, A6, A8, A10, A12 . . . .

$$Z=(y^2/r)/[1+\{1-(1+k)(y/r)^2\}^{1/2}]+A4y^4+A6y^6+A8y^8+A10y^{10}+A12y^{12}+\ldots$$

Further, in the aspherical surface coefficients, 'E-n' (where, n is an integral number) indicates '10$^{-n}$'. Moreover, these symbols are commonly used in the following numerical data for each example.

Example 1

Unit mm

Surface data

| Surface no. | r | d | nd | vd | ER |
|---|---|---|---|---|---|
| Object plane | ∞ | 13.0000 | 1. | | |
| 1 | ∞ | 0.2500 | 1.88300 | 40.76 | 1.404 |
| 2* | 0.9721 | 0.5998 | 1. | | 0.965 |
| 3 | ∞ | 0.4000 | 1.49400 | 75.01 | 0.945 |
| 4 | ∞ | 0.1025 | 1. | | 0.891 |
| 5 | −7.4090 | 0.3000 | 1.81600 | 46.62 | 0.881 |
| 6 | 1.0886 | 0.7980 | 1.80518 | 25.42 | 0.840 |
| 7 | 76.4205 | d7 | 1. | | 0.820 |
| 8* | 2.2208 | 0.4521 | 1.49700 | 81.54 | 0.786 |
| 9* | 2.9006 | d9 | 1. | | 0.722 |
| 10 | 6.3327 | 0.3000 | 1.83400 | 37.16 | 0.650 |
| 11 | 1.1384 | 1.1031 | 1.64769 | 33.79 | 0.614 |
| 12 | −9.1597 | 0.1000 | 1. | | 0.598 |
| 13 (Stop) | ∞ | 0.1000 | 1. | | 0.590 |
| 14 | 2.4331 | 0.4109 | 1.81600 | 46.62 | 0.624 |
| 15 | 1.4835 | 0.6873 | 1.49700 | 81.54 | 0.615 |
| 16 | −1.5523 | 0.1000 | 1. | | 0.650 |
| 17 | −1.7693 | 0.3000 | 1.81600 | 46.62 | 0.643 |
| 18 | 4.9222 | 0.5112 | 1.49700 | 81.54 | 0.711 |
| 19 | −5.5507 | 0.1000 | 1. | | 0.795 |
| 20* | 5.0297 | 0.6920 | 1.49700 | 81.54 | 0.850 |
| 21* | −1.8981 | 0.1000 | 1. | | 0.907 |
| 22 | 16.7852 | 0.5780 | 1.83400 | 37.16 | 0.902 |
| 23 | 9.3753 | 0.4930 | 1. | | 0.882 |
| 24 | ∞ | 0.2000 | 1.51633 | 64.14 | 0.890 |
| 25 | ∞ | 0.1000 | 1. | | 0.892 |
| 26 | ∞ | 5.3000 | 1.63854 | 55.38 | 0.894 |
| 27 | ∞ | 0.0856 | 1. | | 0.950 |
| Image plane | ∞ | 0. | | | |

Aspherical surface data
2nd surface
K=−1.0000
A2=0.0000E+00, A4=−1.6360E−02, A6=4.6266E−02, A8=0.0000E+00, A10=0.0000E+00
Aspherical surface data
8th surface
K=0.
A2=0.0000E+00, A4=−5.2/00E−02, A6=5.4101E−02, A8=4.5/65E−03, A10=0.0000E+00

9th surface

K=0.

A2=0.0000E+00, A4=4.9134E-02, A6=6.3791E-02, A8=0.0000E+00, A10=0.0000E+00

20th surface

K=0.

A2=0.0000E+00, A4=5.9779E-03, A6=1.4095E-03, A8=0.0000E+00, A10=0.0000E+00

Aspherical surface data

21st surface

K=0.

A2=0.0000E+00, A4=2.2880E-02, A6=3.2241E-03, A8=0.0000E+00, A10=0.0000E+00

| Various data | | |
|---|---|---|
| | Far Point | Near point |
| OBJ | 13.0000 | 2.4000 |
| FL | 0.80002 | 0.79259 |
| MG | −0.057538 | −0.240455 |
| FNO | 3.6407 | 3.5879 |
| FIM | 0.948 | 0.948 |
| LTL | 15.7036 | 15.7037 |
| FB | 0.03958 | −0.10492 |
| d7 | 0.30000 | 0.98746 |
| d9 | 1.24011 | 0.55265 |
| β1 | 0.06093 | 0.24500 |
| β2 | 1.11789 | 1.16191 |
| β3 | −0.84467 | −0.84469 |

Unit focal length
f1=−0.85974, f2=15.61736, f3=2.99266

Example 2

Unit mm

| Surface data | | | | | |
|---|---|---|---|---|---|
| Surface no. | r | d | nd | vd | ER |
| Object plane | ∞ | 16.0000 | 1. | | |
| 1 | ∞ | 0.2500 | 1.88300 | 40.76 | 1.282 |
| 2* | 0.9612 | 0.6709 | 1. | | 0.877 |
| 3 | ∞ | 0.4000 | 1.49400 | 75.01 | 0.833 |
| 4 | ∞ | 0.1500 | 1. | | 0.782 |
| 5 | −5.5346 | 0.2500 | 1.77250 | 49.60 | 0.764 |
| 6 | 2.4020 | 0.4500 | 1.95906 | 17.47 | 0.745 |
| 7 | −15.4746 | d7 | 1. | | 0.724 |
| 8* | 8.6565 | 0.5000 | 1.74320 | 49.34 | 0.659 |
| 9* | 51.2636 | d9 | 1. | | 0.628 |
| 10 | 2.9556 | 0.4161 | 1.65160 | 58.55 | 0.560 |
| 11 | −8.3048 | 0.1000 | 1. | | 0.399 |
| 12 (Stop) | ∞ | 0.1000 | 1. | | 0.366 |
| 13 | −1.5648 | 0.2500 | 1.88300 | 40.76 | 0.377 |
| 14 | 2.2526 | 0.4000 | 1.49700 | 81.54 | 0.462 |
| 15 | −1.5310 | 0.2000 | 1. | | 0.560 |
| 16 | −37.1740 | 0.7000 | 1.49700 | 81.54 | 0.680 |
| 17 | −1.2180 | 0.3360 | 1.77250 | 49.60 | 0.789 |
| 18 | −1.9323 | 0.2000 | 1. | | 0.923 |
| 19 | 6.2625 | 0.5000 | 1.49700 | 81.54 | 1.027 |
| 20 | −3.2562 | 0.6500 | 1. | | 1.045 |
| 21 | ∞ | 0.2000 | 1.51633 | 64.14 | 0.999 |
| 22 | ∞ | 0.2030 | 1. | | 0.991 |
| 23 | ∞ | 4.3000 | 1.63854 | 55.38 | 0.980 |
| 24 | ∞ | 0.3500 | 1.51633 | 64.14 | 0.831 |
| 25 | ∞ | 0.0444 | 1. | | 0.818 |
| Image plane | ∞ | 0. | | | |

Aspherical surface data

2nd surface

K=0.4160

A2=0.0000E+00, A4=8.4650E-02, A6=1.3557E-01, A8=1.2736E-01, A10=3.9760E-02, A12=1.2666E-09, A14=0.0000E+00, A16=0.0000E+00, A18=0.0000E+00, A20=0.0000E+00

8th surface

K=0.

A2=0.0000E+00, A4=4.4332E-02, A6=0.0000E+00, A8=0.0000E+00, A10=0.0000E+00

9th surface

K=0.

A2=0.0000E+00, A4=−6.7341E-02, A6=0.0000E+00, A8=0.0000E+00, A10=0.0000E+00

| Various data | | |
|---|---|---|
| | Far Point | Near point |
| OBJ | 16.0000 | 2.5000 |
| FL | 0.75025 | 0.72600 |
| MG | −0.044343 | −0.212650 |
| FNO | 3.6905 | 3.6648 |
| FIM | 0.812 | 0.812 |
| LTL | 13.0974 | 13.0974 |
| FB | 0.01109 | −0.11003 |
| d7 | 0.42707 | 1.09071 |
| d9 | 1.05000 | 0.38636 |
| β1 | 0.06595 | 0.30490 |
| β2 | 1.27724 | 1.32483 |
| β3 | −0.52644 | −0.52644 |

Unit focal length
f1=−1.13600, f2=13.94442, f3=2.57607

Example 3

Unit mm

| Surface data | | | | | |
|---|---|---|---|---|---|
| Surface no. | r | d | nd | vd | ER |
| Object plane | ∞ | 16.0000 | 1. | | |
| 1 | ∞ | 0.2500 | 1.88300 | 40.76 | 1.264 |
| 2* | 0.9272 | 1.1000 | 1. | | 0.857 |
| 3 | ∞ | 0.4000 | 1.49400 | 75.01 | 0.751 |
| 4 | ∞ | d4 | 1. | | 0.708 |
| 5* | −9.5539 | 0.6179 | 1.88300 | 40.76 | 0.626 |
| 6* | −6.5358 | d6 | 1. | | 0.620 |
| 7 | 4.3878 | 0.4161 | 1.95906 | 17.47 | 0.560 |
| 8 | −3.3352 | 0.1000 | 1. | | 0.439 |
| 9 (Stop) | ∞ | 0.1000 | 1. | | 0.390 |
| 10 | −1.5583 | 0.2500 | 1.88300 | 40.76 | 0.393 |
| 11 | 2.0000 | 0.5400 | 1.48749 | 70.23 | 0.453 |
| 12 | −1.3000 | 0.1000 | 1. | | 0.560 |
| 13 | −5.7457 | 0.8000 | 1.49700 | 81.54 | 0.610 |
| 14 | −1.2000 | 0.2500 | 1.84666 | 23.78 | 0.730 |
| 15 | −4.2732 | 0.1000 | 1. | | 0.854 |
| 16* | 5.3140 | 0.9434 | 1.49700 | 81.54 | 0.956 |
| 17* | −1.5831 | 0.6500 | 1. | | 1.054 |
| 18 | ∞ | 0.2000 | 1.51633 | 64.14 | 0.997 |
| 19 | ∞ | 0.2000 | 1. | | 0.989 |

-continued

Surface data

| Surface no. | r | d | nd | vd | ER |
|---|---|---|---|---|---|
| 20 | ∞ | 4.3000 | 1.63854 | 55.38 | 0.978 |
| 21 | ∞ | 0.3500 | 1.51633 | 64.14 | 0.831 |
| 22 | ∞ | 0.0420 | 1. | | 0.818 |

Image plane ∞0.

Aspherical surface data

2nd surface

K=−0.3786

A2=0.0000E+00, A4=4.8645E−02, A6=5.8716E−02, A8=7.4460E−02, A10=1.7666E−02, A12=−1.2683E−09, A14=0.0000E+00, A16=0.0000E+00, A18=0.0000E+00, A20=0.0000E+00

5th surface

K=0.

A2=0.0000E+00, A4=4.5962E−02, A6=0.0000E+00, A8=0.0000E+00, A10=0.0000E+00

6th surface

K=0.

A2=0.0000E+00, A4=5.7654E−02, A6=0.0000E+00, A8=0.0000E+00, A10=0.0000E+00

16th surface

K=0.

A2=0.0000E+00, A4=−1.9531E−02, A6=5.2759E−03, A8=−3.6036E−04, A10=0.0000E+00

17th surface

K=0.

A2=0.0000E+00, A4=1.9479E−02, A6=1.3298E−03, A8=4.9924E−03, A10=0.0000E+00

Various data

| | Far Point | Near point |
|---|---|---|
| OBJ | 16.0000 | 2.5000 |
| FL | 0.75052 | 0.72372 |
| MG | −0.044403 | −0.212614 |
| FNO | 3.7116 | 3.6936 |
| FIM | 0.812 | 0.812 |
| LTL | 13.2865 | 13.2865 |
| FB | 0.00868 | −0.11186 |
| d4 | 0.53174 | 1.21609 |
| d6 | 1.04533 | 0.36098 |
| β1 | 0.06111 | 0.28511 |
| β2 | 1.21847 | 1.25048 |
| β3 | −0.59635 | −0.59635 |

Unit focal length f1=−1.05000, f2=21.37800, f3=2.80754

Example 4

Unit mm

Surface data

| Surface no. | r | d | nd | vd | ER |
|---|---|---|---|---|---|
| Object plane | ∞ | 16.0000 | 1. | | |
| 1 | ∞ | 0.2500 | 1.88300 | 40.76 | 1.241 |
| 2* | 0.8793 | 0.9000 | 1. | | 0.836 |
| 3 | −13.0485 | 0.2500 | 1.88300 | 40.76 | 0.762 |
| 4 | 1.8000 | 0.6000 | 1.69895 | 30.13 | 0.736 |
| 5 | −7.4550 | 0.1000 | 1. | | 0.727 |
| 6 | ∞ | 0.4000 | 1.49400 | 75.01 | 0.710 |

-continued

Surface data

| Surface no. | r | d | nd | vd | ER |
|---|---|---|---|---|---|
| 7 | ∞ | d7 | 1. | | 0.685 |
| 8 | 1.6909 | 0.6500 | 1.53172 | 48.84 | 0.645 |
| 9 | 1.9976 | d9 | 1. | | 0.536 |
| 10 (Stop) | ∞ | 0.1000 | 1. | | 0.436 |
| 11 | 2.7616 | 0.5000 | 1.76182 | 26.52 | 0.479 |
| 12 | −1.2000 | 0.2500 | 1.88300 | 40.76 | 0.509 |
| 13 | 2.5713 | 0.1500 | 1. | | 0.557 |
| 14 | 6.2066 | 0.7000 | 1.53172 | 48.84 | 0.613 |
| 15 | −1.9348 | 0.1000 | 1. | | 0.740 |
| 16 | −33.0278 | 0.7000 | 1.49700 | 81.54 | 0.791 |
| 17 | −1.5927 | 0.2500 | 1.95906 | 17.47 | 0.857 |
| 18 | −3.4446 | 0.1000 | 1. | | 0.950 |
| 19 | 8.2079 | 0.7457 | 1.49700 | 81.54 | 1.016 |
| 20 | −2.6637 | 0.6500 | 1. | | 1.063 |
| 21 | ∞ | 0.2000 | 1.51633 | 64.14 | 1.010 |
| 22 | ∞ | 0.2000 | 1. | | 1.002 |
| 23 | ∞ | 4.3000 | 1.63854 | 55.38 | 0.989 |
| 24 | ∞ | 0.3500 | 1.51633 | 64.14 | 0.829 |
| 25 | ∞ | 0.0452 | 1. | | 0.815 |
| Image plane | ∞ | 0. | | | |

Aspherical surface data

2nd surface

K=−3.7635

A2=0.0000E+00, A4=5.12/8E−01, A6=−4.9820E−01, A8=5.0168E−01, A10=−2.0428E−01, A12=2.2569E−08, A14=0.0000E+00, A16=0.0000E+00, A18=0.0000E+00, A20=0.0000E+00

Various data

| | Far Point | Near point |
|---|---|---|
| OBJ | 16.0000 | 2.5000 |
| FL | 0.75014 | 0.74690 |
| MG | −0.044500 | −0.223334 |
| FNO | 3.7097 | 3.6824 |
| FIM | 0.812 | 0.812 |
| LTL | 13.8280 | 13.8280 |
| FB | 0.01182 | −0.12161 |
| d7 | 0.26174 | 0.92454 |
| d9 | 1.07533 | 0.41253 |
| β1 | 0.05298 | 0.25362 |
| β2 | 1.14594 | 1.20148 |
| β3 | −0.73293 | −0.73293 |

Unit focal length f1=−0.90415, f2=11.93355, f3=2.72360

Example 5

Unit mm

Surface data

| Surface no. | r | d | nd | vd | ER |
|---|---|---|---|---|---|
| Object plane | ∞ | 15.8000 | 1. | | |
| 1 | ∞ | 0.2500 | 1.88300 | 40.76 | 1.298 |
| 2* | 1.1014 | 0.7055 | 1. | | 0.910 |
| 3 | 4.9262 | 0.2500 | 1.88300 | 40.76 | 0.812 |
| 4 | 2.2000 | d4 | 1. | | 0.743 |
| 5 | ∞ | 0.4000 | 1.49400 | 75.01 | 0.690 |
| 6 | ∞ | 0.1000 | 1. | | 0.674 |
| 7* | 1.8277 | 0.5170 | 1.51633 | 64.14 | 0.660 |
| 8* | 2.3331 | d8 | 1. | | 0.590 |
| 9 | 4.0162 | 0.4161 | 1.95906 | 17.47 | 0.560 |
| 10 | −3.2257 | 0.1000 | 1. | | 0.448 |

-continued

Surface data

| Surface no. | r | d | nd | vd | ER |
|---|---|---|---|---|---|
| 11 (Stop) | ∞ | 0.1000 | 1. | | 0.400 |
| 12 | −1.5381 | 0.2500 | 1.88300 | 40.76 | 0.398 |
| 13 | 2.2458 | 0.5400 | 1.48749 | 70.23 | 0.457 |
| 14 | −1.3000 | 0.2000 | 1. | | 0.560 |
| 15 | −9.0844 | 0.8000 | 1.49700 | 81.54 | 0.638 |
| 16 | −1.2998 | 0.2500 | 1.84666 | 23.78 | 0.751 |
| 17 | −5.5081 | 0.1000 | 1. | | 0.870 |
| 18* | 3.9469 | 0.9447 | 1.49700 | 81.54 | 0.986 |
| 19* | −1.6844 | 0.6500 | 1. | | 1.058 |
| 20 | ∞ | 0.2000 | 1.51633 | 64.14 | 1.001 |
| 21 | ∞ | 0.2000 | 1. | | 0.993 |
| 22 | ∞ | 4.3000 | 1.63854 | 55.38 | 0.981 |
| 23 | ∞ | 0.3500 | 1.51633 | 64.14 | 0.828 |
| 24 | ∞ | 0.0428 | 1. | | 0.814 |
| Image plane | ∞ | 0. | | | |

Aspherical surface data

2nd surface $K=-2.2853$ $A2=0.0000E+00$, $A4=1.3338E-01$, $A6=2.5305E-02$, $A8=-4.2323E-02$, $A10=2.6226E-02$, $A12=-1.2684E-09$, $A14=0.0000E+00$, $A16=0.0000E+00$, $A18=0.0000E+00$, $A20=0.0000E+00$ 7th surface $K=0.$ $A2=0.0000E+00$, $A4=-6.4410E-02$, $A6=0.0000E+00$, $A8=0.0000E+00$, $A10=0.0000E+00$ 8th surface $K=0.$ $A2=0.0000E+00$, $A4=-9.2071E-02$, $A6=0.0000E+00$, $A8=0.0000E+00$, $A10=0.0000E+00$ 18th surface $K=0.$ $A2=0.0000E+00$, $A4=-1.3990E-02$, $A6=1.2717E-02$, $A8=1.9476E-04$, $A10=0.0000E+00$ 19th surface $K=0.$ $A2=0.0000E+00$, $A4=2.4646E-02$, $A6=4.1843E-03$, $A8=7.753/E-03$, $A10=0.0000E+00$ Various data

| | Far Point | Near point |
|---|---|---|
| OBJ | 15.8000 | 2.6200 |
| FL | 0.75036 | 0.74853 |
| MG | −0.044776 | −0.209826 |
| FNO | 3.6332 | 3.6154 |
| FIM | 0.812 | 0.812 |
| LTL | 13.2903 | 13.2903 |
| FB | 0.00925 | −0.11422 |
| d4 | 0.60084 | 1.19477 |
| d8 | 1.02333 | 0.42940 |
| β1 | 0.05010 | 0.22503 |
| β2 | 1.13061 | 1.17962 |
| β3 | −0.79044 | −0.79044 |

Unit focal length $f1=-0.84949$, $f2=12.12002$, $f3=2.73833$

Example 6

Unit mm

Surface data

| Surface no. | r | d | nd | vd | ER |
|---|---|---|---|---|---|
| Object plane | ∞ | 15.0000 | 1. | | |
| 1 | ∞ | 0.2500 | 1.88300 | 40.76 | 1.270 |
| 2* | 0.7856 | 0.6500 | 1. | | 0.838 |
| 3 | ∞ | 0.4000 | 1.49400 | 75.01 | 0.824 |
| 4 | ∞ | d4 | 1. | | 0.800 |
| 5* | 1.9309 | 0.4597 | 1.49700 | 81.54 | 0.766 |
| 6 | 2.8631 | d6 | 1. | | 0.685 |
| 7 | 8.2193 | 0.5563 | 1.72825 | 28.46 | 0.492 |
| 8 | −0.8058 | 0.3000 | 1.81600 | 46.62 | 0.453 |
| 9 | −2.4732 | 0.1000 | 1. | | 0.430 |
| 10 (Stop) | ∞ | 0.6013 | 1. | | 0.395 |
| 11 | 9.1375 | 0.4871 | 1.49700 | 81.54 | 0.517 |
| 12 | −2.2107 | 0.2570 | 1.80518 | 25.42 | 0.562 |
| 13 | 1.6710 | 0.6818 | 1.49700 | 81.54 | 0.623 |
| 14 | −1.7198 | 0.1000 | 1. | | 0.728 |
| 15* | 2.9755 | 0.5709 | 1.49700 | 81.54 | 0.800 |
| 16 | −5.8213 | 0.6000 | 1. | | 0.818 |
| 17 | ∞ | 3.2000 | 1.88300 | 40.76 | 0.816 |
| 18 | ∞ | 0.3000 | 1.51633 | 64.14 | 0.812 |
| 19 | ∞ | 0.0263 | 1. | | 0.812 |
| Image plane | ∞ | 0. | | | |

Aspherical surface data

2nd surface $K=-1.0000$ $A2=0.0000E+00$, $A4=3.5380E-02$, $A6=2.5/84E-02$, $A8=7.1050E-02$, $A10=0.0000E+00$ 5th surface $K=0.$ $A2=0.0000E+00$, $A4=-1.5830E-02$, $A6=4.2282E-02$, $A8=1.6255E-02$, $A10=0.0000E+00$ 15th surface $K=0.$ $A2=0.0000E+00$, $A4=2.1314E-03$, $A6=1.0242E-02$, $A8=0.0000E+00$, $A10=0.0000E+00$ Various data

| | Far Point | Near point |
|---|---|---|
| OBJ | 15.0000 | 1.7300 |
| FL | 0.70373 | 0.69457 |
| MG | −0.044525 | −0.275741 |
| FNO | 3.6056 | 3.5439 |
| FIM | 0.812 | 0.812 |
| LTL | 11.0387 | 11.0387 |
| FB | −0.00508 | −0.16527 |
| d4 | 0.26500 | 1.03032 |
| d6 | 1.23330 | 0.46798 |
| β1 | 0.05553 | 0.32325 |
| β2 | 1.16820 | 1.24284 |
| β3 | −0.68635 | −0.68635 |

Unit focal length $f1=-0.88975$, $f2=10.25404$, $f3=2.38964$

Example 7

Unit mm

| Surface no. | r | d | nd | vd | ER |
|---|---|---|---|---|---|
| Object plane | ∞ | 20.0000 | 1. | | |
| 1 | ∞ | 0.2500 | 1.88300 | 40.76 | 1.304 |
| 2 | 1.1969 | 0.5230 | 1. | | 0.936 |
| 3 | ∞ | 0.4000 | 1.49400 | 75.01 | 0.881 |
| 4 | ∞ | 0.1000 | 1. | | 0.784 |
| 5 | −14.1887 | 0.2500 | 1.88300 | 40.76 | 0.750 |
| 6 | 3.1892 | d6 | 1. | | 0.697 |
| 7* | 2.6326 | 0.4906 | 1.51633 | 64.14 | 0.655 |
| 8* | 4.1921 | d8 | 1. | | 0.603 |
| 9 | −2.4500 | 0.7844 | 1.88300 | 40.76 | 0.500 |
| 10 | −8.9678 | 0.1000 | 1. | | 0.546 |
| 11 | 1.8948 | 0.3500 | 1.58144 | 40.75 | 0.560 |
| 12 | 20.9186 | 0.1000 | 1. | | 0.549 |
| 13 (Stop) | ∞ | 0.1000 | 1. | | 0.550 |
| 14 | 1.8313 | 0.5142 | 1.72825 | 28.46 | 0.560 |
| 15 | −1.6911 | 0.6836 | 1.88300 | 40.76 | 0.549 |
| 16* | 1.9299 | 0.2109 | 1. | | 0.560 |
| 17 | 2.3041 | 0.6736 | 1.49700 | 81.54 | 0.652 |
| 18 | −1.4862 | 0.2853 | 1.88300 | 40.76 | 0.713 |
| 19 | −25.9918 | 0.1000 | 1. | | 0.817 |
| 20 | 2.7755 | 0.9730 | 1.49700 | 81.54 | 0.934 |
| 21 | −1.6000 | 0.2500 | 1.92286 | 18.90 | 0.993 |
| 22 | −2.6855 | 0.1000 | 1. | | 1.089 |
| 23* | 7.2385 | 0.6621 | 1.49700 | 81.54 | 1.129 |
| 24* | −3.6160 | 0.6500 | 1. | | 1.149 |
| 25 | ∞ | 0.2000 | 1.51633 | 64.14 | 1.080 |
| 26 | ∞ | 0.1900 | 1. | | 1.069 |
| 27 | ∞ | 4.3000 | 1.63854 | 55.38 | 1.054 |
| 28 | ∞ | 0.3500 | 1.51633 | 64.14 | 0.837 |
| 29 | ∞ | 0.0464 | 1. | | 0.818 |
| Image plane | ∞ | 0. | | | |

Aspherical surface data

2nd surface

K=0.1809

A2=0.0000E+00, A4=−6.5666E−02, A6=−9.9331E−02, A8=1.3138E−01, A10=−1.1544E−01, A12=4.6840E−05, A14=0.0000E+00, A16=0.0000E+00, A18=0.0000E+00, A20=0.0000E+00

7th surface

K=0.

A2=0.0000E+00, A4=−1.260/E−01, A6=0.0000E+00, A8=0.0000E+00, A10=0.0000E+00

8th surface

K=0.

A2=0.0000E+00, A4=−1.1353E−01, A6=0.0000E+00, A8=0.0000E+00, A10=0.0000E+00

16th surface

K=−5.7627

A2=0.0000E+00, A4=1.5242E−01, A6=−1.8344E−02, A8=0.0000E+00, A10=0.0000E+00

23th surface

K=0.

A2=0.0000E+00, A4=−2.7365E−02, A6=5.7805E−03, A8=0.0000E+00, A10=0.0000E+00

24th surface

K=0.

A2=0.0000E+00, A4=−6.8530E−03, A6=5.7331E−03, A8=0.0000E+00, A10=0.0000E+00

| | Various data | |
|---|---|---|
| | Far Point | Near point |
| OBJ | 20.0000 | 2.7000 |
| FL | 0.75014 | 0.75236 |
| MG | −0.035750 | −0.204777 |
| FNO | 3.6726 | 3.6658 |
| FIM | 0.812 | 0.812 |
| LTL | 15.0265 | 15.0265 |
| FB | 0.01960 | −0.10765 |
| d6 | 0.39113 | 0.94749 |
| d8 | 0.99828 | 0.44192 |
| β1 | 0.03555 | 0.19570 |
| β2 | 1.10738 | 1.15232 |
| β3 | −0.90809 | −0.90809 |

Unit focal length f1=−0.7515%, f2=12.37976, f3=3.00572

Example 8

Unit mm

| Surface no. | r | d | nd | vd | ER |
|---|---|---|---|---|---|
| Object plane | ∞ | 22.0000 | 1. | | |
| 1 | ∞ | 0.2500 | 1.88300 | 40.76 | 1.300 |
| 2* | 1.1937 | 0.5429 | 1. | | 0.933 |
| 3 | ∞ | 0.4000 | 1.49400 | 75.01 | 0.877 |
| 4 | ∞ | 0.1000 | 1. | | 0.785 |
| 5 | ∞ | 0.2500 | 1.88300 | 40.76 | 0.750 |
| 6 | 2.4860 | d6 | 1. | | 0.686 |
| 7* | 2.6512 | 0.4886 | 1.51633 | 64.14 | 0.652 |
| 8* | 4.1408 | d8 | 1. | | 0.607 |
| 9 | −10.0924 | 0.7107 | 1.81600 | 46.62 | 0.543 |
| 10 | 5.6745 | 0.6175 | 1.54814 | 45.79 | 0.541 |
| 11 | −3.2760 | 0.1000 | 1. | | 0.549 |
| 12 (Stop) | ∞ | 0.1000 | 1. | | 0.541 |
| 13 | 1.7391 | 0.8527 | 1.69895 | 30.13 | 0.560 |
| 14 | −1.9645 | 0.2891 | 1.81600 | 46.62 | 0.551 |
| 15 | 1.8083 | 0.2000 | 1. | | 0.560 |
| 16 | 3.4408 | 0.7985 | 1.49700 | 81.54 | 0.710 |
| 17 | −1.9495 | 0.2500 | 1.88300 | 40.76 | 0.735 |
| 18 | −4.8688 | 0.1000 | 1. | | 0.809 |
| 19 | 4.1440 | 0.8767 | 1.49700 | 81.54 | 0.883 |
| 20 | −1.7027 | 0.2500 | 1.84666 | 23.78 | 0.935 |
| 21 | −6.8733 | 0.1000 | 1. | | 1.026 |
| 22* | 5.6133 | 0.8858 | 1.49700 | 81.54 | 1.092 |
| 23* | −2.3000 | 0.6500 | 1. | | 1.149 |
| 24 | ∞ | 0.2000 | 1.51633 | 64.14 | 1.075 |
| 25 | ∞ | 0.1800 | 1. | | 1.064 |
| 26 | ∞ | 4.3000 | 1.63854 | 55.38 | 1.050 |
| 27 | ∞ | 0.3500 | 1.51633 | 64.14 | 0.840 |
| 28 | ∞ | 0.0497 | 1. | | 0.822 |
| Image plane | ∞ | 0. | | | |

Aspherical surface data

2nd surface

K=−0.1405

A2=0.0000E+00, A4=−6.3105E−02, A6=4.0405E−02, A8=−4.5/30E−02, A10=4.2020E−03, A12=4.6840E−05, A14=0.0000E+00, A16=0.0000E+00, A18=0.0000E+00, A20=0.0000E+00

7th surface

K=−13.9021

A2=0.0000E+00, A4=−3.0044E−02, A6=−5.5844E−02, A8=0.0000E+00, A10=0.0000E+00

8th surface

K=−33.7333

A2=0.0000E+00, A4=−5.5130E−02, A6=−1.5208E−02, A8=−1.9281E−02, A10=0.0000E+00

22nd surface
K=0.
A2=0.0000E+00, A4=−1.1313E−02, A6=0.0000E+00, A8=0.0000E+00, A10=0.0000E+00
23rd surface
K=0.
A2=0.0000E+00, A4=1.2548E−02, A6=−1.3517E−04, A8=0.0000E+00, A10=0.0000E+00

Various data

|  | Far Point | Near point |
|---|---|---|
| OBJ | 22.0000 | 2.7000 |
| FL | 0.75029 | 0.75440 |
| MG | −0.032633 | −0.204826 |
| FNO | 3.6486 | 3.6448 |
| FIM | 0.812 | 0.812 |
| LTL | 15.2613 | 15.2613 |
| FB | 0.02521 | −0.10483 |
| d6 | 0.40585 | 0.97313 |
| d8 | 0.96324 | 0.39595 |
| β1 | 0.03157 | 0.19051 |
| β2 | 1.09942 | 1.14360 |
| β3 | −0.94012 | −0.94012 |

Unit focal length
f1=−0.73041, f2=12.83960, f3=3.20872

Example 9

Unit mm

Surface data

| Surface no. | r | d | nd | vd | ER |
|---|---|---|---|---|---|
| Object plane | ∞ | 18.0000 | 1. |  |  |
| 1 | ∞ | 0.2500 | 1.88300 | 40.76 | 1.305 |
| 2* | 1.0490 | 0.9609 | 1. |  | 0.916 |
| 3 | ∞ | 0.2500 | 1.83400 | 37.16 | 0.750 |
| 4 | 2.9201 | d4 | 1. |  | 0.691 |
| 5* | 1.8022 | 0.4386 | 1.49700 | 81.54 | 0.650 |
| 6* | 2.4247 | d6 | 1. |  | 0.604 |
| 7 | ∞ | 1.0000 | 1.49400 | 75.01 | 0.550 |
| 8 | ∞ | 0.2338 | 1. |  | 0.513 |
| 11 (Stop) | ∞ | 0.1000 | 1. |  | 0.503 |
| 10 | 1.8323 | 0.6035 | 1.76182 | 26.52 | 0.560 |
| 11 | −1.3953 | 0.3644 | 1.81600 | 46.62 | 0.546 |
| 12 | 1.8982 | 0.2730 | 1. |  | 0.560 |
| 13 | 2.5712 | 0.7054 | 1.49700 | 81.54 | 0.675 |
| 14 | −1.3610 | 0.2500 | 1.80518 | 25.42 | 0.737 |
| 15 | −3.7471 | 0.1000 | 1. |  | 0.825 |
| 16 | 3.6004 | 0.6856 | 1.43875 | 94.66 | 0.898 |
| 17 | −2.5684 | 0.2500 | 1.80518 | 25.42 | 0.930 |
| 18 | ∞ | 0.1000 | 1. |  | 0.989 |
| 19* | 3.5622 | 0.8149 | 1.43875 | 94.66 | 1.048 |
| 20* | −2.0300 | 0.6500 | 1. |  | 1.094 |
| 21 | ∞ | 0.2000 | 1.51633 | 64.14 | 1.031 |
| 22 | ∞ | 0.1800 | 1. |  | 1.022 |
| 23 | ∞ | 4.3000 | 1.63854 | 55.38 | 1.010 |
| 24 | ∞ | 0.3500 | 1.51633 | 64.14 | 0.836 |
| 25 | ∞ | 0.0518 | 1. |  | 0.820 |
| Image plane | ∞ | 0. |  |  |  |

Aspherical surface data
2nd surface
K=−4.6518
A2=0.0000E+00, A4=3.5553E−01, A6=−3.7848E−01, A8=4.1948E−01, A10=−3.1048E−01, A12=1.06/4E−01, A14=0.0000E+00, A16=0.0000E+00, A18=0.0000E+00, A20=0.0000E+00

5th surface
K=0.
A2=0.0000E+00, A4=−1.1803E−01, A6=−3.8081E−02, A8=0.0000E+00, A10=0.0000E+00
6th surface
K=0.
A2=0.0000E+00, A4=−1.0644E−01, A6=−4.1513E−02, A8=0.0000E+00, A10=0.0000E+00
19th surface
K=0.
A2=0.0000E+00, A4=−2.5373E−02, A6=0.0000E+00, A8=0.0000E+00, A10=0.0000E+00
20th surface
K=0.
A2=0.0000E+00, A4=2.0486E−02, A6=0.0000E+00, A8=0.0000E+00, A10=0.0000E+00

Various data

|  | Far Point | Near point |
|---|---|---|
| OBJ | 18.0000 | 2.5000 |
| FL | 0.71645 | 0.72316 |
| MG | −0.037821 | −0.210608 |
| FNO | 3.6623 | 3.6500 |
| FIM | 0.812 | 0.812 |
| LTL | 14.5404 | 14.5404 |
| FB | 0.02475 | −0.10045 |
| d4 | 0.39000 | 0.94593 |
| d6 | 1.03852 | 0.48259 |
| β1 | 0.03768 | 0.20097 |
| β2 | 1.10187 | 1.15044 |
| β3 | −0.91093 | −0.91093 |

Unit focal length
f1=−0.71883, f2=11.44611, f3=3.09757

Example 10

Unit mm

Surface data

| Surface no. | r | d | nd | vd | ER |
|---|---|---|---|---|---|
| Object plane | ∞ | 20.0000 | 1. |  |  |
| 1 | ∞ | 0.2500 | 1.88300 | 40.76 | 1.403 |
| 2* | 1.3766 | 0.5408 | 1. |  | 1.007 |
| 3 | ∞ | 0.4000 | 1.49400 | 75.01 | 0.947 |
| 4 | ∞ | 0.1000 | 1. |  | 0.839 |
| 5 | −8.1026 | 0.4350 | 1.88300 | 40.76 | 0.940 |
| 6 | 2.8146 | d6 | 1. |  | 0.725 |
| 7* | 2.6512 | 0.4886 | 1.51633 | 64.14 | 0.700 |
| 8* | 4.1408 | d8 | 1. |  | 0.669 |
| 9 | −10.0924 | 0.7107 | 1.81600 | 46.62 | 0.583 |
| 10 | 5.6745 | 0.6175 | 1.54814 | 45.79 | 0.564 |
| 11 | −3.2760 | 0.1000 | 1. |  | 0.558 |
| 12 (Stop) | ∞ | 0.1000 | 1. |  | 0.550 |
| 13 | 1.7391 | 0.8527 | 1.69895 | 30.13 | 0.560 |
| 14 | −1.9645 | 0.2891 | 1.81600 | 46.62 | 0.551 |
| 15 | 1.8083 | 0.2000 | 1. |  | 0.560 |
| 16 | 3.4408 | 0.7985 | 1.49700 | 81.54 | 0.710 |
| 17 | −1.9495 | 0.2500 | 1.88300 | 40.76 | 0.736 |
| 18 | −4.8688 | 0.1000 | 1. |  | 0.810 |
| 19 | 4.1440 | 0.8767 | 1.49700 | 81.54 | 0.884 |
| 20 | −1.7027 | 0.2500 | 1.84666 | 23.78 | 0.936 |
| 21 | −6.8733 | 0.1000 | 1. |  | 1.028 |
| 22* | 5.6133 | 0.8858 | 1.49700 | 81.54 | 1.094 |
| 23* | −2.3000 | 0.6500 | 1. |  | 1.151 |

-continued

Surface data

| Surface no. | r | d | nd | vd | ER |
|---|---|---|---|---|---|
| 24 | ∞ | 0.2000 | 1.51633 | 64.14 | 1.076 |
| 25 | ∞ | 0.1800 | 1. | | 1.066 |
| 26 | ∞ | 4.3000 | 1.63854 | 55.38 | 1.051 |
| 27 | ∞ | 0.3500 | 1.51633 | 64.14 | 0.842 |
| 28 | ∞ | 0.0531 | 1. | | 0.824 |
| Image plane | ∞ | 0. | | | |

Aspherical surface data

2nd surface
K=0.2119
A2=0.0000E+00, A4=−5.0/45E−02, A6=9.5398E−03, A8=−8.6284E−03, A10=−1.2475E−02, A12=−4.0707E−04, A14=0.0000E+00, A16=0.0000E+00, A18=0.0000E+00, A20=0.0000E+00

7th surface
K=−13.9021
A2=0.0000E+00, A4=−3.0044E−02, A6=−5.5844E−02, A8=0.0000E+00, A10=0.0000E+00

8th surface
K=−33.7333
A2=0.0000E+00, A4=−5.5130E−02, A6=−1.5208E−02, A8=−1.9281E−02, A10=0.0000E+00

22nd surface
K=0.
A2=0.0000E+00, A4=−1.1313E−02, A6=0.0000E+00, A8=0.0000E+00, A10=0.0000E+00

23rd surface
K=0.
A2=0.0000E+00, A4=1.2548E−02, A6=−1.3517E−04, A8=0.0000E+00, A10=0.0000E+00

Various data

| | Far Point | Near point |
|---|---|---|
| OBJ | 20.0000 | 2.7000 |
| FL | 0.75032 | 0.75450 |
| MG | −0.035629 | −0.201141 |
| FNO | 3.6403 | 3.6358 |
| FIM | 0.812 | 0.812 |
| LTL | 15.4477 | 15.4477 |
| FB | 0.02640 | −0.09862 |
| d6 | 0.40585 | 0.95462 |
| d8 | 0.96324 | 0.41446 |
| β1 | 0.03444 | 0.18716 |
| β2 | 1.09912 | 1.14186 |
| β3 | −0.94119 | −0.94119 |

Unit Focal Length
f1=−0.73021, f2=12.83960, f3=3.2872

Next, values of conditional expressions in each example are given below. '-' (hyphen) indicate that there is no corresponding arrangement.

| | Example 1 | Example 2 | Example 3 |
|---|---|---|---|
| (1) fL/Rsp | 0.12633158 | 0.25384017 | 0.17104699 |
| (2) ΣDpc/fL | 3.87653912 | 2.88715356 | 3.07265224 |
| (3) ΣD3/fL | 6.35297874 | 4.26802896 | 4.79604325 |
| (4) $1/r_1 - 1/r_2$ | 0.26708441 | 0.01410856 | 0.12750581 |
| | | | 0.05997346 |
| (5) $1/f_{3x} - 10 \times fL$ | −0.0828932 | −0.4679049 | −0.4032266 |
| | | | −0.3068069 |
| (6) β3F | −0.8446714 | −0.5264441 | −0.5963461 |
| (7) $f_3/fL$ | 3.74072703 | 3.43361518 | 3.74079101 |
| (8) $fL/f_{31}$ | 0.03368378 | 0.22099325 | 0.36984182 |
| (9) $(_an_{SNi}' - _an_{SNi})/_ar_{SNi}$ | 0.33537462 | 0.22046285 | 0.28755697 |
| (10) $(_bn_{SNi}' - _bn_{SNi})/_br_{SNi}$ | −0.4611993 | −0.2261905 | −0.2913833 |
| (11) $f_{3R}/fL$ | 3.58478538 | 5.84738421 | 3.42549166 |
| (12) $(ν_{3RCP} - ν_{3RCN}) - (ν_{3FCP} - ν_{3FCN})$ | 38.29 | −8.84 | 28.29 |
| (13) $fL/r_{SNr}$ | 0.16253301 | −0.6159688 | −0.6254333 |
| (14) $(r_{3XF} - r_{3XR})/(r_{3XF} + r_{3XR})$ | −0.5165847 | 0.01091802 | 0.0903684 |
| (15) $1/r_{3XC} \times r_{3XF}$ | −0.1148257 | −0.2836985 | −0.3208625 |
| (16) $1/r_{3XC} \times r_{3XR}$ | −0.036601 | −0.2899618 | −0.3846154 |
| (17) $ν_{31P} - ν_{32P}$ | −47.75 | −22.99 | −52.76 |
| (18) $ν_{33P} - (ν_{31P} + ν_{32P})/2$ | 23.875 | 11.495 | 37.69 |
| (19) $ν_{31N} - ν_{32N}$ | −9.46 | −8.84 | 16.98 |
| (20) $(R21F + R21R)/(R21F - R21R)$ | −7.5336864 | −1.4063407 | 5.33106922 |
| (21) D21/fL | 0.56511087 | 0.66644452 | 0.82329585 |
| (22) β2F | 1.11789 | 1.27724 | 1.21847 |
| (23) β2N/β2F | 1.03937776 | 1.03726003 | 1.02627065 |
| (24) $(1 - β2F^2) \times β3F^2$ | 0.21089556 | 0.33236369 | 0.28903244 |
| (25) $(1 - β2N^2) \times β3N^2$ | 0.29567094 | 0.39755408 | 0.33616263 |
| (26) $1/r_{LXF} - 1/r_{LXR}$ | −1.0287007 | −1.0403662 | −1.078516 |
| | −0.1480565 | −0.1160595 | |
| (27) SD1/fL | 3.06279843 | 2.89354215 | 0.33310238 |
| (28) fB/fL | 4.99875003 | 5.13308897 | 5.12404733 |
| (29) $fL \times \tan ω_{max}$ | 2.46301838 | 2.28223144 | 2.24501224 |
| $2y_{max}$ | 1.896 | 1.624 | 1.624 |
| (30) ER3 | 0.711 | 0.789 | 0.73 |
| $fL/(2 \times F_{EX})$ | 0.1092625 | 0.10078587 | 0.10084923 |

-continued

|  | Example 4 | Example 5 | Example 6 |
|---|---|---|---|
| (1) fL/Rsp | 0.27163239 | 0.18683333 | 0.08561921 |
| (2) ΣDpc/fL | 3.19940278 | 3.20657679 | 3.27068549 |
| (3) ΣD3/fL | 4.66003651 | 4.93204141 | 5.19295294 |
| (4) $1/r_1 - 1/r_2$ | 0.26003195 | 0.11907798 | |
| | | 0.07147199 | |
| (5) $1/f_{3x} - 10 \times fL$ | −0.1492162 | −0.3893579 | |
| | | −0.2997501 | |
| (6) β3F | −0.7329317 | −0.7904393 | −0.6863543 |
| (7) $f_3/fL$ | 3.63078673 | 3.64935171 | 3.39567989 |
| (8) $fL/f_{31}$ | −0.0940709 | 0.39097541 | 0.21412749 |
| (9) $({}_a n_{SNi}' - {}_a n_{SNi})/{}_a r_{SNi}$ | 0.27586182 | 0.37499231 | 0.32993692 |
| (10) $({}_b n_{SNi}' - {}_b n_{SNi})/{}_b r_{SNi}$ | −0.2901111 | −0.2690106 | −0.1844285 |
| (11) $f_{3R}/fL$ | 5.51990295 | 3.35239085 | 5.7539113 |
| (12) $(\nu_{3RCP} - \nu_{3RCN}) - (\nu_{3FCP} - \nu_{3FCN})$ | 78.31 | 28.29 | 74.28 |
| (13) $fL/r_{SNr}$ | −0.4709864 | −0.5772888 | 0.42114303 |
| (14) $(r_{3XF} - r_{3XR})/(r_{3XF} + r_{3XR})$ | 0.03568415 | 0.08389415 | 0 |
| (15) $1/r_{3XC} \times r_{3XF}$ | −0.3017574 | −0.2894972 | |
| (16) $1/r_{3XC} \times r_{3XR}$ | −0.3240903 | −0.3425197 | |
| (17) $\nu_{31P} - \nu_{32P}$ | −22.32 | −52.76 | −53.08 |
| (18) $\nu_{33P} - (\nu_{31P} + \nu_{32P})/2$ | 43.86 | 37.69 | 26.54 |
| (19) $\nu_{31N} - \nu_{32N}$ | 23.29 | 16.98 | 21.2 |
| (20) (R21F + R21R)/(R21F − R21R) | −12.02641 | −8.232687 | −5.1426732 |
| (21) D21/fL | 0.86650492 | 0.68900261 | 0.65323348 |
| (22) β2F | 1.14594 | 1.13061 | 1.1682 |
| (23) β2N/β2F | 1.04846676 | 1.04334828 | 1.06389317 |
| (24) $(1 - β2F^2) \times β3F^2$ | 0.22953791 | 0.21996283 | 0.25030583 |
| (25) $(1 - β2N^2) \times β3N^2$ | 0.32509417 | 0.3094599 | 0.3738214 |
| (26) $1/r_{LXF} - 1/r_{LXR}$ | −1.1372683 | −0.9079353 | −1.2729124 |
| | | −0.2515492 | |
| (27) SD1/fL | 2.66616898 | 1.60656218 | 1.84729939 |
| (28) fB/fL | 5.13077559 | 5.12593955 | 3.54141503 |
| (29) $fL \times \tan\omega_{max}$ | 2.30910847 | 2.28831395 | 2.15048988 |
| $2y_{max}$ | 1.624 | 1.624 | 1.624 |
| (30) ER3 | 0.857 | 0.751 | 0.623 |
| $fL/(2 \times F_{EX})$ | 0.10082527 | 0.10301483 | 0.09720028 |

|  | Example 7 | Example 8 | Example 9 |
|---|---|---|---|
| (1) fL/Rsp | 0.39589403 | 0.4314243 | 0.3910113 |
| (2) ΣDpc/fL | 5.31976658 | 4.48759499 | 4.16200581 |
| (3) ΣD3/fL | 7.84796988 | 8.17154509 | 5.78787886 |
| (4) $1/r_1 - 1/r_2$ | 0.02789861 | 0.02200448 | 0.27774691 |
| (5) $1/f_{3x} - 10 \times fL$ | −0.1670682 | −0.1137174 | −0.1520987 |
| (6) β3F | −0.9080881 | −0.9401166 | −0.9109319 |
| (7) $f_3/fL$ | 4.00688218 | 4.27663826 | 4.32350348 |
| (8) $fL/f_{31}$ | −0.1854074 | 0.03879834 | 0.03353994 |
| (9) $({}_a n_{SNi}' - {}_a n_{SNi})/{}_a r_{SNi}$ | 0.39766832 | 0.40190328 | 0.41577253 |
| (10) $({}_b n_{SNi}' - {}_b n_{SNi})/{}_b r_{SNi}$ | −0.2661625 | −0.2053562 | −0.1426686 |
| (11) $f_{3R}/fL$ | 6.60170102 | 4.54410961 | 4.30483635 |
| (12) $(\nu_{3RCP} - \nu_{3RCN}) - (\nu_{3FCP} - \nu_{3FCN})$ | 74.94 | 58.59 | 89.34 |
| (13) $fL/r_{SNr}$ | −0.4688375 | −0.4406472 | −0.278948 |
| (14) $(r_{3XF} - r_{3XR})/(r_{3XF} + r_{3XR})$ | −0.026215 | −0.0195072 | −0.0176652 |
| (15) $1/r_{3XC} \times r_{3XF}$ | −0.3229024 | −0.2927005 | −0.3911432 |
| (16) $1/r_{3XC} \times r_{3XR}$ | −0.306405 | −0.2814994 | −0.3775639 |
| (17) $\nu_{31P} - \nu_{32P}$ | −53.08 | 15.66 | −55.02 |
| (18) $\nu_{33P} - (\nu_{31P} + \nu_{32P})/2$ | 26.54 | 43.58 | 40.63 |
| (19) $\nu_{31N} - \nu_{32N}$ | 0 | 0 | 21.2 |
| (20) (R21F + R21R)/(R21F − R21R) | −4.3762103 | −4.5596133 | −6.7902008 |
| (21) D21/fL | 0.65401125 | 0.65121486 | 0.61218508 |
| (22) β2F | 1.10738 | 1.09942 | 1.10187 |
| (23) β2N/β2F | 1.04058228 | 1.04018482 | 1.04407961 |
| (24) $(1 - β2F^2) \times β3F^2$ | 0.20549211 | 0.19622592 | 0.19504605 |
| (25) $(1 - β2N^2) \times β3N^2$ | 0.29770948 | 0.28938864 | 0.29469696 |
| (26) $1/r_{LXF} - 1/r_{LXR}$ | −0.8354917 | 0.8377314 | −0.9532888 |
| | −0.3840369 | −0.4022526 | −0.342454 |
| (27) SD1/fL | 2.03028791 | 2.05644261 | 2.03914818 |

-continued

| | | | |
|---|---|---|---|
| (28) fB/fL | 5.1278428 | 5.12095323 | 5.36227231 |
| (29) fL × tanω$_{max}$ | 2.30155347 | 2.31473051 | 2.194474 |
| 2y$_{max}$ | 1.624 | 1.624 | 1.624 |
| (30) ER3 | 0.993 | 0.935 | 0.93 |
| fL/(2 × F$_{EX}$) | 0.10200435 | 0.10272317 | 0.09766221 |

| | Example 10 |
|---|---|
| (1) fL/Rsp | 0.43144155 |
| (2) ΣDpc/fL | 4.48741556 |
| (3) ΣD3/fL | 8.17121837 |
| (4) 1/r$_1$ − 1/r$_2$ | 0.02200448 |
| (5) 1/f$_{3x}$ − 10 × fL | −0.1137121 |
| (6) β3F | −0.9411887 |
| (7) f$_3$/fL | 4.27646727 |
| (8) fL/f$_{31}$ | 0.03879989 |
| (9) ($_a$n$_{SNi}'$ − $_a$n$_{SNi}$)/$_a$r$_{SNi}$ | 0.40190328 |
| (10) ($_b$n$_{SNi}'$ − $_b$n$_{SNi}$)/$_b$r$_{SNi}$ | −0.2053562 |
| (11) f$_{3R}$/fL | 4.54392792 |
| (12) (ν$_{3RCP}$ − ν$_{3RCN}$) − (ν$_{3FCP}$ − ν$_{3FCN}$) | 58.59 |
| (13) fL/r$_{SN}$ | −0.4406648 |
| (14) (r$_{3XF}$ − r$_{3XR}$)/(r$_{3XF}$ + r$_{3XR}$) | −0.0195072 |
| (15) 1/ r$_{3XC}$ × r$_{3XF}$ | −0.2927005 |
| (16) 1/r$_{3XC}$ × r$_{3XR}$ | −0.2814994 |
| (17) ν$_{31P}$ − ν$_{32P}$ | 15.66 |
| (18) ν$_{33P}$ − (ν$_{31P}$ + ν$_{32P}$)/2 | 43.58 |
| (19) ν$_{31N}$ − ν$_{32N}$ | 0 |
| (20) (R21F + R21R)/(R21F − R21R) | −4.5596133 |
| (21) D21/fL | 0.65118883 |
| (22) β2F | 1.09912 |
| (23) β2N/β2F | 1.03888565 |
| (24) (1 − β2F$^2$) × β3F$^2$ | 0.19582849 |
| (25) (1 − β2N$^2$) × β3N$^2$ | 0.28597518 |
| (26) 1/r$_{LXF}$ − 1/r$_{LXR}$ | −0.7264274 |
| | −0.4787074 |
| (27) SD1/fL | 2.30009848 |
| (28) fB/fL | 5.1223478 |
| (29) fL × tanω$_{max}$ | 4.17170907 |
| 2y$_{max}$ | 1.624 |
| (30) ER3 | 0.936 |
| fL/(2 × F$_{EX}$) | 0.1029528 |

Figure 21:
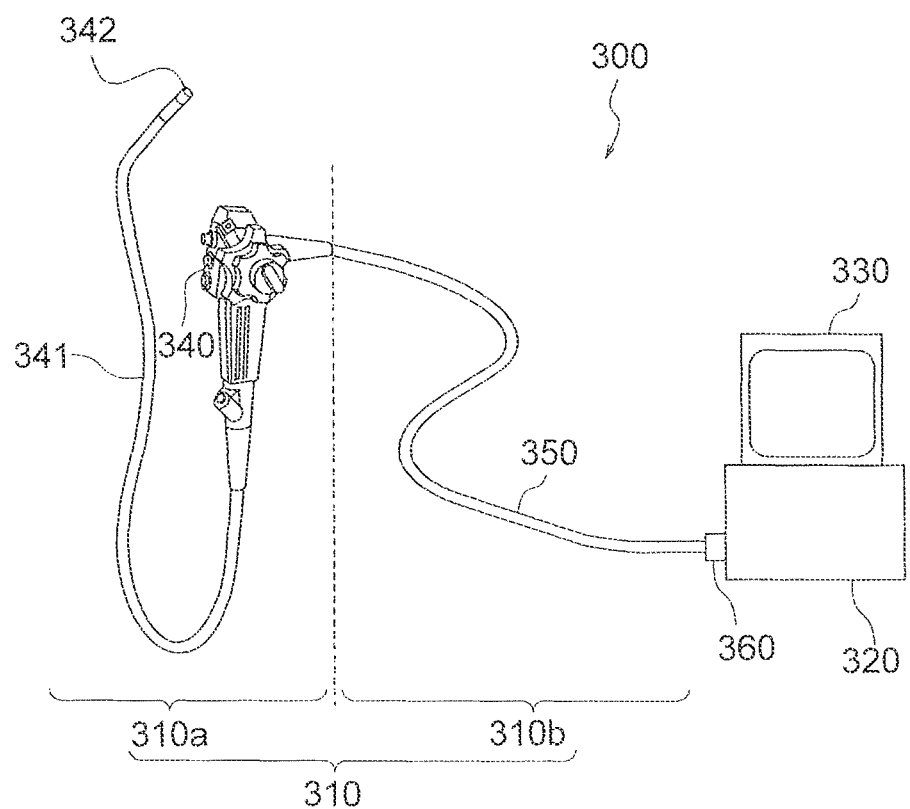
FIG. 21 is a diagram showing a schematic configuration of an endoscope system.

FIG. 21 is an example of an image pickup apparatus. In this example, the image pickup apparatus is an endoscope system. FIG. 21 is a diagram showing a schematic configuration of an endoscope system.

An endoscope system 300 is an observation system in which an electronic endoscope is used. The endoscope system 300 includes an electronic endoscope 310 and an image processing unit 320. The electronic endoscope 310 includes a scope section 310a and a connecting cord section 310b. Moreover, a display unit 330 is connected to the image processing unit 320.

The scope section 310a is mainly divided into an operating portion 340 and an inserting portion 341. The inserting portion 341 is long and slender, and can be inserted into a body cavity of a patient. Moreover, the inserting portion 341 is formed of a flexible member. An observer can carry out various operations by an angle knob that is provided to the operating portion 340.

Moreover, the connecting cord section 310 b is extended from the operating portion 340. The connecting cord section 301b includes a universal cord 350. The universal cord 350 is connected to the image processing unit 320 via a connector 360.

The universal cord 350 is used for transceiving of various types of signals. Various types of signals include signals such as a power-supply voltage signal and a CCD (charge coupled device) driving signal. These signals are transmitted from a power supply unit and a video processor to the scope section 310a. Moreover, various types of signals include a video signal. This signal is transmitted from the scope section 310a to the video processor.

Peripheral equipment such as a VTR (video tape recorder) deck and a video printer can be connected to the video processor inside the image processing unit 320. The video processor carries out signal processing on a video signal from the scope section 310a. On the basis of the video signal, an endoscope image is displayed on a display screen of the display unit 330.

Figure 22:
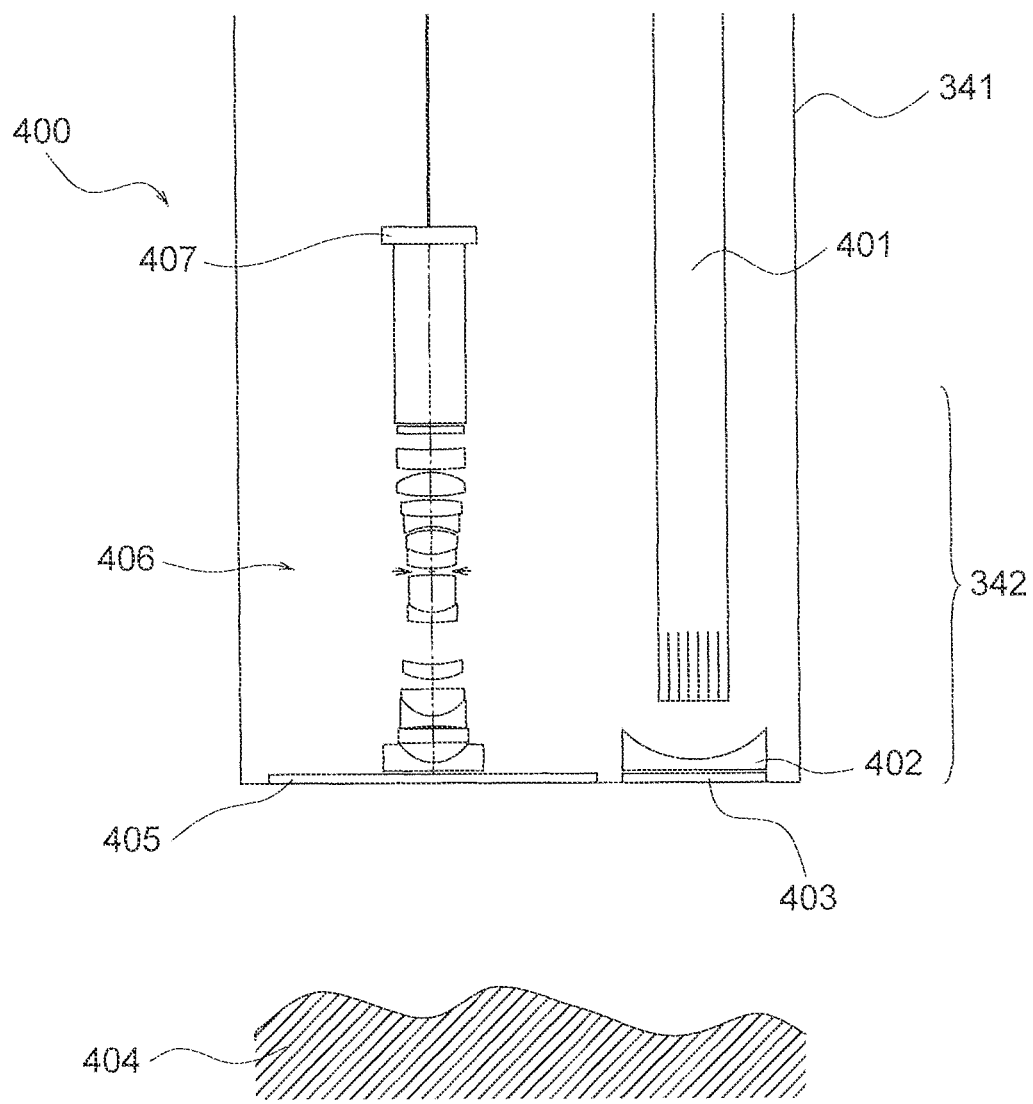
FIG. 22 is a diagram showing an arrangement of an optical system of an endoscope.

An optical system is disposed at a front-end portion 342 of the inserting portion 341. FIG. 22 is a diagram showing an arrangement of the optical system of the endoscope. An optical system 400 includes an illuminating section and an observation section.

The illuminating section includes a light guide 401 and an illuminating lens 402. The light guide 401 transmits illumination light to the front-end portion 342 of the inserting portion 341. The transmitted light is emerged from a front-end surface of the light guide 401.

At the front-end portion 342, the illuminating lens 402 is disposed. The illuminating lens 402 is disposed at a position of facing the front-end surface of the light guide 401. The illumination light passes through the illuminating lens 402 and is emerged from an illumination window 403. As a result, an observation object region 404 of an inside of an object (hereinafter, referred to as 'observation region 404') is illuminated.

At the front-end portion 342, an observation window 405 is disposed next to the illumination window 403. Light from the observation region 404 is incident on the front-end portion 342 through the observation window 405. An observation portion is disposed behind the observation window 405.

The observation portion includes a wide-angle optical system 406 and an image sensor 407. The wide-angle optical system of the example 1 is used for the wide-angle optical system 406, for instance.

Reflected light from the observation region 404 passes through the wide-angle optical system 406 and is incident on the image sensor 407. On an image pickup surface of the image sensor 407, an image (an optical image) of the observation region 404 is formed. The image of the observation region 404 is converted photoelectrically by the image sensor 407, and thereby an image of the observation region 404 is acquired. The image of the observation region 404 is displayed on the display unit 330. By doing so, it is possible to observe the image of the observation region 404.

In the wide-angle optical system 406, an image plane is curved shape. The image sensor 407 has a curved-shape light receiving surface (an image pickup surface) same as an shape of the image plane. By using the image sensor 407, it is possible to improve an image quality of the acquired image.

Figure 23:
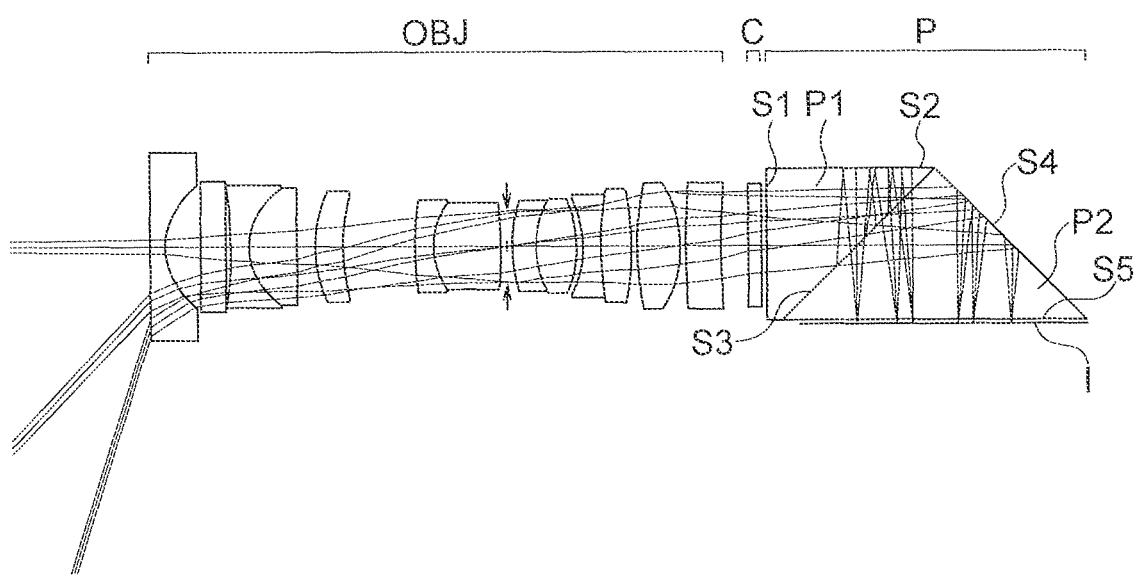
FIG. 23 is a diagram showing an arrangement of an optical system of an image pickup apparatus.
Figure 24:
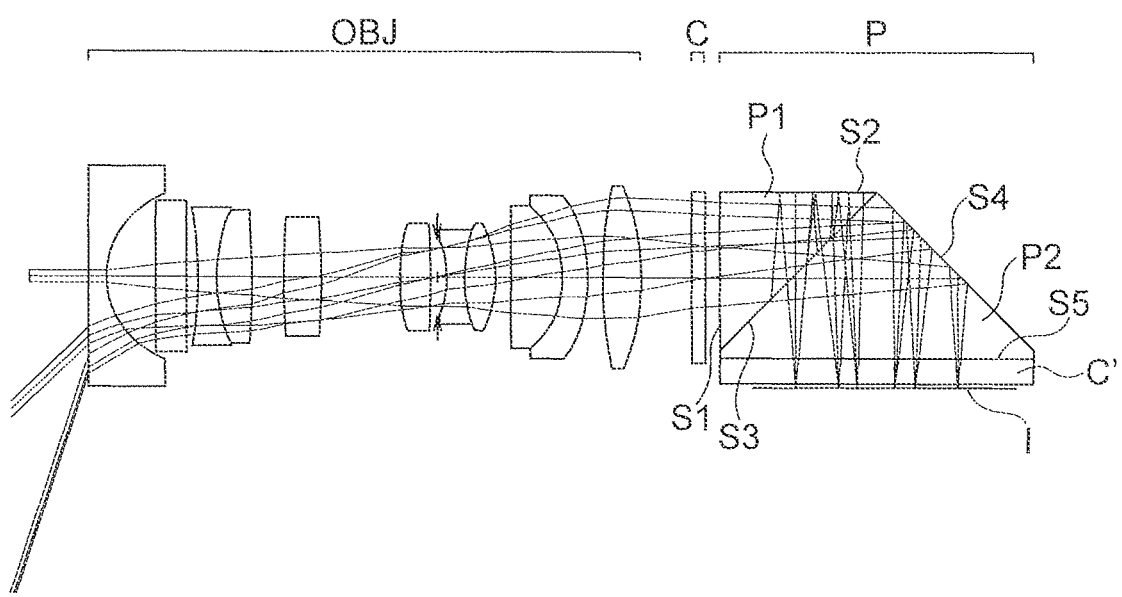
FIG. 24 is a diagram showing an arrangement of an optical system of an image pickup apparatus.

FIG. 23 and FIG. 24 are a diagram showing an arrangement of an optical system of an image pickup apparatus. The optical system includes an objective optical system OBJ, a cover glass C, and a prism P. The cover glass C is disposed between the objective optical system OBJ and the prism P. An optical filter may be disposed instead of the cover glass C. Or, the cover glass C may not be disposed.

In FIG. 23, the wide-angle optical system of the example 1 is used for the objective optical system OBJ. In FIG. 24, the wide-angle optical system of the example 2 is used for the objective optical system OBJ. Moreover, in FIG. 24, the cover glass C' is disposed between the prism P and image plane I.

The prism P includes a prims P1 and a prism P2. Both the prism P1 and the prism P2 are triangular prisms. An optical-path splitting element is formed by the prism P1 and the prism P2.

The prism P1 has an optical surface S1, an optical surface S2, and an optical surface S3. The prism P2 has an optical surface S3, an optical surface S4, and an optical surface S5. The prism P1 is cemented to the prism P2. A cemented surface is formed by the prism P1 and the prism P2. The optical surface S3 is a cemented surface.

Light emerged from the objective optical system OBJ (hereinafter, referred to as 'imaging light') passes through the cover glass C, and is incident on the optical surface S1. The optical surface S1 being a transmitting surface, the imaging light is transmitted through the optical surface S1.

Next, the imaging light is incident on the optical surface S3. The optical surface S3 is disposed so that a normal of the surface is at 45 degrees with respect to an optical axis. The imaging light incident on the optical surface S3 is divided into light transmitted through the optical surface S3 (hereinafter, referred to as 'imaging light 1') and light reflected at the optical surface S3 (hereinafter, referred to as 'imaging light 2').

The imaging light 1 and the imaging light 2 travel in mutually different directions. When an optical path through which the imaging light 1 travels is a first optical path and an optical path through which the imaging light 2 travels is a second optical path, the first optical path and the second optical path are formed by the optical surface S3. As just described, the optical surface S3 functions as an optical-path splitting surface.

The first optical path is formed on an extension line of an optical path of the objective optical system OBJ. The second optical path is formed to intersect the first optical path. In FIG. 23 and FIG. 24, the second optical path is orthogonal to the first optical path.

The optical surface S3, the optical surface S4, and the optical surface S5 are located in the first optical path. The imaging light 1 transmitted through the optical surface S3 is incident on the optical surface S4. The optical surface S4 is a reflecting surface. The imaging light 1 is reflected at the optical surface S4, and is incident on the optical surface S5. The optical surface S5 is a transmitting surface. The imaging light 1 is transmitted through the optical surface S5, and is converged on an image plane I near the optical surface S5. An optical image by the imaging light 1 is formed on the image plane I.

The optical surface S3, the optical surface S2, the optical surface S3, and the optical surface S5 are located in the second optical path. The imaging light 2 reflected at the optical surface S3 is incident on the optical surface S2. The optical surface S2 is a reflecting surface. The imaging light 2 is reflected at the optical surface S2, and is incident on the optical surface S3. At the optical surface S3, the imaging light 2 is divided into light transmitted through the optical surface S3 and light reflected at the optical surface S3.

The imaging light 2 transmitted through the optical surface S3 is incident on the optical surface S5. The imaging light 2 is transmitted through the optical surface S5, and is converged on the image plane I near the optical surface S5. An optical image by the imaging light 2 is formed on the image plane I.

Since two optical paths are formed in the optical system shown in FIG. 23 and FIG. 24, two optical images are formed on the same plane. The same plane is the image plane I in the two optical paths.

In a case in which an optical-path length of the first optical path and an optical-path length of the second optical path are same, two focused optical images are formed at different positions on the same plane. The two optical images are optical images when the same object is focused. Accordingly, a position of an object plane for one optical image and a position of an object plane for the other optical image are same.

Whereas, even in a case in which the optical-path length of the first optical path and the optical-path length of the second optical path are different, two focused optical images are formed at different positions on the same plane. However, the two optical images are optical images when different objects are focused. Accordingly, a position of an object plane for one optical image and a position of an object plane for the other optical image are different.

For instance, it is assumed that the optical-path length of the first optical path is shorter than the optical-path length of the second optical path. In this case, the object plane of the optical image formed by the imaging light 1 is positioned far from the object plane of the optical image formed by the imaging light 2. As just described, the focus is adjusted for each of the two object planes in which distance from the objective optical system (hereinafter, referred to as 'object distance') differs from each other. Even when the object distance differs for two object planes, the two optical images are formed at different locations in on the same plane.

The objective optical system OBJ has a section which is focused (hereinafter, referred to as 'focusing section'). The focusing section is a section expressed by the object distance, and corresponds to a depth of field of the objective optical system OBJ. In the focusing section, wherever the object plane is positioned, a focused optical image is formed.

In a case in which the object distance differs for two object planes, there occurs a shift between a position of the focusing section for one object plane and a position of the focusing section for the other object plane. By setting appropriately the distance of the two object planes, it is possible to overlap a part of the focusing section for the one object plane and a part of the focusing section for the other object plane.

Thus, two optical images having the focusing section shifted are captured, and accordingly, two images are acquired. Moreover, only a focused area (an image area of a range corresponding to the depth of field) is extracted from the two images that were acquired, and the areas extracted are combined. By doing so, it is possible to acquire an image with a large depth of field.

For the optical surface S3, it is possible to use a half-mirror surface or a polarizing-beam splitter surface for example.

In a case in which the optical surface S3 is a half-mirror surface, a half of a quantity of imaging light is reflected at the optical surface S3 and the remaining half of the quantity of imaging light is transmitted through the optical surface S3. Accordingly, a quantity of the imaging light 2 becomes half of the quantity of the imaging light. The imaging light 2 is reflected at the optical surface S2. The imaging light 2 reflected at the optical surface S2 is transmitted through the optical surface S3. At the optical surface S3, only half of the quantity of the imaging light 2 can be transmitted.

In a case in which the optical surface S3 is a polarizing-beam splitter surface, a depolarization plate or a wavelength plate may be used instead of the cover glass C. Moreover, the optical surface S2 is not a reflecting surface but is a transmitting surface. A reflecting surface is disposed at a position away from the optical surface S2. Furthermore, a quarter-wave plate is disposed between the optical surface S2 and the reflecting surface.

P-polarized light is polarized light having an amplitude of light in a paper plane, and S-polarized light is polarized light having an amplitude in a plane orthogonal to the paper plane. When it is assumed that the P-polarized light is transmitted through the optical surface S3 and the S-polarized light is reflected at the optical surface S3, the P-polarized light corresponds to the imaging light 1 and the S-polarized light corresponds to the imaging light 2.

For instance, when the depolarization plate is used instead of the cover glass C, the imaging light passes through the depolarization plate. Consequently, in the imaging light emerged from the depolarization plate, a proportion of the P-polarized light and the S-polarized light in the imaging light becomes substantially half. The imaging light incident on the optical surface S3 is divided into the P-polarized light and the S-polarized light at the optical surface S3. Accordingly, the quantity of the imaging light 2 becomes half of the quantity of the imaging light.

The imaging light 2, when directed from the optical surface S3 toward the optical surface S2, is S-polarized light. In a case in which the optical surface S2 is a reflecting surface, the imaging light 2 is reflected toward the optical surface 3 as the S-polarized light as it has been. The imaging light 2 directed from the optical surface S2 toward the optical surface S3 being the S-polarized light, cannot be transmitted through the optical surface S3.

Whereas, in a case in which the optical surface S2 is a transmitting surface, the imaging light 2 is reflected at the reflecting surface. The λ/4 plate is disposed between the optical surface S2 and the reflecting surface. By the imaging light 2 travelling to and from between the optical surface S2 and the reflecting surface, a direction of polarization for the imaging light 2 rotates 90 degrees. Accordingly, it is possible to convert the S-polarized light to the P-polarized light. As a result, the imaging light directed from the optical surface S2 toward the optical surface S3 becomes the P-polarized light.

The imaging light 2 converted to the P-polarized light reaches the optical surface S3. Accordingly, the imaging light 2 is not reflected at the optical surface S3. In other words, at the optical surface S3, almost whole of the amount of the imaging light 2 can be transmitted through.

Figure 25A:
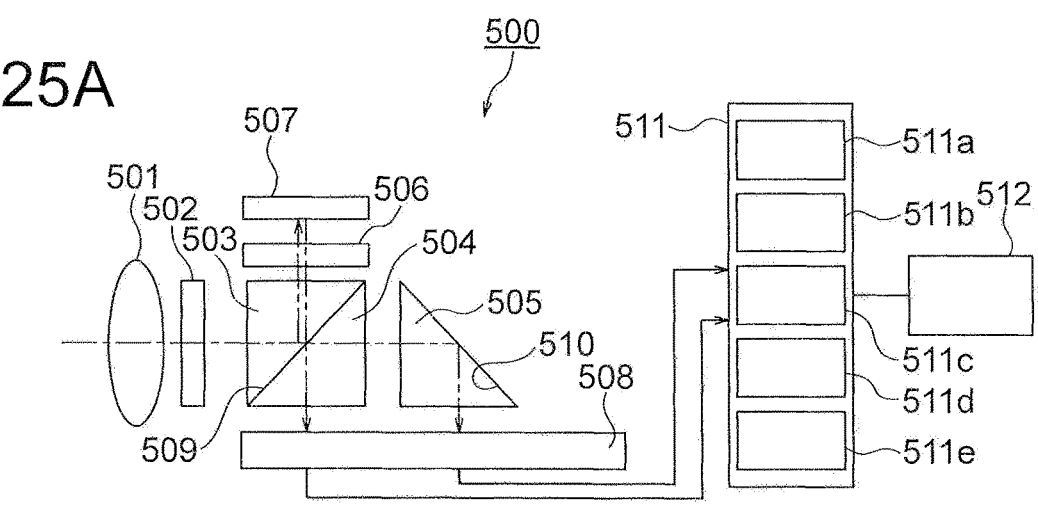
FIG. 25A is a diagram showing a schematic configuration of an image pickup apparatus.
Figure 25B:
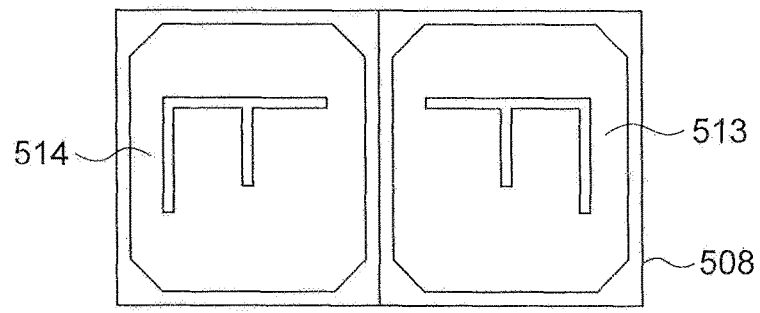
FIG. 25B is a diagram showing orientations of images on an image sensor.

FIG. 25A and FIG. 25B are diagrams showing a schematic configuration of an image pickup apparatus. FIG. 25A is a diagram showing an overall configuration, and FIG. 25B is a diagram showing an orientation of an object.

As shown in FIG. 25A, an image pickup apparatus 500 includes an objective optical system 501, a depolarization plate 502, a first prism 503, a second prism 504, a third prism 505, a wavelength plate 506, a mirror 507, an image sensor 508, an image processor 511, and an image display unit 512.

In the image pickup apparatus 500, an optical-path splitting element is formed by the first prism 503, the second prism 504, and the third prism 505.

The objective optical system 501 forms an image of an object. The depolarization plate 502 is disposed between the objective optical system 501 and the first prism 503.

The first prism 503 and the second prism 504 are cemented. A cemented surface 509 is formed by the first prism 503 and the second prism 504. Light incident on the cemented surface 509 is divided into light reflected at the cemented surface 509 and light transmitted through the cemented surface 509.

It is possible to use a polarizing-beam splitter surface for the cemented surface 509. In this case, P-polarized light is transmitted through the cemented surface 509 and S-polarized light is reflected at the cemented surface 509.

The P-polarized light transmitted through the cemented surface 509 emerges from the second prism 504. The P-polarized light is incident on the third prism 505 and reaches an optical surface 510. The optical surface 510, for instance, is a mirror surface. Accordingly, the P-polarized light is reflected at the optical surface 510.

The P-polarized light reflected at the optical surface 510 emerges from the third prism 505 and is incident on the image sensor 508. As shown in FIG. 25B, the image sensor 508 has a first area 513 and a second area 514. The P-polarized light reflected at the optical surface 510 is incident on the first area 513. Accordingly, an optical image is formed on the first area 513.

On the other hand, the S-polarized light reflected at the cemented surface 509 emerges from the first prism 503. The S-polarized light is incident on the wavelength plate 506. A quarter-wave plate is used for the wavelength plate 506. Consequently, the S-polarized light is converted to circularly-polarized light at the wavelength plate 506. As a result, the circularly-polarized light emerges from the wavelength plate 506.

The circularly-polarized light is reflected at the mirror 507 and is incident once again on the wavelength plate 506. Light emerged from the wavelength plate 506 is incident on the first prism 503 and reaches the cemented surface 509. The circularly-polarized light incident on the wavelength plate 506 is converted to P-polarized light at the wavelength plate 506. The light reached the cemented surface 509 being the P-polarized light, the light reached the cemented surface 509 is transmitted through the cemented surface 509.

The P-polarized light which is transmitted through the cemented surface 509 emerges from the second prism 504 and is incident on the image sensor 508. As mentioned above, the image sensor 508 has the first area 513 and the second area 514. The P-polarized light transmitted through the cemented surface 509 is incident on the second area 514. As a result, an optical image is formed on the second surface 514.

For instance, a rolling shutter system is adopted for the image sensor 508. In the rolling shutter system, image information for a line is read for each line one-by-one. The image sensor 508 is connected to the image processor 511. Image information which is read is input to the image processor 511.

The image processor 511 includes a second image processing section 511*b*. In the second image processing section 511*b*, it is possible to select a focused image as an image for display by using the image information that has been read for each line one-by-one. Images for each line selected by the second image processing section 511*b* are combined and displayed on the image display unit 512.

The image processor 511 will be described below. The image processor 511 is provided to a central processing unit (not shown in the diagram). The image processor 511 includes a first image processing section 511*a*, the second image processing section 511*b*, a third image processing section 511*c*, a fourth image processing section 511*d*, and a fifth image processing section 511*e*.

In the first image processing section 511*a*, an orientation of an image acquired from the first area 513 (hereinafter, referred to as 'first image') and an orientation of an image acquired from the second area 514 (hereinafter, referred to as 'second image') are corrected. In correction of the orientation of the image, the image is rotated for example.

The orientation of the first image and the orientation of the second image are determined by an orientation of the optical image formed in the first area 513 (hereinafter, referred to as 'first optical image') and an orientation of the optical image formed in the second area 514 (hereinafter, referred to as 'second optical image') respectively.

Figure 26:
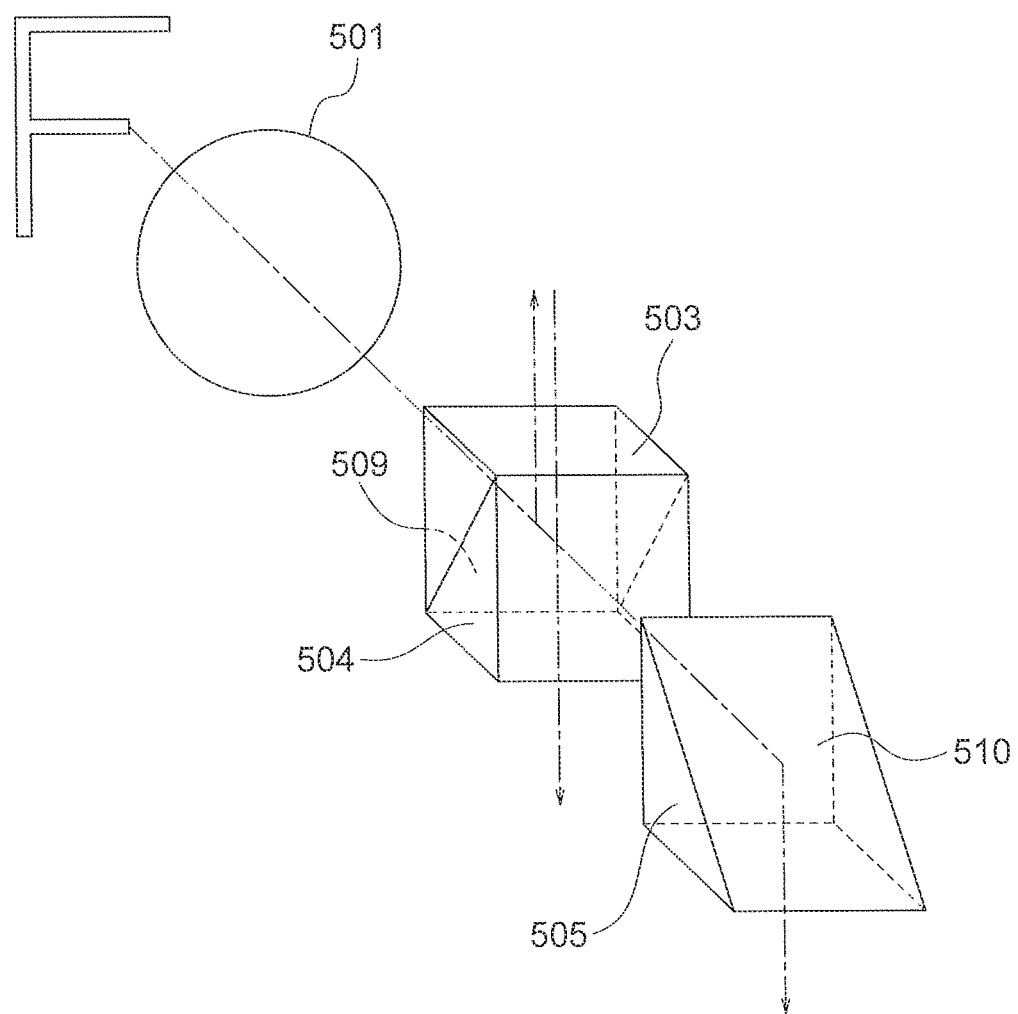
FIG. 26 is a diagram showing a positional relationship of an object, an objective optical system, and an optical-path splitting element.

FIG. 26 is a diagram showing a positional relationship of an object, an objective optical system, and an optical-path splitting element. For instance, a case of observing a character 'F' as shown in FIG. 26 will be described below. Each of the orientation of the first optical image and the orientation of the second optical image is an orientation as shown in FIG. 25B.

As shown in FIG. 25B, the first optical image and the second optical image are mirror images of each other. Furthermore, when a vertical orientation of a paper surface is an upright direction, the first optical image and the second optical image are rotated 90 degrees from the upright direction.

Therefore, in a case of displaying an image of an object on the image display unit 512, in the first image processing section 511*a*, the first image is rotated 90 degrees with a central point of the first area 513 as a center. Even regarding the second image, the second image is rotated 90 degrees with a central point of the area 514 as a center. Moreover, regarding the second image, the second image is inverted, and a mirror image is corrected.

As the processing by the first image processing section 511*a* is terminated, processing by the second image processing unit 511*b* is executed. However, according to the requirement, processing by at least one of the third image processing section 511*c*, the fourth image processing section 511*d*, and the fifth image processing section 511*e* may be executed before executing the processing by the second image processing section 511*b*.

The third image processing section 511*c* is configured so that a white balance of the first image and a white balance of the second image are adjustable. The fourth image processing section 511*d* is configured so that a center position of the first image and a center position of the second image are movable or selectable. The fifth image processing section 511*e* is configured so that a display range of the first image and a display range of the second image are adjustable. Moreover, the fifth image processing section 511*e* may be configured so that a display magnification is adjustable instead of the display range.

The second image processing section 511*b* is configured to compare the first image and the second image, and to select an image of a focused area as an image for display.

The second image processing section 511*b* has a high-pass filter, a comparator, and a switch. The high-pass filter is connected to each of the first area 513 and the second area 514. In the high-pass filter, a high component is extracted from each of the first image and the second image.

Outputs of the two high-pass filters are input to the comparator. The high components extracted in the two high-pass filters are compared in the comparator. A comparison result is input to the switch. Moreover, the first area 513 and the second area 514 are connected to the switch. Accordingly, the comparison result, a signal of the first image, and a signal of the second image are input to the switch.

In the switch, an area with many high component in the first image and an area with many high component in the second image are selected on the basis of the comparison result.

The image display unit 512 has a display area. An image selected by the second processing section 511*b* is displayed in the display area. The image display unit 512 may have display areas displaying the first image and the second image.

According to the present disclosure, it is possible to provide a wide-angle optical system in which various aberrations are corrected favorably and an outer diameter of a lens that moves and an outer diameter of a lens which is located near a lens unit that moves are adequately small, and which has an appropriate back focus, and an image pickup apparatus in which the wide-angle optical system is used.

As described heretofore, the present disclosure is suitable for a wide-angle optical system in which various aberrations are corrected favorably and an outer diameter of a lens that moves and an outer diameter of a lens which is located near a lens unit that moves are adequately small, and which has an appropriate back focus, and an image pickup apparatus in which the wide-angle optical system is used.

What is claimed is:

1. A wide-angle optical system having a lens component which has a plurality of optical surfaces, and in the lens component, two optical surfaces are in contact with air, and at least one optical surface is a curved surface, the wide-angle optical system comprising, in order from an object side:
  a first lens unit having a negative refractive power;
  a second lens unit having a positive refractive power; and
  a third lens unit having a positive refractive power,
  wherein:
  at a time of carrying out a focal-position adjustment from a far point to a near point, the second lens unit is moved from a first position toward a second position, the first position being a position at which a distance between the first lens unit and the second lens unit is at a minimum, and the second position being a position at which a distance between the second lens unit and the third lens unit is at a minimum,
  the third lens unit has not less than nine refractive lens surfaces, the third lens unit including a positive singlet lens on an image side of a shared cemented surface, the shared cemented surface having a negative refractive power and being a shared cemented surface nearest to an image plane from among shared cemented surfaces in the third lens unit, and the third lens unit having a plurality of refractive lens surfaces having a negative refractive power on the object side of the shared cemented surface,
  the third lens unit has at least one refractive lens surface having a positive refractive power which satisfies the following conditional expression (1), on the object side of two lens surfaces located on the image side, out of the plurality of refractive lens surfaces having the negative refractive power, and
  the following conditional expression (28) is satisfied:

$$0.02 < fL/Rsp < 1.20 \quad (1),$$

$$3.5 < fB/fL < 10 \quad (28)$$

where,
Rsp denotes a radius of curvature of the refractive lens surface having the positive refractive power,
fL denotes a focal length of the wide-angle optical system at the first position, and
fB denotes an air conversion length of a distance from a vertex of the image side of a lens component nearest to the image plane up to an imaging surface.

2. The wide-angle optical system according to claim 1, wherein the refractive lens surface having the positive refractive power satisfies the following conditional expression (2):

$$1.5 < \Sigma Dpc/fL < 10.0 \quad (2)$$

where,
$\Sigma Dpc$ denotes a distance on an optical axis from the refractive lens surface having the positive refractive power up to the shared cemented surface.

3. The wide-angle optical system according to claim 1, wherein the following conditional expression (3) is satisfied $$2.0 < \Sigma D3/fL < 15.0 \quad (3):$$

where,
$\Sigma D3$ denotes a distance on an optical axis from a lens surface of the third lens unit nearest to an object up to a lens surface of the third lens unit nearest to the image plane.

4. The wide-angle optical system according to claim 1, wherein the third lens unit includes a lens component which satisfies the following conditional expressions (4) and (5) simultaneously:

$$1/r_2 < 1/r_1 \quad (4),$$

$$1/f_{3x} < 1/10 \times fL \quad (5)$$

where,
$r_1$ denotes a radius of curvature of a surface nearest to an object of each lens component in the third lens unit,
$r_2$ denotes a radius of curvature of a surface nearest to the image plane of each lens component in the third lens unit,
$f_{3x}$ denotes a focal length of each lens component in the third lens unit, and
fL denotes the focal length of the wide-angle optical system at the first position.

5. The wide-angle optical system according to claim 1, wherein the following conditional expression (6) is satisfied:

$$-1.5 < \beta 3F < -0.3 \quad (6)$$

where,
$\beta 3F$ denotes a magnification of the third lens unit at the first position.

6. The wide-angle optical system according to claim 1, wherein the following conditional expression (7) is satisfied:

$$2.0 < f_3/fL < 6.0 \quad (7)$$

where,
$f_3$ denotes a focal length of the third lens unit.

7. The wide-angle optical system according to claim 1, wherein the following conditional expression (8) is satisfied:

$$-0.8 < fL/f_{31} < 1.0 \quad (8)$$

where,
$f_{31}$ denotes a focal length of a lens component located nearest to an object in the third lens unit.

8. The wide-angle optical system according to claim 1, comprising:
a first refractive lens surface,
wherein:
the first refractive lens surface is a refractive lens surface which satisfies the following conditional expression (9), and
the first refractive lens surface is located at a distance not more than $2.5 \times fL$ toward the image side from a vertex nearest to an object of the third lens unit:

$$0.10 < (_a n_{SNi}' - _a n_{SNi})/_a r_{SNi} < 0.70 \quad (9)$$

where,
$_a n_{SNi}$ denotes a refractive index for a d-line of a medium located on the object side of the first refractive lens surface,
$_a n_{SNi}'$ denotes a refractive index for the d-line of a medium located on the image side of the first refractive lens surface, and
$_a r_{SNi}$ denotes a radius of curvature near an optical axis of the first refractive lens surface.

9. The wide-angle optical system according to claim 1, comprising:
a second refractive lens surface,
wherein:
the second refractive lens surface is a refractive lens surface which satisfies the following conditional expression (10), and the second refractive lens surface is located at a distance not less than 2.5×fL toward the image side from a vertex nearest to an object of the third lens unit:

$$-0.60 < (_bn_{SNi}' - _bn_{SNi})/_br_{SNi} < -0.05 \quad (10)$$

where, $_bn_{SNi}$ denotes a refractive index for a d-line of a medium located on the object side of the second refractive lens surface, $_bn_{SNi}'$ denotes a refractive index for the d-line of a medium located on the image side of the second refractive lens surface, and $_br_{SNi}$ denotes a radius of curvature near an optical axis of the second refractive lens surface.

10. The wide-angle optical system according to claim 1, wherein:

the third lens unit includes a plurality of positive single singlet lenses, and from among the plurality of positive single singlet lenses, a positive single singlet lens which is located nearest to the image plane satisfies the following conditional expression (11):

$$2.0 < f_{3R}/fL < 10.0 \quad (11)$$

where, $f_{3R}$ denotes a focal length of the positive singlet lens located nearest to the image plane.

11. The wide-angle optical system according to claim 1, wherein:

the third lens unit includes an object-side cemented lens which is located nearest to an object and an image-side cemented lens which is located nearest to the image plane, and the following conditional expression (12) is satisfied:

$$-30 < (v_{3RCP} - v_{3RCN}) - (v_{3FCP} - v_{3FCN}) < 110 \quad (12)$$

where, $v_{3FCP}$ denotes an Abbe number for a d-line for a positive lens in the object-side cemented lens, $v_{3FCN}$ denotes an Abbe number for the d-line for a negative lens in the object-side cemented lens, $v_{3RCP}$ denotes an Abbe number for the d-line for a positive lens in the image-side cemented lens, and $v_{3RCN}$ denotes an Abbe number for the d-line for a negative lens in the image-side cemented lens.

12. The wide-angle optical system according to claim 1, wherein the shared cemented surface satisfies the following conditional expression (13):

$$-0.80 < fL/r_{SNr} < 0.60 \quad (13)$$

where, $r_{SNr}$ denotes a radius of curvature near an optical axis of the shared cemented surface.

13. The wide-angle optical system according to claim 1, wherein a predetermined cemented lens which satisfies the following conditional expressions (14), (15), and (16) is included in lens components up to a third lens component from the object side in the third lens unit:

$$-1.0 < (r_{3XF} - r_{3XR})/(r_{3XF} + r_{3XR}) < 0.5 \quad (14)$$

$$1/r_{3XC} \times r_{3XF} < 0 \quad (15)$$

$$1/r_{3XC} \times r_{3XR} < 0 \quad (16)$$

where, $r_{3XF}$ denotes a radius of curvature of a surface nearest to an object of the predetermined cemented lens, $r_{3XR}$ denotes a radius of curvature of a surface nearest to the image plane of the predetermined cemented lens, and $r_{3XC}$ denotes a radius of curvature on an optical axis of a shared cemented surface of the predetermined cemented lens.

14. The wide-angle optical system according to claim 1, wherein:

the third lens unit includes a plurality of positive lenses, the plurality of positive lenses include a first positive lens and a second positive lens, the first positive lens, among the plurality of positive lenses, is a positive lens located nearest to the object, the second positive lens, among the plurality of positive lenses, is a positive lens located second from the object, and the following conditional expression (17) is satisfied:

$$-75 < v_{31P} - v_{32P} < 35 \quad (17)$$

where, $v_{31P}$ denotes an Abbe number for the first positive lens, and $v_{32P}$ denotes an Abbe number for the second positive lens.

15. The wide-angle optical system according to claim 1, wherein:

the third lens unit includes a plurality of positive lenses, the plurality of positive lenses include a first positive lens, a second positive lens, and a third positive lens, the first positive lens, among the plurality of positive lenses, is a positive lens located nearest to the object, the second positive lens, among the plurality of positive lenses, is a positive lens located second from the object, the third positive lens, among the plurality of positive lenses, is a positive lens located third from the object, and the following conditional expression (18) is satisfied:

$$-10 < v_{33P} - (v_{31P} + v_{32P})/2 < 70 \quad (18)$$

where, $v_{31P}$ denotes an Abbe number for the first positive lens, $v_{32P}$ denotes an Abbe number for the second positive lens, and $v_{33P}$ denotes an Abbe number for the third positive lens.

16. The wide-angle optical system according to claim 1, wherein:

the third lens unit includes a plurality of negative lenses, the plurality of negative lenses include a first negative lens and a second negative lens, the first negative lens, among the plurality of negative lenses, is a negative lens located nearest to the object, the second negative lens, among the plurality of negative lenses, is a negative lens located second from the object, and the following conditional expression (19) is satisfied:

$$-20 < v_{31N} - v_{32N} < 40 \quad (19)$$

where, $v_{31N}$ denotes an Abbe number for the first negative lens, and $v_{32N}$ denotes an Abbe number for the second negative lens.

17. The wide-angle optical system according to claim 1, wherein the third lens unit is fixed at the time of carrying out the focal-position adjustment.

18. The wide-angle optical system according to claim 1, wherein the following conditional expression (20) is satisfied:

$$-50 < (R21F+R21R)/(R21F-R21R) < 15 \quad (20)$$

where,
R21F denotes a radius of curvature of a surface on the object side of a predetermined lens component,
R21R denotes a radius of curvature of a surface on an image side of the predetermined lens component, and the predetermined lens component is a lens component located nearest to the object in the second lens unit.

19. The wide-angle optical system according to claim 1, wherein the following conditional expression (21) is satisfied:

$$0.3 < D21/fL < 2.0 \quad (21)$$

where,
D21 denotes a distance on an optical axis between a surface of the second lens unit nearest to the object and a surface of the second lens unit nearest to the image plane.

20. The wide-angle optical system according to claim 1, wherein the following conditional expression (22) is satisfied:

$$1.04 < \beta 2F < 1.40 \quad (22)$$

where,
$\beta 2F$ denotes a magnification of the second lens unit at the first position.

21. The wide-angle optical system according to claim 1, wherein the following conditional expression (23) is satisfied:

$$1.01 < \beta 2N/\beta 2F < 1.15 \quad (23)$$

where,
$\beta 2F$ denotes a magnification of the second lens unit at the first position, and
$\beta 2N$ denotes a magnification of the second lens unit at the second position.

22. The wide-angle optical system according to claim 1, wherein the following conditional expression (24) is satisfied:

$$0.10 < (1-\lambda F^2) \times \beta 3F^2 < 0.45 \quad (24)$$

where,
$\beta 2F$ denotes a magnification of the second lens unit at the first position, and
$\beta 3F$ denotes a magnification of the third lens unit at the first position.

23. The wide-angle optical system according to claim 1, wherein the following conditional expression (25) is satisfied:

$$0.15 < (1-\beta 2N^2) \times \beta 3N^2 < 0.60 \quad (25)$$

where,
$\beta 2N$ denotes a magnification of the second lens unit at the second position, and
$\beta 3N$ denotes a magnification of the third lens unit at the second position.

24. The wide-angle optical system according to claim 1, wherein the second lens unit includes only a positive lens.

25. The wide-angle optical system according to claim 1, wherein the first lens unit includes only a lens component which satisfies the following conditional expression (26):

$$1/r_{1XF} < 1/r_{1XR} \quad (26)$$

where,
$r_{1XF}$ denotes a radius of curvature on an optical axis of a surface nearest to an object of each lens component in the first lens unit, and
$r_{1XR}$ denotes a radius of curvature on the optical axis of a surface nearest to the image plane of each lens component in the first lens unit.

26. The wide-angle optical system according to claim 1, wherein:
the first lens unit includes only a plurality of negative singlet lenses, and
each of the plurality of negative singlet lenses has an Abbe number larger than an Abbe number for a positive lens nearest to an object in the third lens unit.

27. The wide-angle optical system according to claim 1, wherein the following conditional expression (27) is satisfied:

$$0.20 < SD1/fL < 5.0 \quad (27)$$

where,
SD1 denotes a distance from a vertex nearest an object in the first lens unit up to a vertex nearest to the image plane in the first lens unit.

28. The wide-angle optical system according to claim 1, wherein the following conditional expression (29) is satisfied:

$$2 \times y_{max} < fL \times \tan \omega_{max} \quad (29)$$

where,
$y_{max}$ denotes a maximum image height, and
$\omega_{max}$ denotes an angle of view corresponding to the maximum image height.

29. The wide-angle optical system according to claim 1, wherein the following conditional expression (30) is satisfied:

$$ER3 < fL/(2 \times F_{EX}) \quad (30)$$

where,
ER3 denotes an effective radius of the shared cemented surface, and
$F_{EX}$ denotes an effective F-number at the first position.

30. An image pickup apparatus comprising:
an optical system; and
an image sensor which is disposed on an image plane, wherein:
the image sensor has an image pickup surface, and converts an image formed on the image pickup surface by the optical system to an electric signal, and
the optical system is the wide-angle optical system according to claim 1.

* * * * *